(12) United States Patent
Dorin et al.

(10) Patent No.: US 7,022,672 B2
(45) Date of Patent: Apr. 4, 2006

(54) FORMULATION, SOLUBILIZATION, PURIFICATION, AND REFOLDING OF TISSUE FACTOR PATHWAY INHIBITOR

(75) Inventors: Glenn J. Dorin, San Rafael, CA (US); Bo H. Arve, Cary, NC (US); Gregory L. Pattison, Oakland, CA (US); Robert F. Halenbeck, San Rafael, CA (US); Kirk Johnson, Moraga, CA (US); Bao-Lu Chen, San Ramon, CA (US); Rejsharan K. Bana, Woodinville, WA (US); Maninder S. Hoba, Danville, CA (US); Hassan Madani, Seattle, WA (US); Michael Tsang, San Francisco, CA (US); Mark E. Gustafson, St. Charles, MI (US); Gary S. Bild, Chesterfield, MI (US); Gary V. Johnson, St. Charles, MI (US)

(73) Assignees: Chiron Corporation, Emeryville, CA (US); G. D. Searle, LLC, St. Louis, MO (US)

( * ) Notice: Subject to any disclaimer, the term of this patent is extended or adjusted under 35 U.S.C. 154(b) by 386 days.

(21) Appl. No.: 09/996,588

(22) Filed: Nov. 30, 2001

(65) Prior Publication Data

US 2002/0137884 A1    Sep. 26, 2002

Related U.S. Application Data

(60) Continuation of application No. 09/443,099, filed on Nov. 18, 1999, now abandoned, which is a division of application No. 09/973,211, filed as application No. PCT/US96/09980 on Jun. 7, 1996, now Pat. No. 6,323,326, which is a continuation-in-part of application No. 08/473,668, filed on Jun. 7, 1995, now abandoned, which is a continuation-in-part of application No. 08/477,677, filed on Jun. 7, 1995, now abandoned.

(51) Int. Cl.
*A61K 38/00* (2006.01)
*C07K 14/00* (2006.01)

(52) U.S. Cl. ............... 514/12; 514/2; 514/8; 514/21; 514/970; 514/973; 530/350; 530/395

(58) Field of Classification Search ............... 530/350, 530/380, 381, 395; 514/2, 8, 12, 21, 970, 514/973
See application file for complete search history.

(56) References Cited

U.S. PATENT DOCUMENTS

| 4,637,834 A | 1/1987 | Thurow |
| 5,051,497 A | 9/1991 | Fanning et al. |
| 5,212,091 A | 5/1993 | Diaz-Collier et al. ...... 435/69.6 |
| 5,276,015 A | 1/1994 | Khouri et al. |
| 5,276,016 A | 1/1994 | Khouri et al. |
| 5,358,708 A | 10/1994 | Patel |
| 5,466,893 A | 11/1995 | Nakatani ............... 174/261 |
| 5,503,827 A | 4/1996 | Woog et al. |
| 6,103,500 A * | 8/2000 | Innis et al. ............... 435/69.7 |
| 6,323,326 B1 * | 11/2001 | Dorin et al. ............... 530/412 |

FOREIGN PATENT DOCUMENTS

| EP | 0 131 864 | 1/1985 |
| EP | 0 325 691 | 8/1989 |
| EP | 0473 564 A1 | 3/1992 |
| EP | 0 559 632 A2 | 9/1993 |
| EP | 0 559 832 A2 | 9/1993 |
| WO | WO-93/25230 A1 * | 12/1993 |
| WO | WO 93/25230 A1 | 12/1993 |

OTHER PUBLICATIONS

Rainer Rudolph, "Successful Protein Folding on a Industrial Scale", Protein Engineering: Principles and Practice, Chapter 10, pps. 283-298, dated 1998.

Rudolph & Lillie, "In vitro folding of Inclusion body proteins", Folding of Acidic Fibroblast Growth Factor, FASEB J., 10, pps. 49-56, date unknown.

Dabora et al., "Effect of Polyanions on the Refolding of Human Acidic Fibroblast Growth Factor", The Journal Of Biological Chemistry, vol. 266, No. 35, pps. 23637-23840, dated Dec. 15, 1991.

Bernhard Fisher et al., Isolation, Renaturation, and Formation of Disulfide Bonds of Eukaryotic Proteins Expressed in *Escherichia coli* as Inclusion Bodies, Biotechnology and Bioengineering, vol. 41, pps. 3-13, dated 1993.

J. Harenberg, et al., Tissue factor pathway Inhibotor: proposed heparin recognition region, Blood Coagulation and Fibrinolysis, vol. 6, Supp. No. 1, pps. S50-S56, dated 1995.

Mark E. Gustafson et al., Renaturation and Purification of Human Tissue Factor Pathway Inhibitor Expressed in Recombinant *E. coli*, Protein Expression and Purification, vol. 5, pps. 233-241, dated 1994.

* cited by examiner

*Primary Examiner*—Jon Weber
*Assistant Examiner*—Rita Mitra
(74) *Attorney, Agent, or Firm*—Benjamin C. Spehlmann; Lisa M. Hemmendinger; Alisa A. Harbin

(57) ABSTRACT

A method of modifying protein solubility employs polyionic polymers. These facilitate the solubilization, formulation, purification and refolding of proteins especially incorrectly folded proteins and aggregated proteins. Compositions are described that are suitable for formulating TFPI. The compositions allow preparation of pharmaceutically acceptable compositions of TFPI at concentrations above 0.2 mg/mL and above 10 mg/mL.

85 Claims, 34 Drawing Sheets

TFPI Peak Fractions from
Phenyl Sepharose HIC

Load

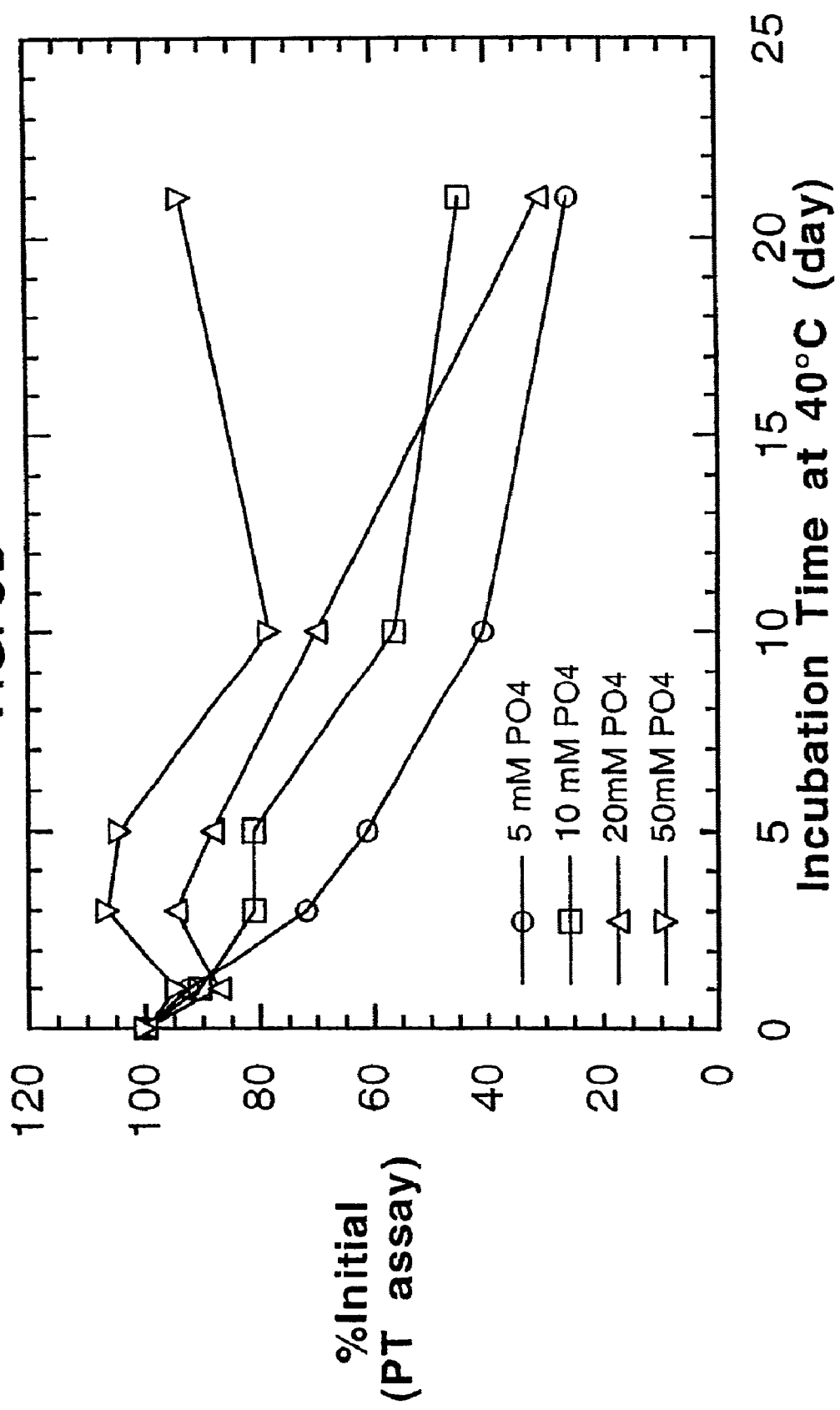

FIG. 13
ph  4  5  6  7  8  9
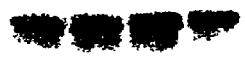
t = 20 day
at 40°C                        ← Monomer TFPI
                               ← Cleared species
                               ←
t = 0              ← Monomer TFPI Non-reducing SDS-PAGE analysis of polyphosphate refold timepoints

| Lane # | Lane Description |
|---|---|
| 1 | Dissolved refractile bodies |
| 2 | $T_{1\,hour}$ |
| 3 | $T_{18\,hour}$ |
| 4 | $T_{21\,hour}$ |
| 5 | $T_{25\,hour}$ |
| 6 | $T_{43\,hour}$ |
| 7 | $T_{66\,hour}$ |
| 8 | $T_{90\,hour}$ |
| 9 | $T_{95\,hour}$ |
| 10 | SC-59735 |

Non-reducing SDS-PAGE analysis of SP-Sepharose fractions

| Lane # | Lane Description |
|---|---|
| 1 | Fraction 25 |
| 2 | Fraction 27 |
| 3 | Fraction 29 |
| 4 | Fraction 31 |
| 5 | Fraction 33 |
| 6 | Fraction 35 |
| 7 | Fraction 37 |
| 8 | Fraction 39 |
| 9 | 1.0M elution |
| 10 | SC-59735 |

FIG. 17
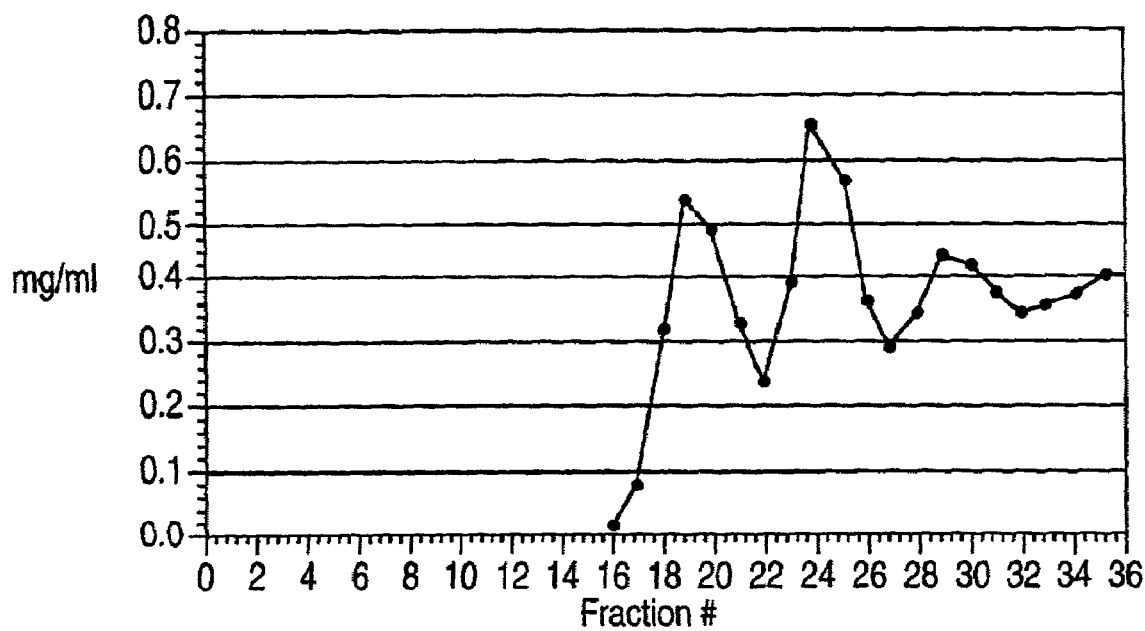
Q-Sepharose elution profile for polyphosphate refold
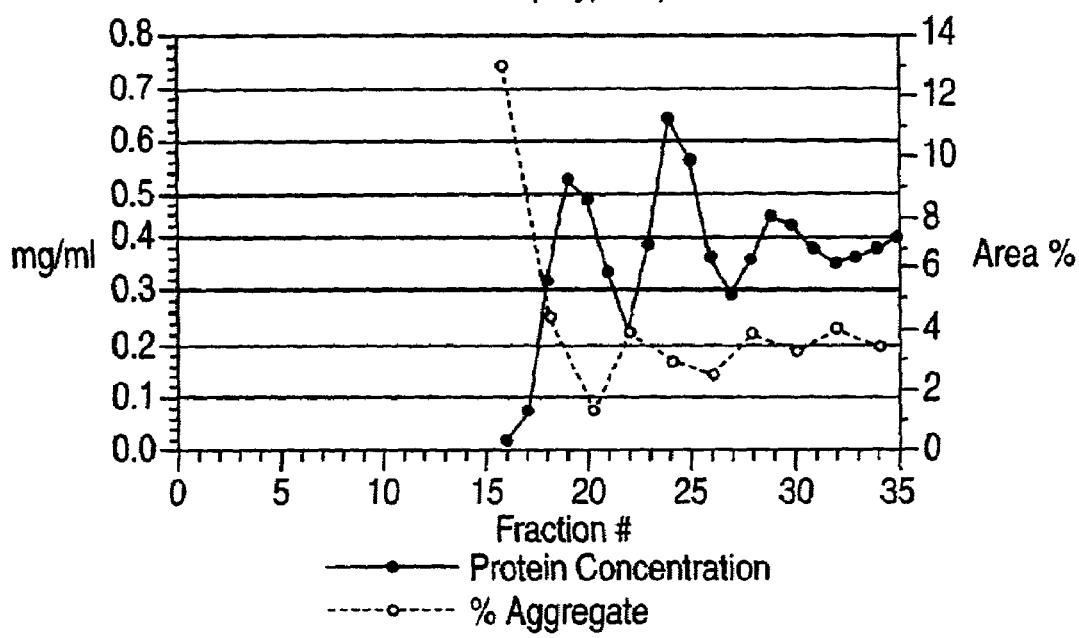
Aggregate content of Q-Sepharose fractions from 100 liter polyphosphate refold Non-reducing SDS-PAGE analysis of Q-Sepharose fractions.

| Lane # | Lane Description |
|---|---|
| 1 | Molecular Weight Markers |
| 2 | |
| 3 | Fraction 20 |
| 4 | Fraction 21 |
| 5 | Fraction 22 |
| 6 | Fraction 23 |
| 7 | Fraction 24 |
| 8 | SC-59735 |
| 9 | |
| 10 | |

Non-reducing SDS-PAGE analysis PEI refold timepoints.

| Lane # | Lane Description |
|---|---|
| 1 | |
| 2 | Molecular Weight Markers |
| 3 | |
| 4 | $T_{0\ hour}$ |
| 5 | $T_{1\ hour\ +\ cysteine}$ |
| 6 | $T_{20\ hour}$ |
| 7 | $T_{48\ hour}$ |
| 8 | $T_{96\ hour}$ |
| 9 | SC-59735 |
| 10 | |

FIG. 22
Protein Concentration Profiles of Q Sepharose Elution
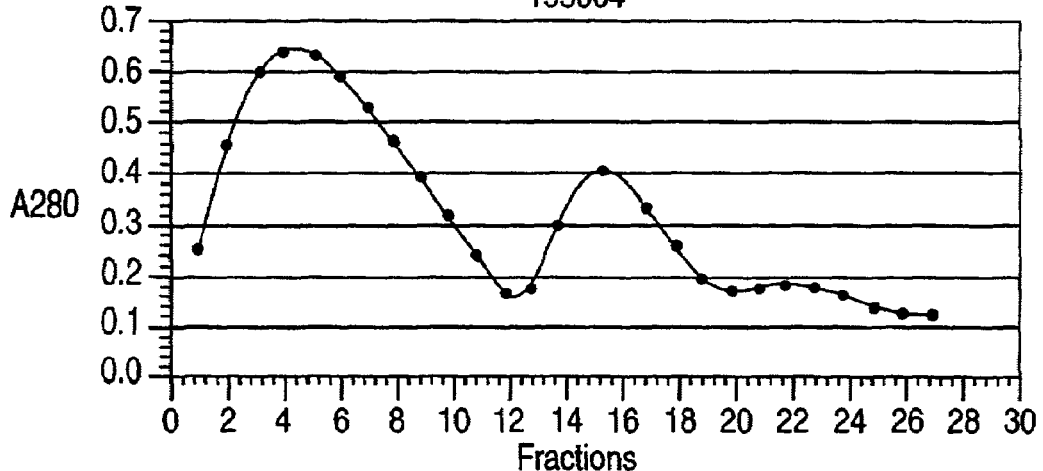
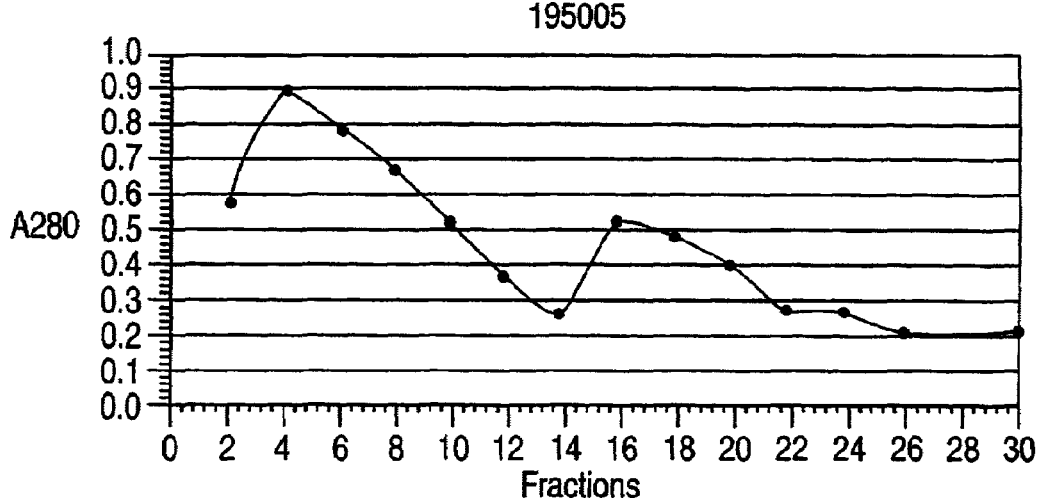
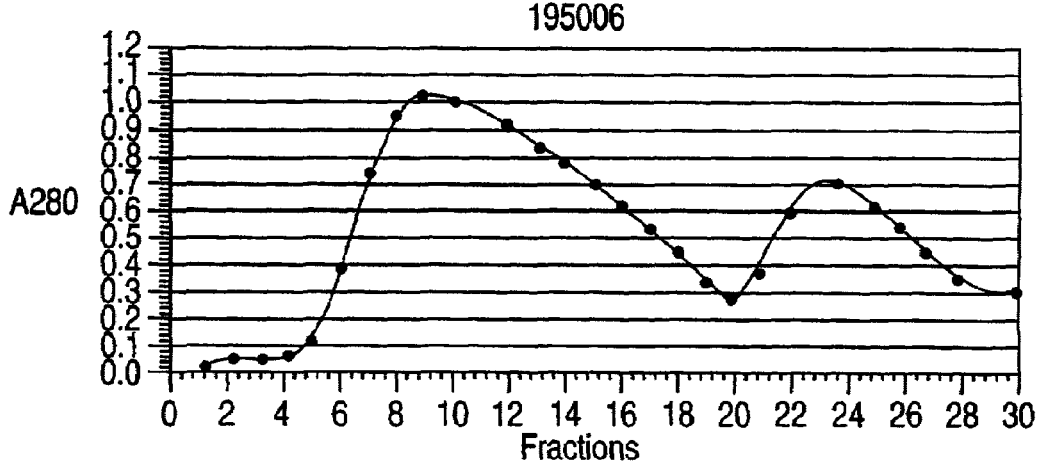

Non-reducing SDS-PAGE analysis of Q-Sepharose fractions from run #I95005.

| Lane # | Lane Description |
|---|---|
| 1 | Molecular Weight Markers |
| 2 | |
| 3 | Fraction 24 |
| 4 | Fraction 25 |
| 5 | Fraction 26 |
| 6 | Fraction 27 |
| 7 | Fraction 28 |
| 8 | Fraction 29 |
| 9 | Fraction 30 |
| 10 | SC-59735 |

Results of SC-59735 refolding in water with 0.4% polyphosphate.

Results from experiment evaluating the impact of different polyphosphate chain lengths on SC-59735 refolding.

Chain length evaluation expressed as PT.

Effects of high concentrations of polyphosphate on SC59735 refold.

Effects of low polyphosphate concentrations on SC-59735 refolds.

Mono-S Analysis of Refolded TFPI

Refolding Yields: 30-40%   15-20%

FORMULATION, SOLUBILIZATION, PURIFICATION, AND REFOLDING OF TISSUE FACTOR PATHWAY INHIBITOR

This application is a continuation of U.S. Ser. No. 09/443,099, filed Nov. 18, 1999 now abandoned, which is a divisional of U.S. Ser. No. 08/973,211, filed Jun. 11, 1999, now U.S. Pat. No. 6,323,326, which is an application based on PCT/US96/09980, filed Jun. 7, 1996, which is a continuation-in-part of U.S. Ser. No. 08/473,668, filed Jun. 7, 1995, now abandoned, which is a continuation-in-part of U.S. Ser. No. 08/477,677, filed Jun. 7, 1995, now abandoned.

TECHNICAL FIELD OF THE INVENTION

The invention relates to methods useful for refolding, solubilizing, formulating and purifying proteins. These methods are particularly useful for proteins that have been engineered by genetic recombination and produced in bacterial, yeast or other cells in a form that has a non-native tertiary structure.

BACKGROUND OF THE INVENTION

To understand fully the entire process of gene expression, it is as important to understand the process for the folding of the peptide chain into a biologically active protein as it is important to understand the synthesis of the primary sequence. The biological activities of proteins depend not only on their amino acid sequences but also on the discrete conformations of the proteins concerned, and slight disturbances to the conformational integrity of a protein can destroy its activity. Tsou et al. (1988) *Biochemistry* 27:1809–1812.

Under the proper conditions, the in vitro refolding of purified, denatured proteins to achieve the native secondary and tertiary structure is a spontaneous process. To avoid formation of stable, but undesired, structures, it is necessary to use the tertiary interactions (which are formed late in folding) with their high degree of selectivity power to select and further stabilize those early local structures that are on the correct folding pathway. Thus, the finite, but very low, stability of local structures could be the kinetic "proofreading" mechanism of protein folding. The activated state of folding with the highest energy is a distorted form of the native protein, and the slowest, rate-limiting step of unfolding and refolding appears to be close to the native state in terms of ordered structure. In addition, the refolding of many proteins is not completely reversible in vitro, and reactivation yields of less than 100% are frequently observed, which holds true in particular for experiments at high protein concentration, and competing aggregation of unfolded or partially refolded protein molecules may be the major reason for a lowered reversibility, as described in Fischer and Schmid, (1990) *Biochemistry* 29:2205–2212.

In the case of sufficiently large protein molecules, the nascent polypeptide chain acquires its native three-dimensional structure by the modular assembly of micro-domains. Variables including temperature, and cosolvents such as polyols, urea, and guanidinium chloride, have been tested to determine their role in stabilizing and destabilizing protein conformations. The action of cosolvents may be the result of direct binding or the alterations of the physical properties of water, as described in Jaenicke et al. (1991) *Biochemistry* 30 (13):3147–3161.

Experimental observations of how unfolded proteins refold to their native three-dimensional structures contrast with many popular theories of protein folding mechanisms. Under conditions which allow for refolding, unfolded protein molecules rapidly equilibrate between different conformations prior to complete refolding. The rapid prefolding equilibrium favors certain compact conformations that have somewhat lower free energies than the other unfolded conformations. The rate-limiting step occurs late in the pathway and involves a high-energy, distorted form of the native conformation. There appears to be a single transition through which essentially all molecules fold, as described in Creighton et al. (1988) *Proc. Nat. Acad Sci. USA* 85:5082–5086.

Various methods of refolding of purified, recombinantly produced proteins have been used. For example, the protease encoded by the human immunodeficiency virus type I (HIV-I) can be produced in *Escherichia coli*, yielding inclusion bodies harboring the recombinant HIV-I protease as described by Hui et al. (1993) *J. Prot. Chem.* 12: 323–327. The purified HIV-I protease was refolded into an active enzyme by diluting a solution of the protein in 50% acetic acid with 25 volumes of buffer at pH 5.5. It was found that a higher specific activity of protease was obtained if the purified protein was dissolved at approximately 2 mg/ml in 50% acetic acid followed by dilution with 25 volumes of cold 0.1 M sodium acetate, pH 5.5, containing 5% ethylene glycol and 10% glycerol. Exclusion of glycerol and ethylene glycol led to gradual loss of protein due to precipitation. About 85 mg of correctly folded HIV-I protease per liter of *E. coil* cell culture was obtained by this method, and the enzyme had a high specific activity.

Another example of refolding a recombinant protein is the isolation and refolding of H-ras from inclusion bodies of *E. coli* as described by DeLoskey et. al. (1994) *Arch. Biochem. and Biophys.* 311:72–78. In this study, protein concentration, temperature, and the presence of 10% glycerol were varied during refolding. The yield of correctly folded H-ras was highest when the protein was refolded at concentrations less than or equal 0.1 mg/ml and was independent of the presence of 10% glycerol. The yield was slightly higher at 4° than at 25° C.

The refolding of Tissue Factor Pathway inhibitor (also known variously as Lipoprotein-Associated Coagulation Ihibitor (LACI), Extrinsic Pathway Inhibitor (EPI) and Tissue Factor Inhibitor (EFI) and hereinafter referred to as "TFPI") produced in a bacterial expression system has been described by Gustafson et al. (1994) *Protein Expression and Purification* 5: 233–241. In this study, high level expression of TFPI in recombinant *E. coli* resulted in the accumulation of TFPI in inclusion bodies. Active protein was produced by solubilization of the inclusion bodies in 8M urea, and purification of the full-length molecule was achieved by cation exchange chromatography and renaturation in 6M urea. The refolded mixture was then fractionated to yield a purified nonglycosylated TFPI possessing in vitro biological activity as measure in the Prothombin clotting time assay comparable to TFPI purified from mammalian cells.

A non-glycosylated form of TFPI has also been produced and isolated from *Escherichia coli* (*E. coli*) cells as disclosed in U.S. Pat. No. 5,212,091, the disclosure of which is herein incorporated by reference. The invention described in U.S. Pat. No. 5,212,091 subjected the inclusion bodies containing TFPI to sulfitolysis to form TFPI-S-sulfonate, purified TFPI-S-sulfonate by anion exchange chromatography, refolded TFPI-S-sulfonate by disulfide exchange using cysteine and purified active TFPI by cation exchange chromatography. The form of TFPI described in U.S. Pat. No. 5,212,091 has been shown to be active in the inhibition of bovine factor Xa and in the inhibition of human tissue factor-induced coagulation in plasma. In some assays, the *E. coli*-produced TFPI has been shown to be more active than native TFPI derived from SK hepatoma cells. However, TFPI produced in *E. coli* cells is modified in ways that increase heterogeneity of the protein.

A need exists in the art of refolding recombinantly produced proteins to increase the amount of correctly folded TFPI during the refolding process. A need also exists for increasing the solubility of TFPI. Presently the yields of recombinantly produced TFPI have been lower than desirable, and a need exists in the art of producing correctly folded TFPI. See for example Gustafuson et al. (1994) *Protein Expression and Purification* 5: 233–241.

TFPI inhibits the coagulation cascade in at least two ways: preventing formation of factor VIIa/tissue factor complex and by binding to the active site of factor Xa. The primary sequence of TFPI, deduced from cDNA sequence, indicates that the protein contains three Kunitz-type enzyme inhibitor domains. The first of these domains is required for the inhibition of the factor VIIa/tissue factor complex. The second Kunitz-type domain is needed for the inhibition of factor Xa. The function of the third Kunitz-type domain is unknown. TFPI has no known enzymatic activity and is thought to inhibit its protease targets in a stoichiometric manner, namely, binding of one TFPI Kunitz-type domain to the active site of one protease molecule. The carboxy-terminal end of TFPI is believed to have a role in cell surface localization via heparin binding and by interaction with phospholipid. TFPI is also known as Lipoprotein Associated Coagulation Inhibitor (LACI), Tissue Factor Inhibitor (TFI), and Extrinsic Pathway Inhibitor (EPI).

Mature TFPI is 276 amino acids in length with a negatively charged amino terminal end and a positively charged carboxy-terminal end. TFPI contains 18 cysteine residues and forms 9 disulphide bridges when correctly folded. The primary sequence also contains three Asn-X-Ser/Thr N-linked glycosylation consensus sites, the asparagine residues located at positions 145, 195 and 256. The carbohydrate component of mature TFPI is approximately 30% of the mass of the protein However, data from proteolytic mapping and mass spectral data imply that the carbohydrate moieties are heterogeneous. TFPI is also found to be phosphorylated at the serine residue in position 2 of the protein to varying degrees. The phosphorylation does not appear to affect TFPI function.

TFPI has been isolated from human plasma and from human tissue culture cells including HepG2, Chang liver and SK hepatoma cells. Recombinant TFPI has been expressed in mouse C127 cells, baby hamster kidney cells, Chinese hamster ovary cells and human SK hepatoma cells. Recombinant TFPI from the mouse C127 cells has been shown in animal models to inhibit tissue-factor induced coagulation.

A non-glycosylated form of recombinant TFPI has been produced and isolated from *Escherichia coli* (*E. coli*) cells as disclosed in U.S. Pat. No. 5,212,091. This form of TFPI has been shown to be active in the inhibition of bovine factor Xa and in the inhibition of human tissue factor-induced coagulation in plasma. Methods have also been disclosed for purification of TFPI from yeast cell culture medium, such as in Petersen et al, *J. Biol. Chem.* 18:13344–13351 (1993).

Recently, another protein with a high degree of structural identity to TFPI has been identified. Sprecher et al, *Proc. Nat. Acad. Sci.*, USA 91:3353–3357 (1994). The predicted secondary structure of this protein, called TFPI-2, is virtually identical to TFPI with 3 Kunitz-type domains, 9 cysteine-cysteine linkages, an acidic amino terminus and a basic carboxy-terminal tail. The three Kunitz-type domains of TFPI-2 exhibit 43%, 35% and 53% primary sequence identity with TFPI Kunitz-type domains 1, 2, and 3, respectively. Recombinant TFPI-2 strongly inhibits the amidolytic activity of factor VIIa/tissue factor. By contrast, TFPI-2 is a weak inhibitor of factor Xa amidoltic activity.

TFPI has been shown to prevent mortality in a lethal *Escherichia coli* (*E. coil*) septic shock baboon model. Creasey el al, *J. Clin. Invest.* 91:2850–2860 (1993). Administration of TFPI at 6 mg/kg body weight shortly after infusion of a lethal dose of *E. coli* resulted in survival in all five TFPI-treated animals with significant improvement in quality of life compared with a mean survival time for the five control animals of 39.9 hours. The administration of TFPI also resulted in significant attenuation of the coagulation response, of various measures of cell injury and significant reduction in pathology normally observed in *E. coli* sepsis target organs, including kidneys, adrenal glands, and lungs.

Due to its clot-inhibiting properties, TFPI may also be used to prevent thrombosis during microvascular surgery. For example, U.S. Pat. No. 5,276,015 discloses the use of TFPI in a method for reducing thrombogenicity of microvascular anastomoses wherein TFPI is administered at the site of the microvascular anastomoses contemporaneously with microvascular reconstruction.

TFPI is a hydrophobic protein and as such, has very limited solubility in aqueous solutions. This limited solubility has made the preparation of pharmaceutically acceptable formulations of TFPI difficult to manufacture, especially for clinical indications which may benefit from administration of high doses of TFPI. Thus, a need exists in the art for pharmaceutically acceptable compositions containing concentrations of TFPI which can be administered to patients in acceptable amounts.

Kinetic rate constant for the remaining soluble TFPI was analyzed by following decrease of the main peak on cation exchange chromatograms.

FIG. 9 shows the percentage of remaining soluble TFPI measured by cation exchange HPLC (9A) and remaining active TFPI by prothrombin time assay (9B) as a function of phosphate concentration. The formulation contains 150 μg/mL TFPI prepared in 150 mM NaCl and 0.005% (w/v) polysorbate-80 at pH 7 with varying concentrations of phosphate.

Figure 10:
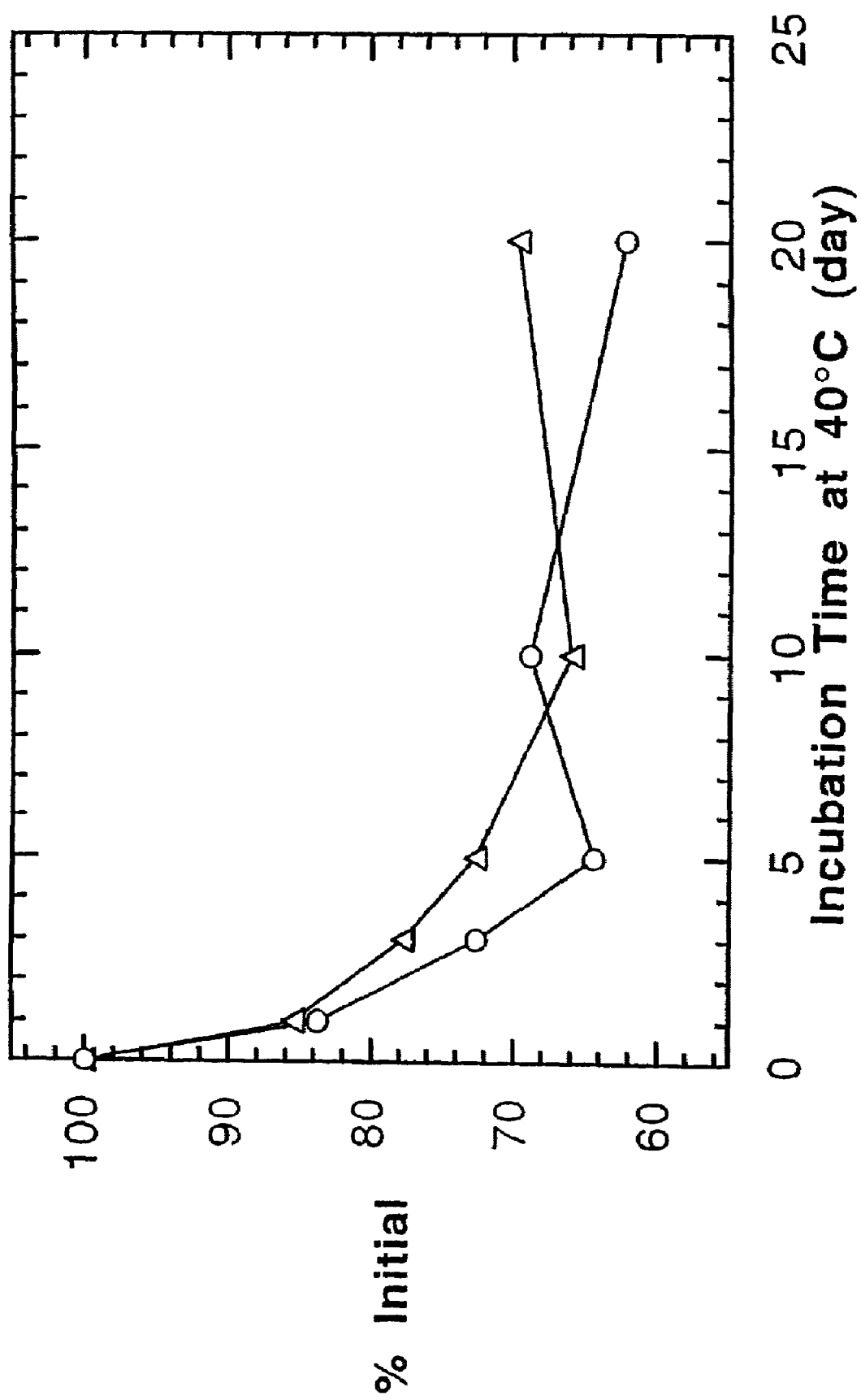

FIG. 10 shows loss of soluble TFPI at 40° C. measured by both cation-exchange HPLC (triangle) and prothrombin time assay (circle) for 0.5 mg/mL TFPI formulated in 10 mM Na citrate, pH 6 and 150 mM NaCl.

Figure 11:
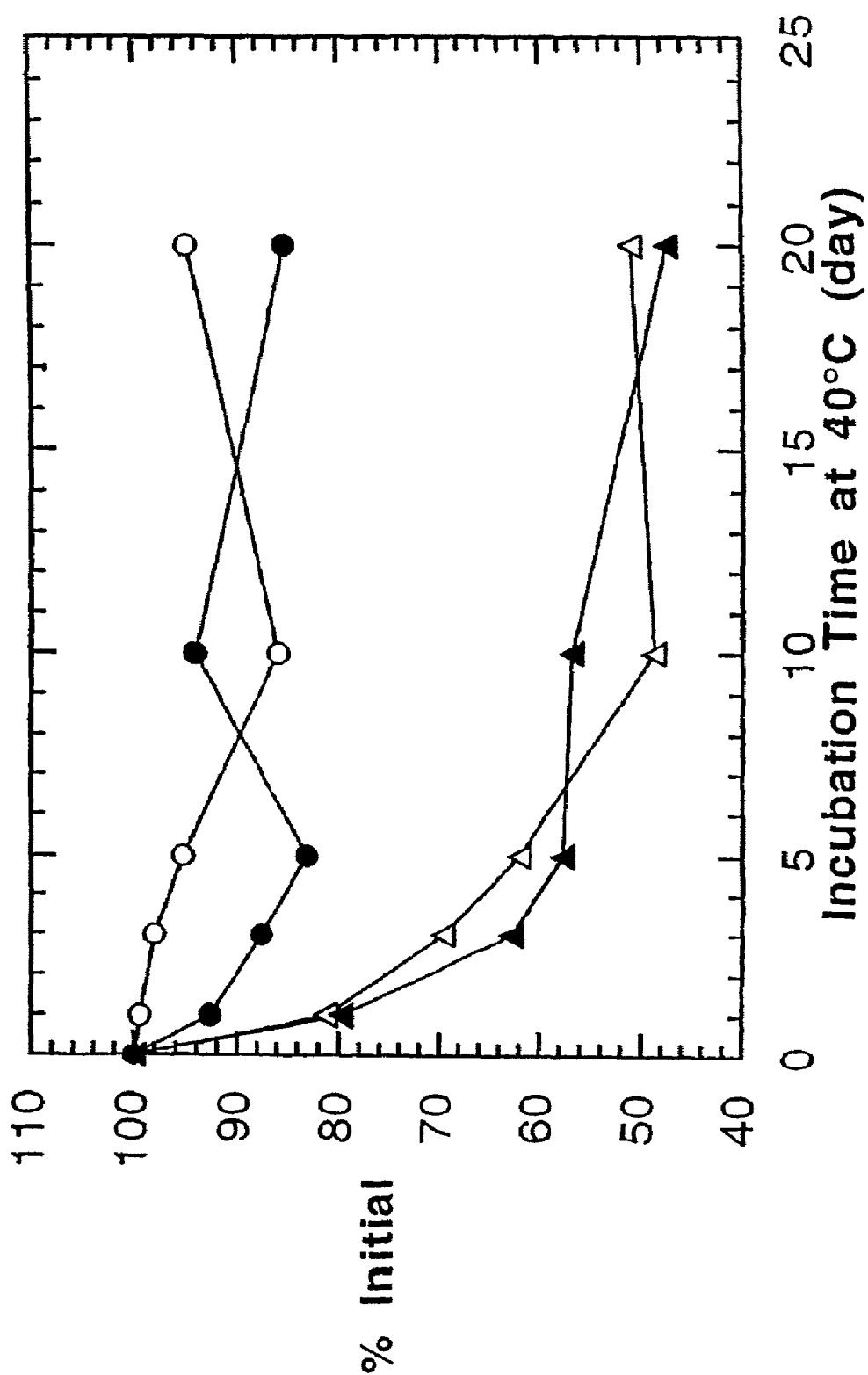

FIG. 11 shows loss of soluble TFPI at 40° C. measured by both cation-exchange HPLC (open symbol) and prothrombin time assay (closed symbol) for 0.5 mg/mL TFPI formulated in 10 mM Na phosphate, pH 6 and either 150 mM NaCl (triangle) or 500 mM NaCl (circle).

Figure 12:
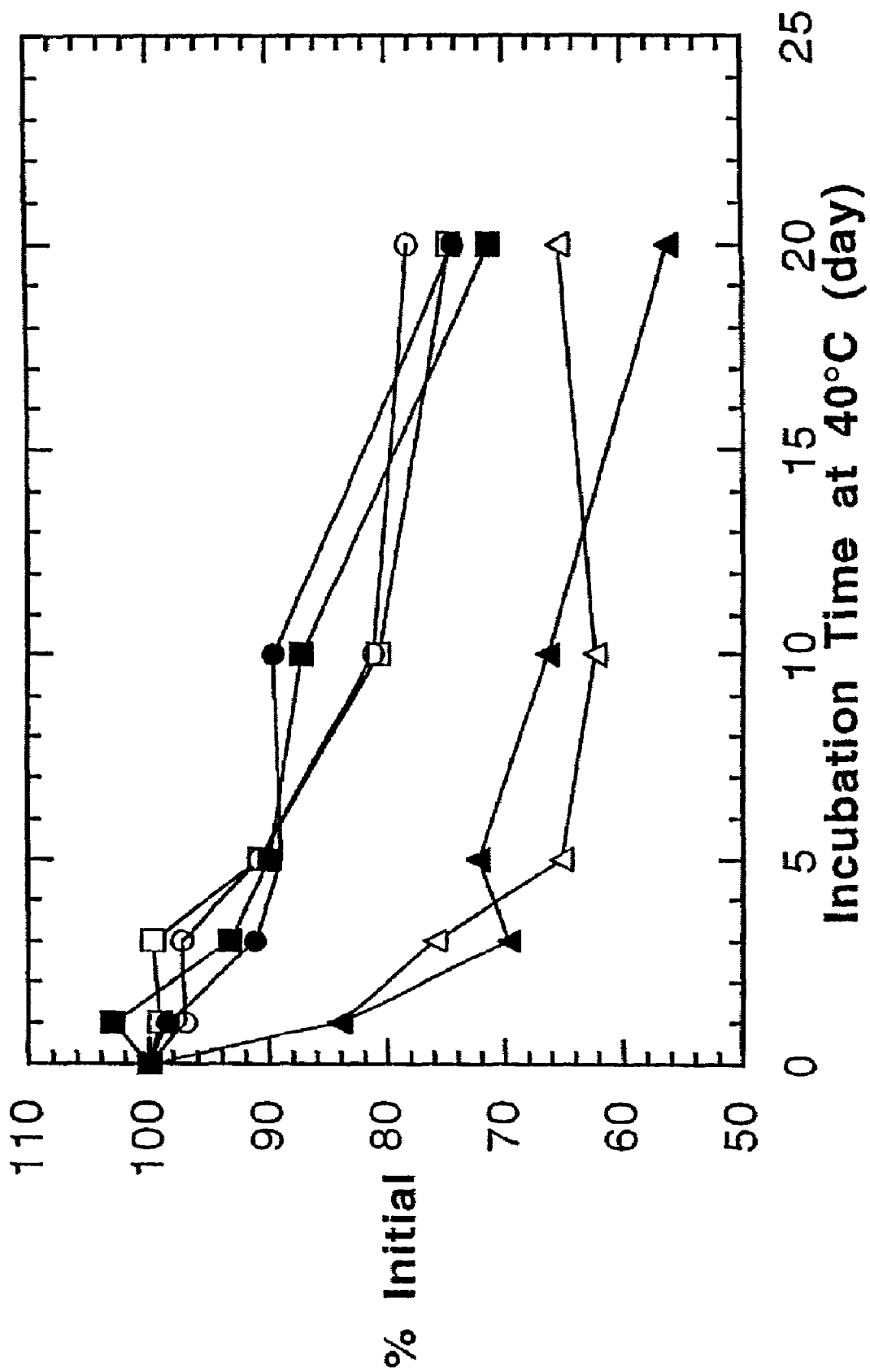

FIG. 12 shows loss of soluble TFPI at 40° C. measured by both cation-exchange HPLC (open symbol) and prothrombin time assay (closed symbol) for 0.5 mg/mL TFPI formulated in 10 mM Na acetate and pH 5.5 containing 150 mM NaCl (triangle) or 8% (w/v) sucrose (square) or 4.5% mannitol (circle).

FIG. 13 shows two non-reducing SDS gels for TFPI formulation samples at pH 4 to 9 stored at 40° C. for 0 and 20 days.

Figure 14:
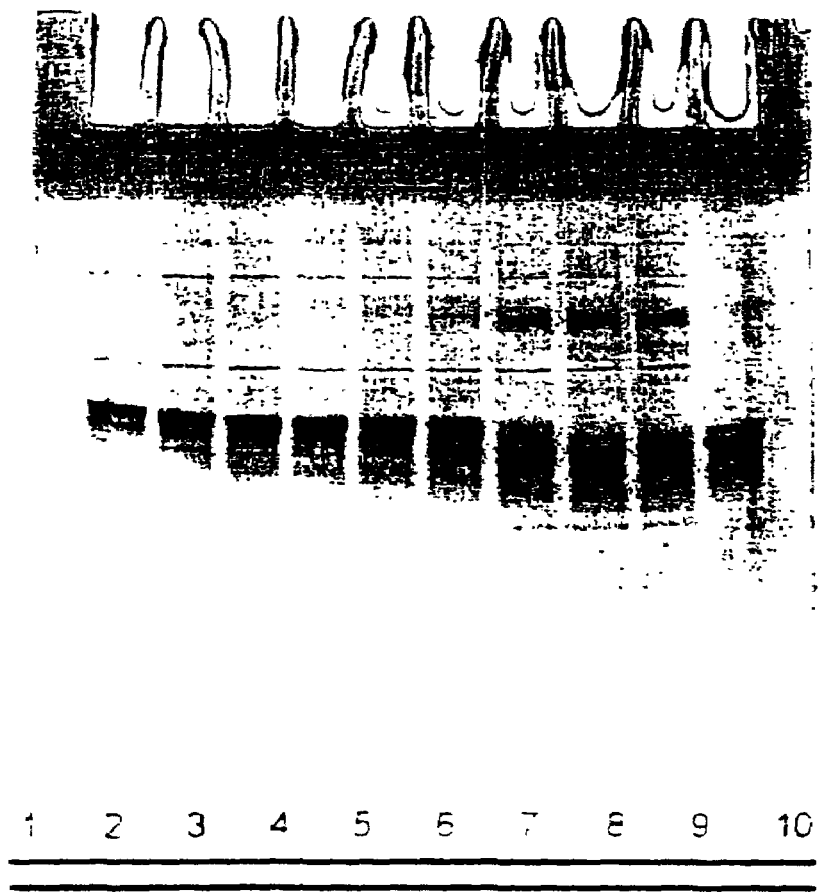

FIG. 14 shows the time course of a polyphosphate-facilitated rhTFPI refold monitored using SDS PAGE.

Figure 15:
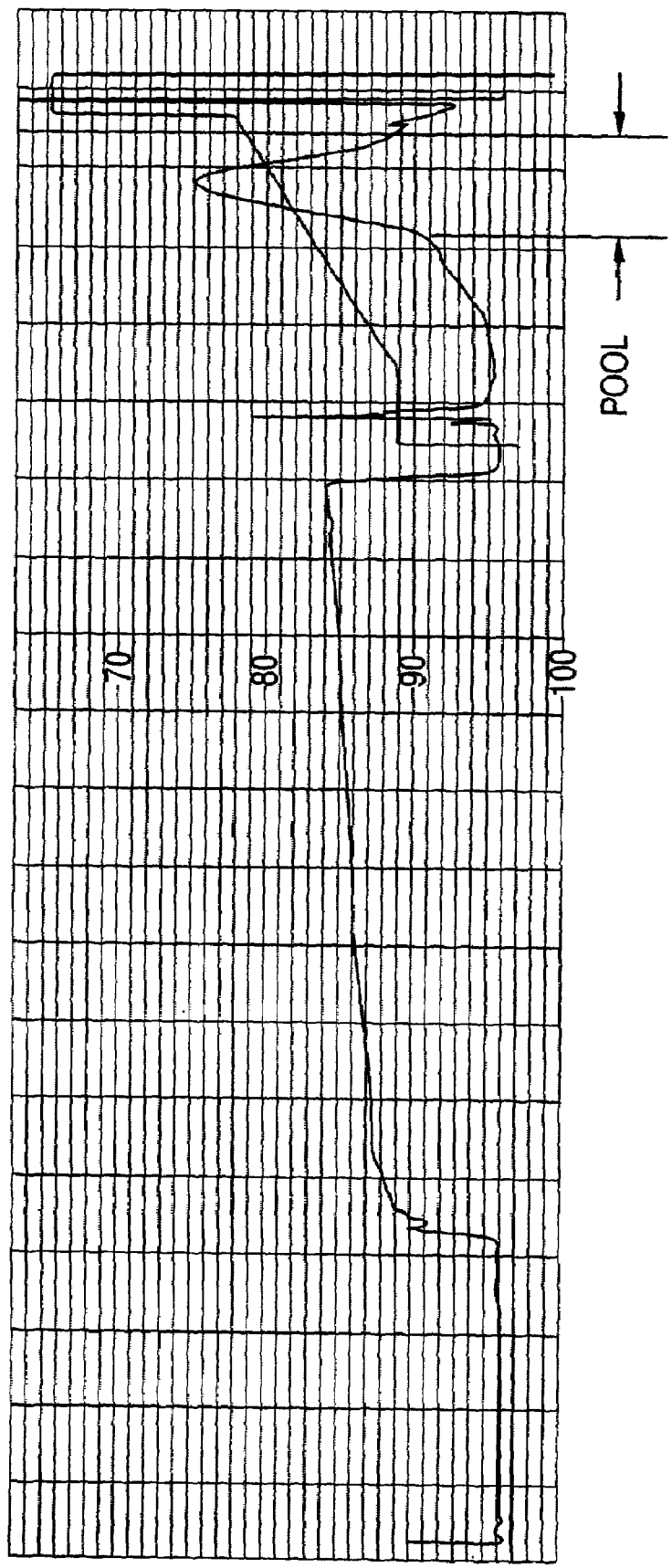

FIG. 15 shows the absorbance at 280 nm during the loading and elution of the S-Sepharose HP column used to purify rhTFPI from a polyphosphate-facilitated refold.

Figure 16A:
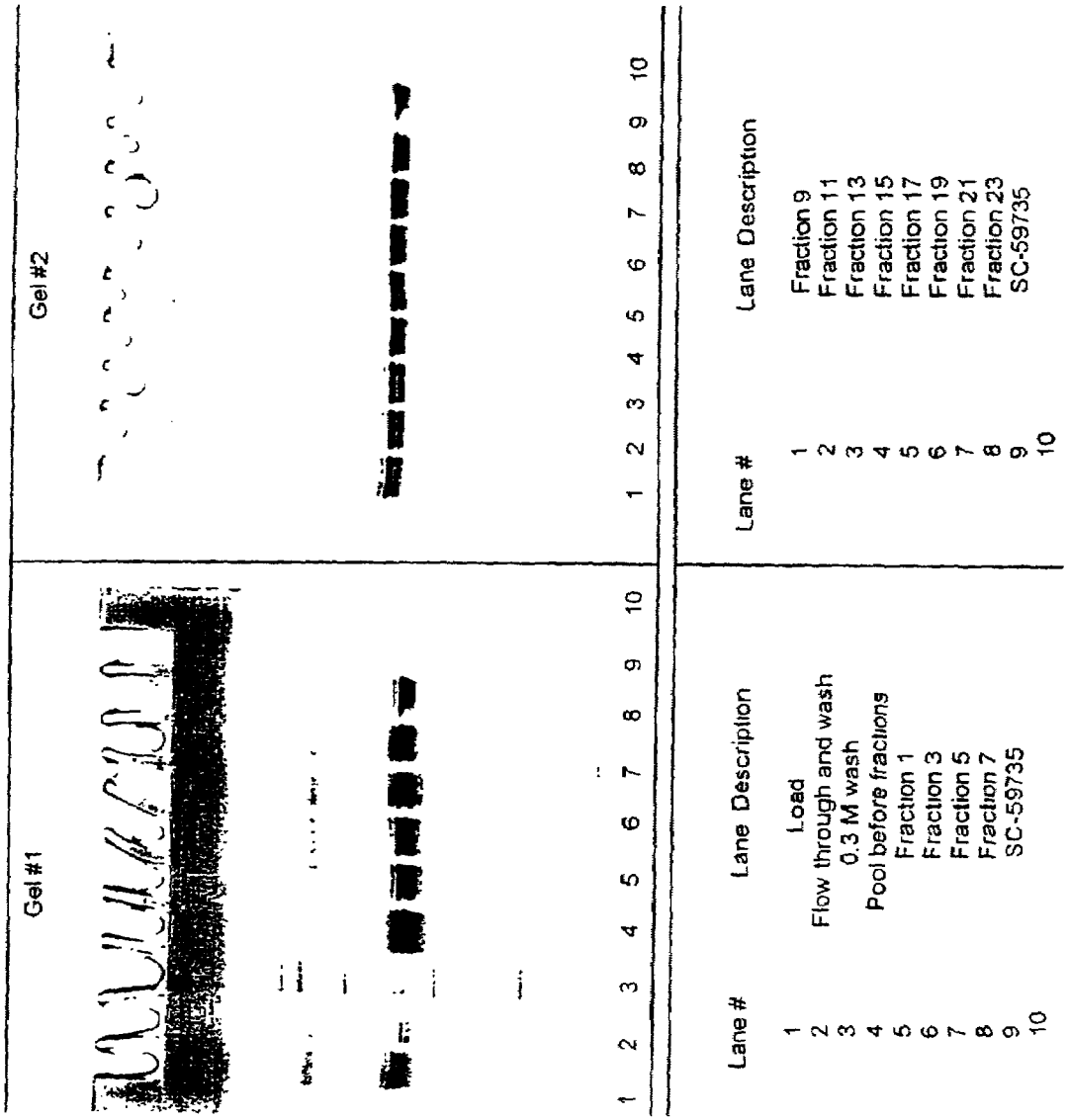
Figure 16B:
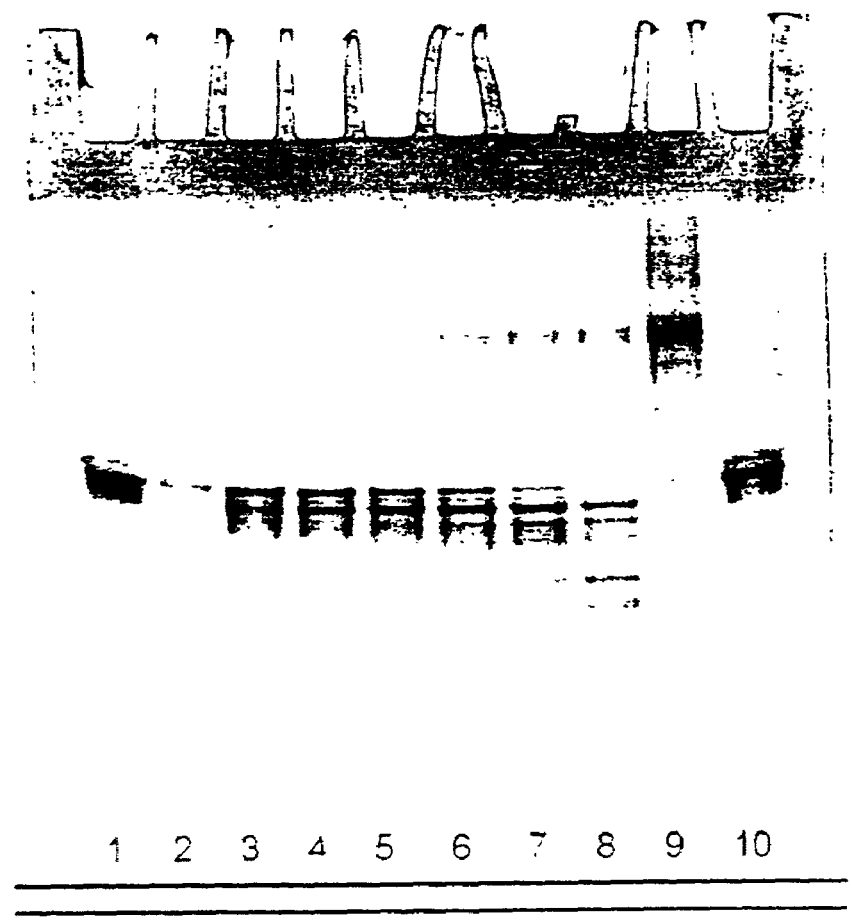

FIG. 16 shows SDS PAGE analysis of fractions collected during elution of the S-Sepharose HP column used to purify rhTFPI from a polyphosphate-facilitated refold. FIG. 16A shows Load through Fraction 23, and FIG. 16B shows Fractions 25–39.

FIG. 17 shows the absorbance at 280 nm during the loading and elution of the Q-Sepharose HP column used to purify rhTFPI from a S-Sepharose pool prepared from a polyphosphate-facilitated refold.

Figure 18A:
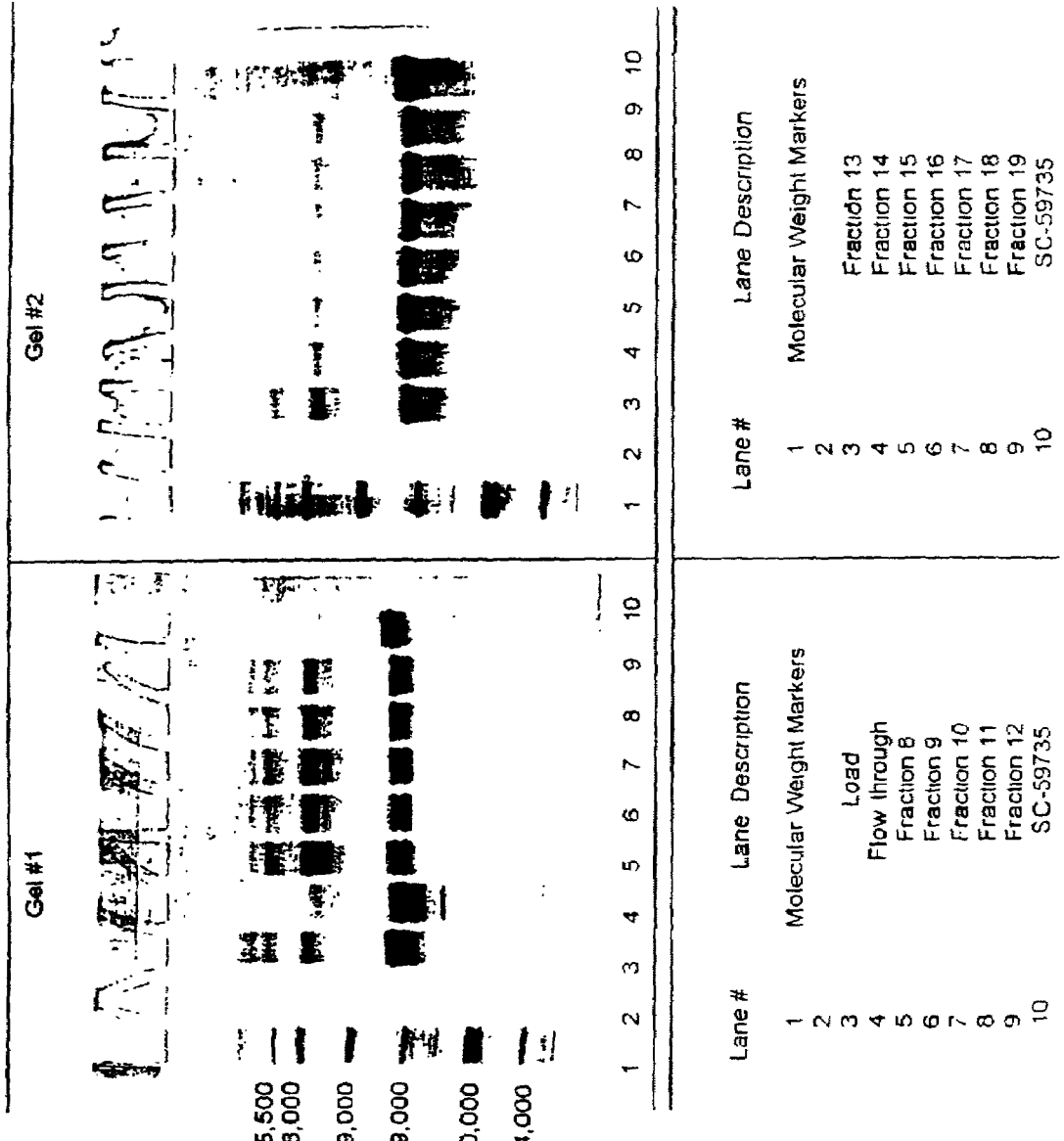
Figure 18B:
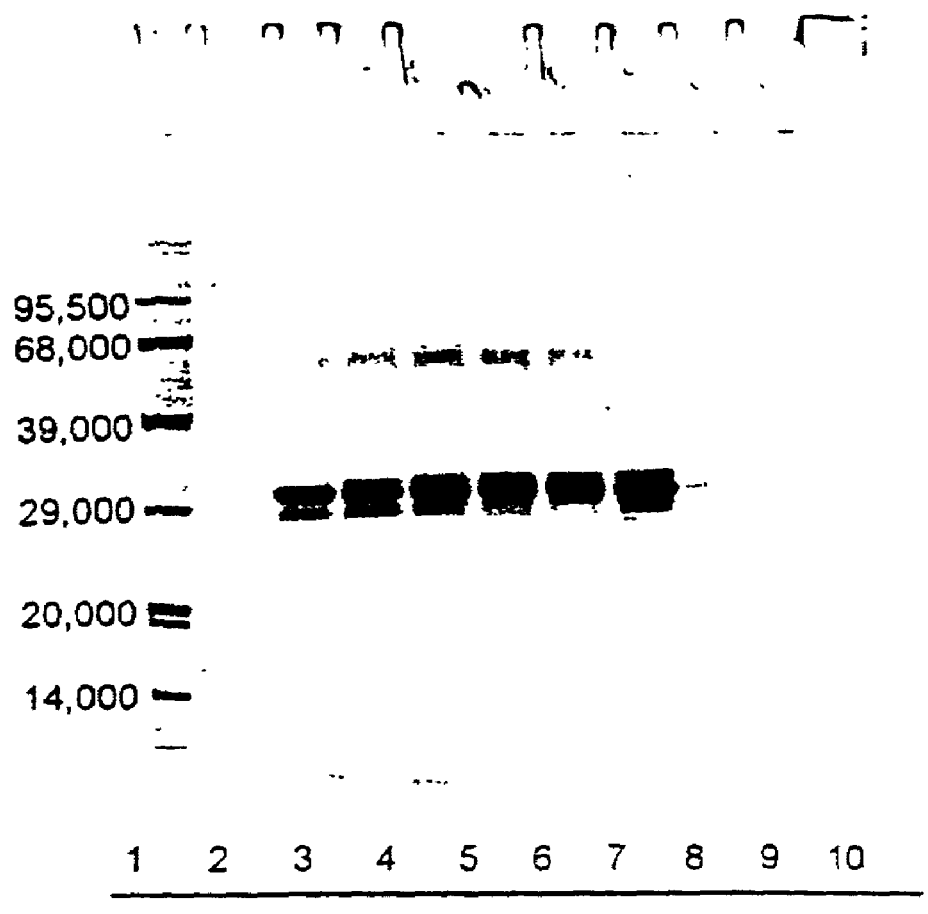

FIG. 18 shows SDS PAGE analysis of fractions collected during elution of the Q-Sepharose HP column used to purify rhTFPI from a S-Sepharose pool prepared from a polyphosphate-facilitated refold. FIG. 18 A shows Load through Fraction 19, and FIG. 18B shows Fractions 20–24.

Figure 19:
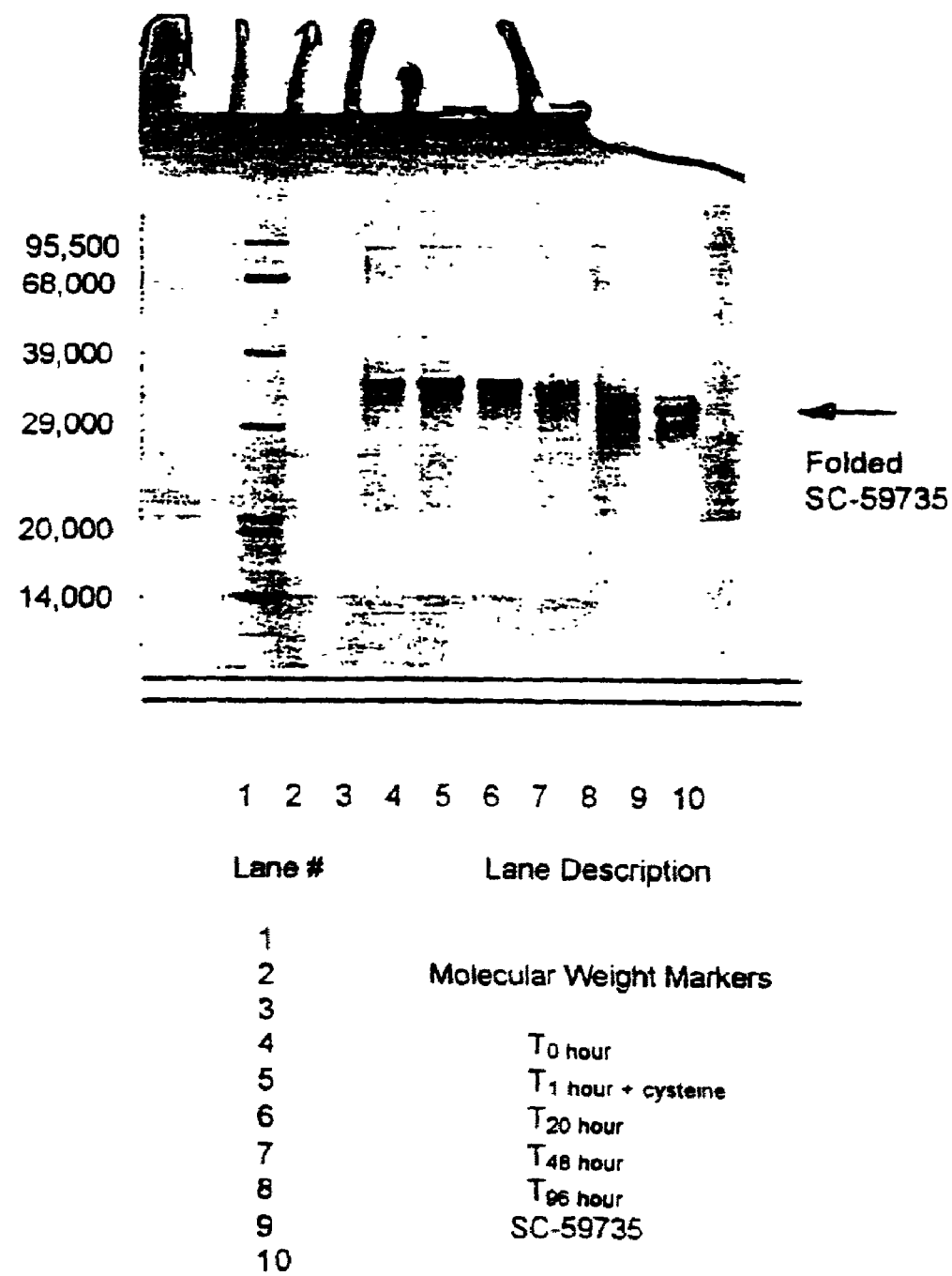

FIG. 19 shows the time course of a polyethyleneimine-facilitated rhTFPI refold monitored using SDS PAGE.

Figure 20:
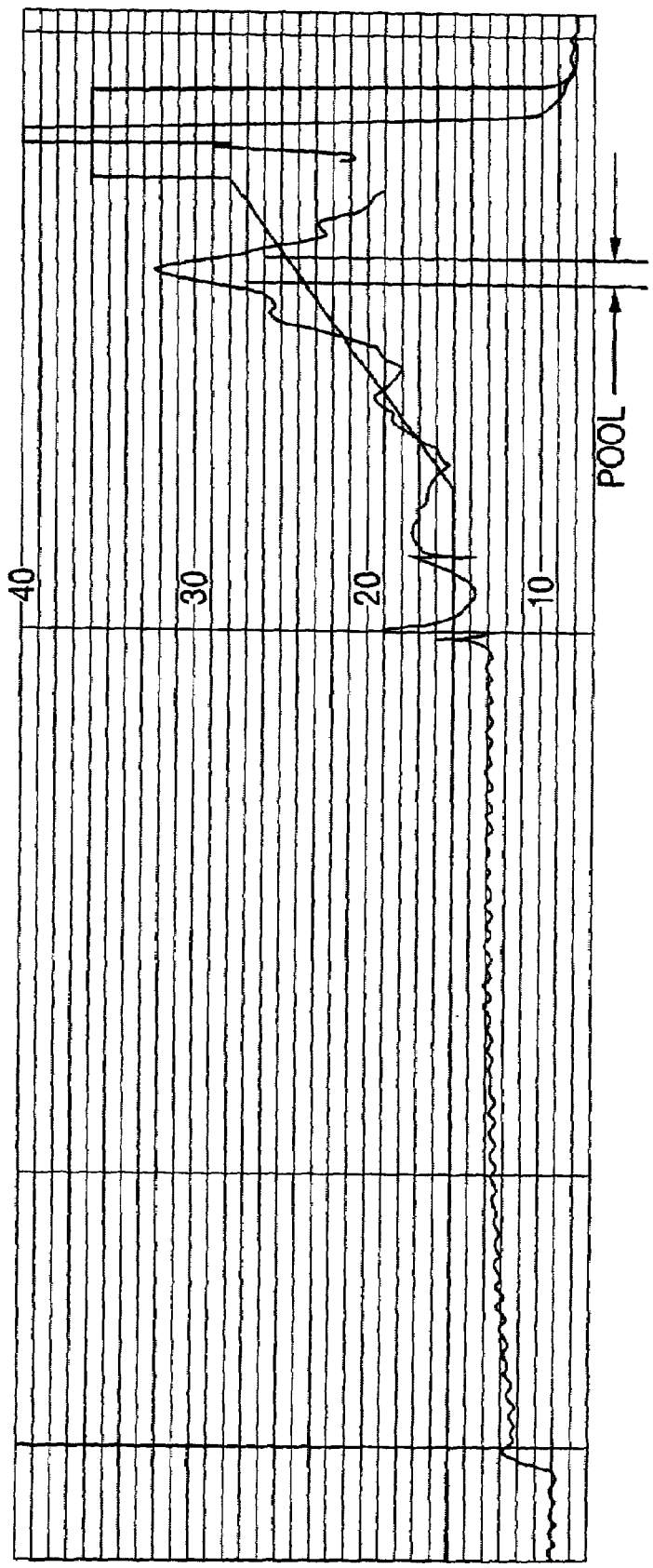

FIG. 20 shows the absorbance at 280 nm during the loading and elution of the S-Sepharose HP column used to purify rhTFPI from a polyethyleneimine-facilitated refold.

Figure 21A:
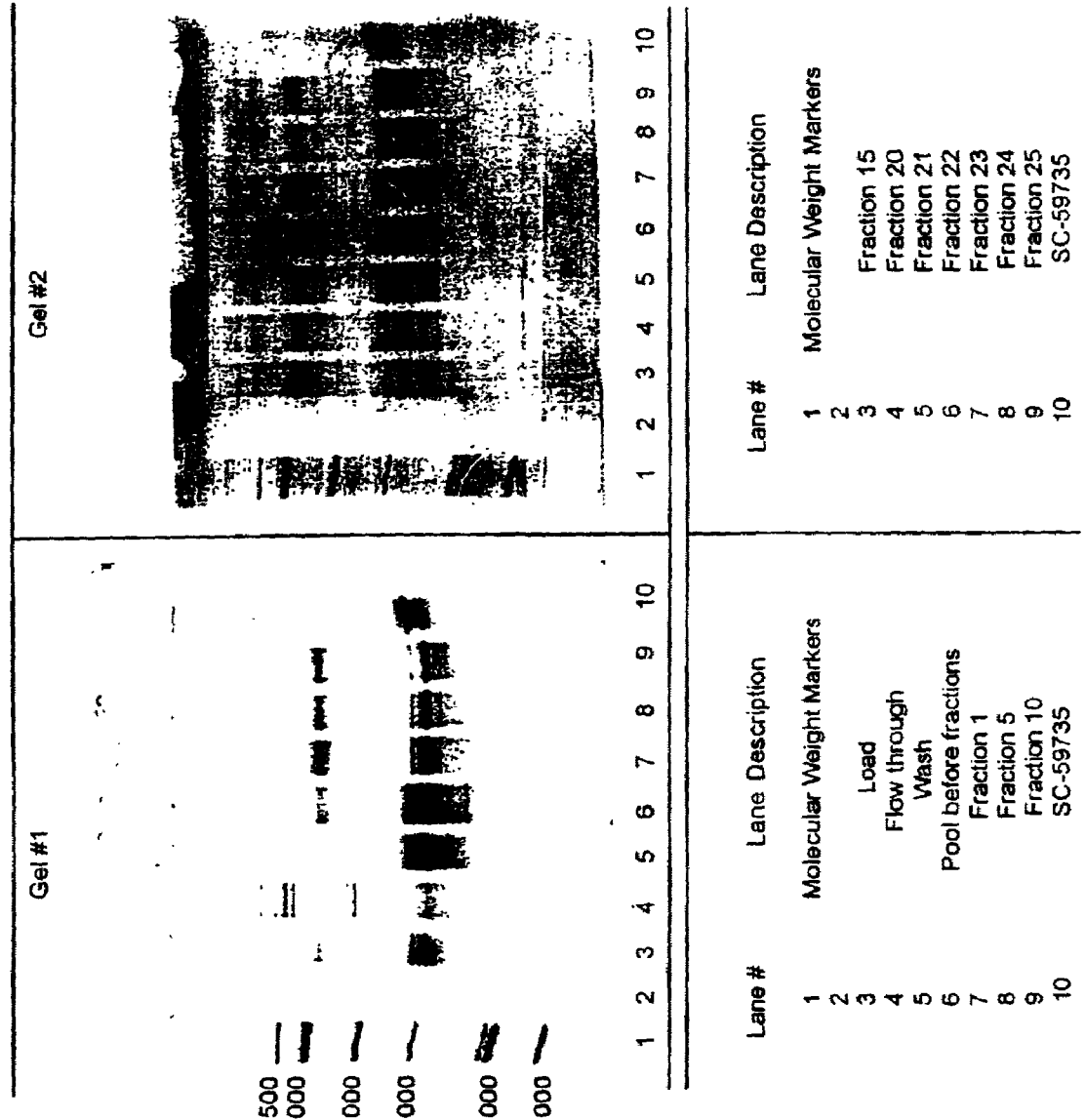
Figure 21B:
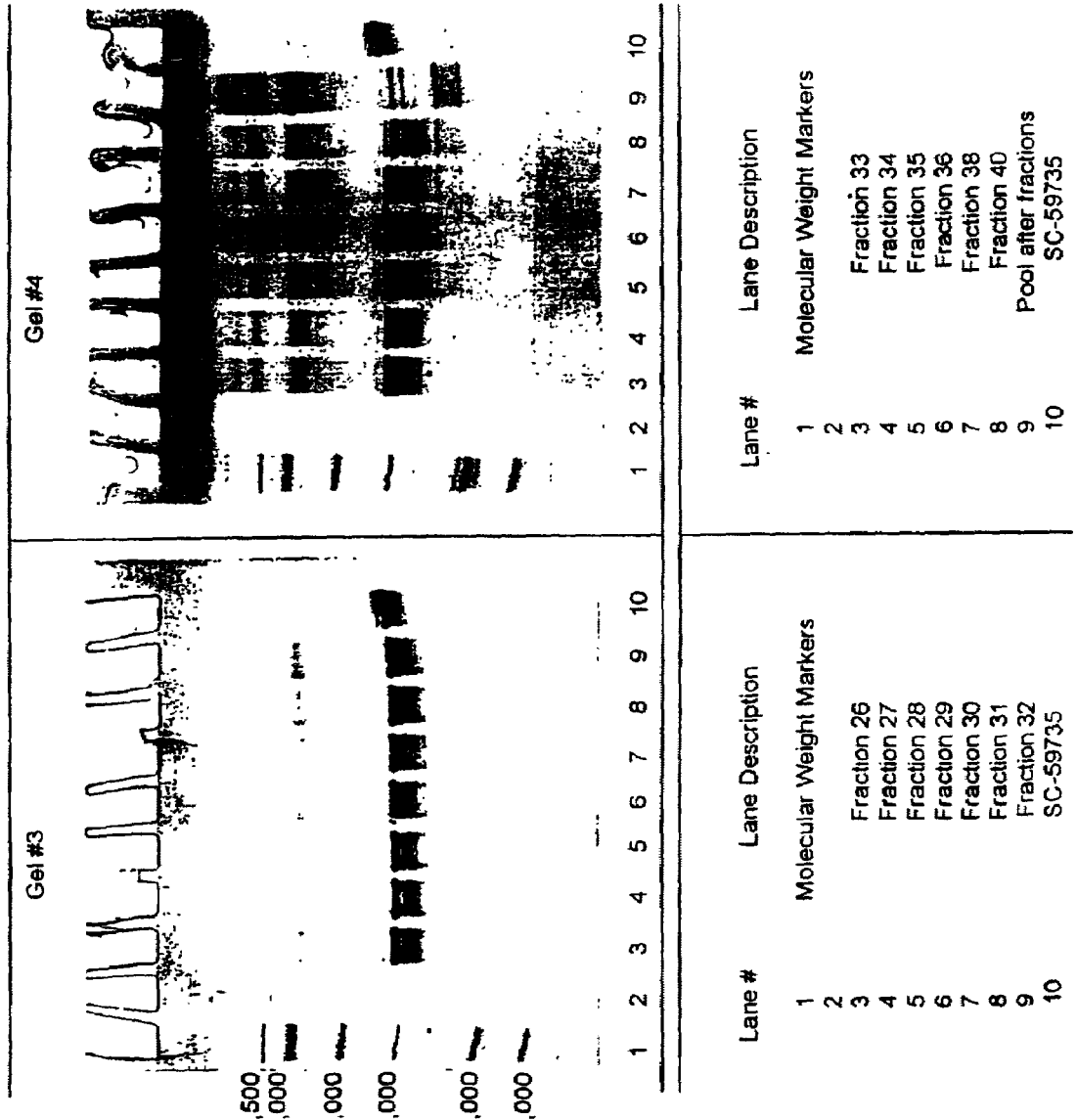

FIG. 21 shows SDS PAGE analysis of fractions collected during elution of the S-Sepharose HP column used to purify rhTFPI from a polyethyleneimine facilitated refold. FIG. 21A shows Load through Fraction 25, and FIG. 21B shows Fractions 26-Pool after fractions.

FIG. 22 shows the absorbance at 280 nm during the loading and elution of the Q-Sepharose HP column used to purify rhTFPI from a S-Sepharose pool prepared from a polyethyleneimine-facilitated refold.

Figure 23A:
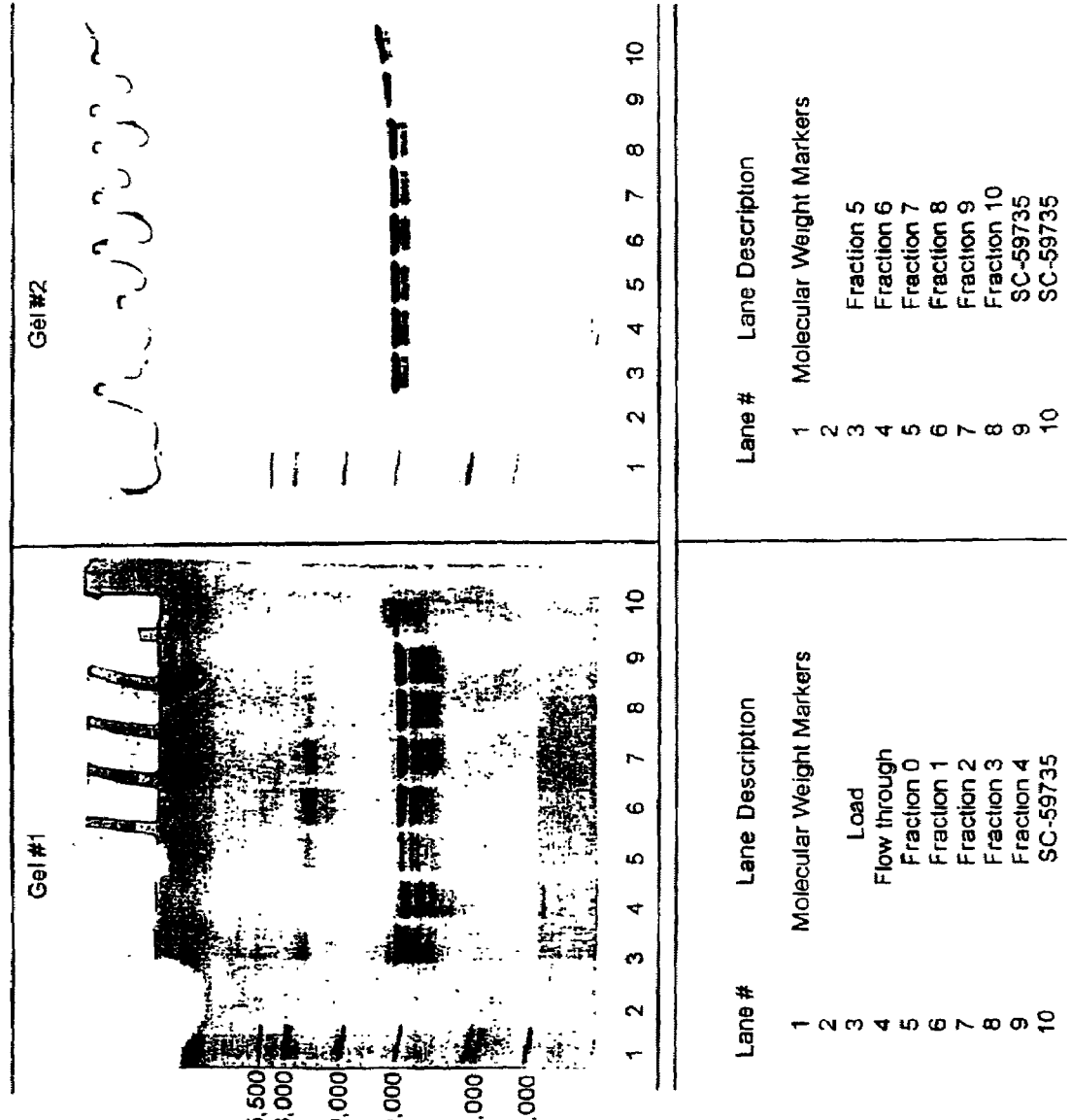
Figure 23B:
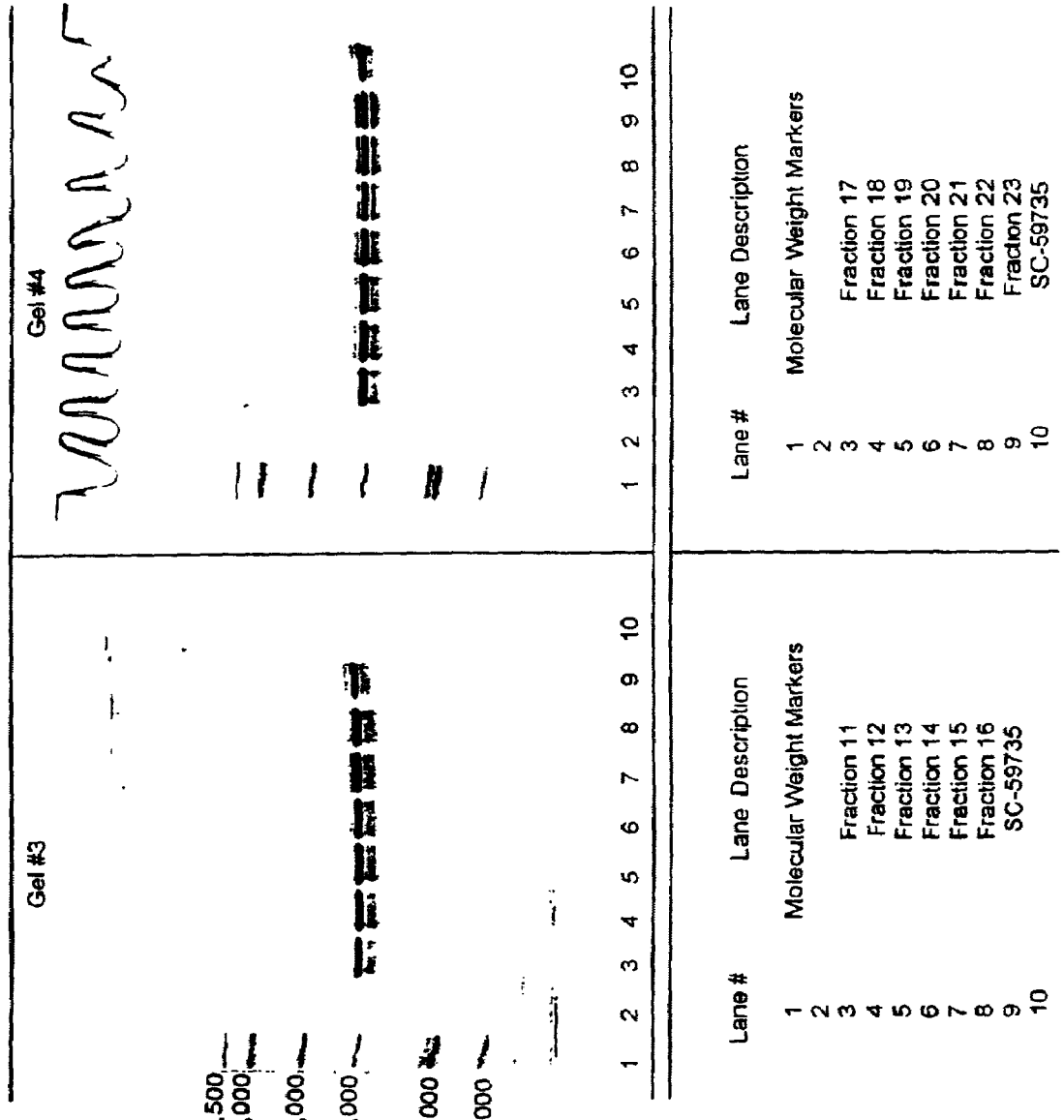
Figure 23C:
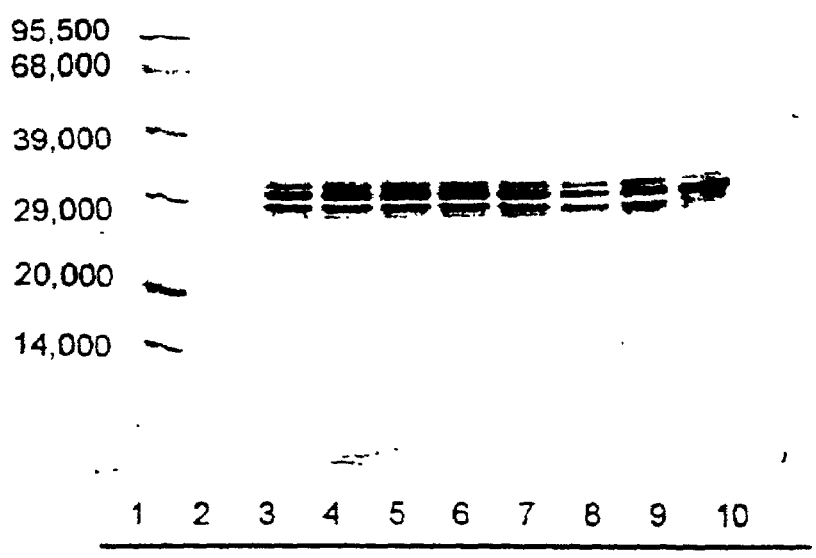

FIG. 23 shows SDS PAGE analysis of fractions collected during elution of the Q-Sepharose HP column used to purify rhTFPI from a S-Sepharose pool prepared from a polyethyleneimine-facilitated refold. FIG. 23A shows Load through Fraction 10, FIG. 23B shows Fractions 11–23, and FIG. 23C shows Fractions 24–30.

Figure 24:
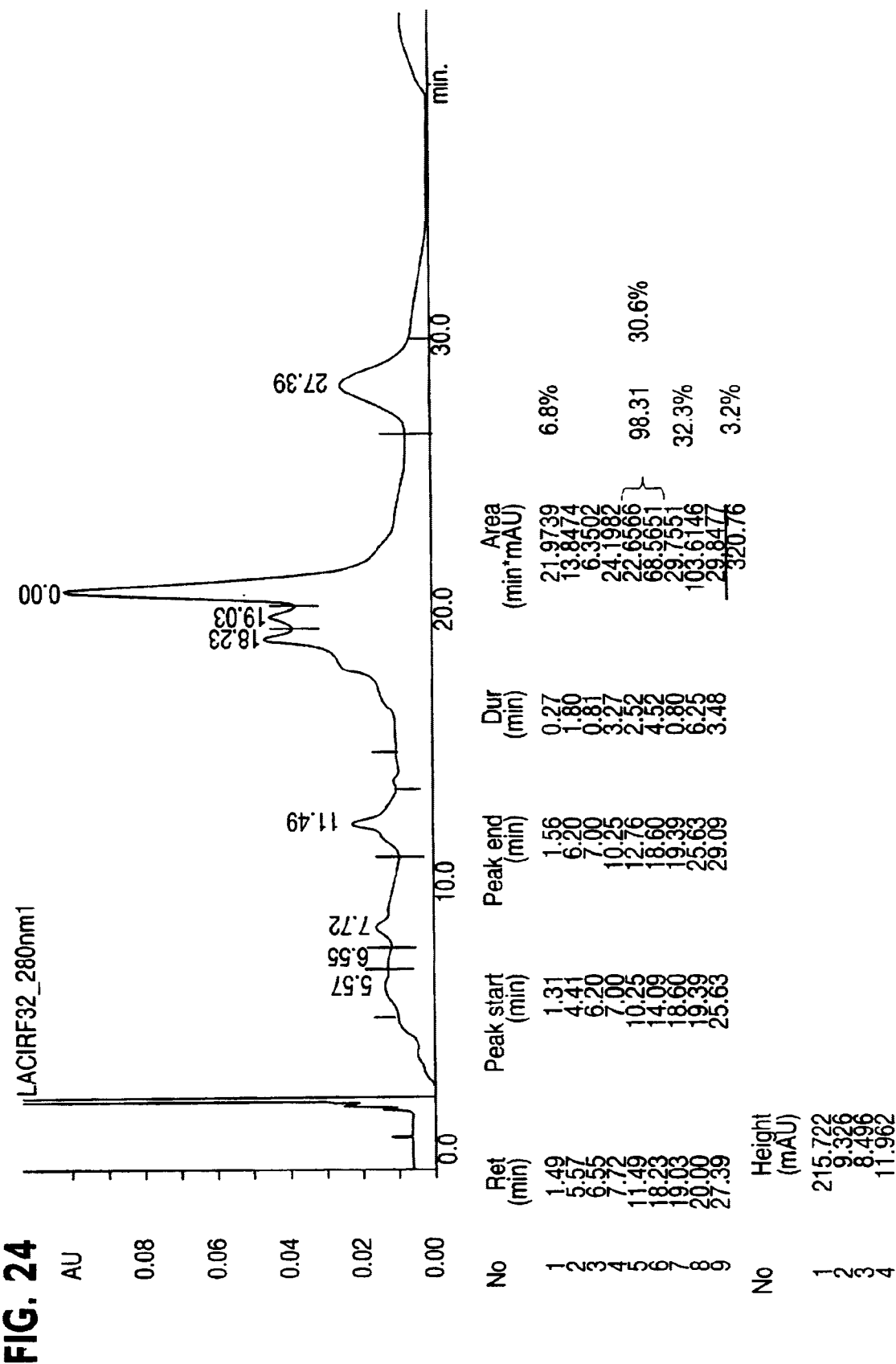

FIG. 24 shows the cation exchange HPLC analysis of a 0.4% polyphosphate-facilitated rhTFPI refold in the absence of urea.

Figure 25:
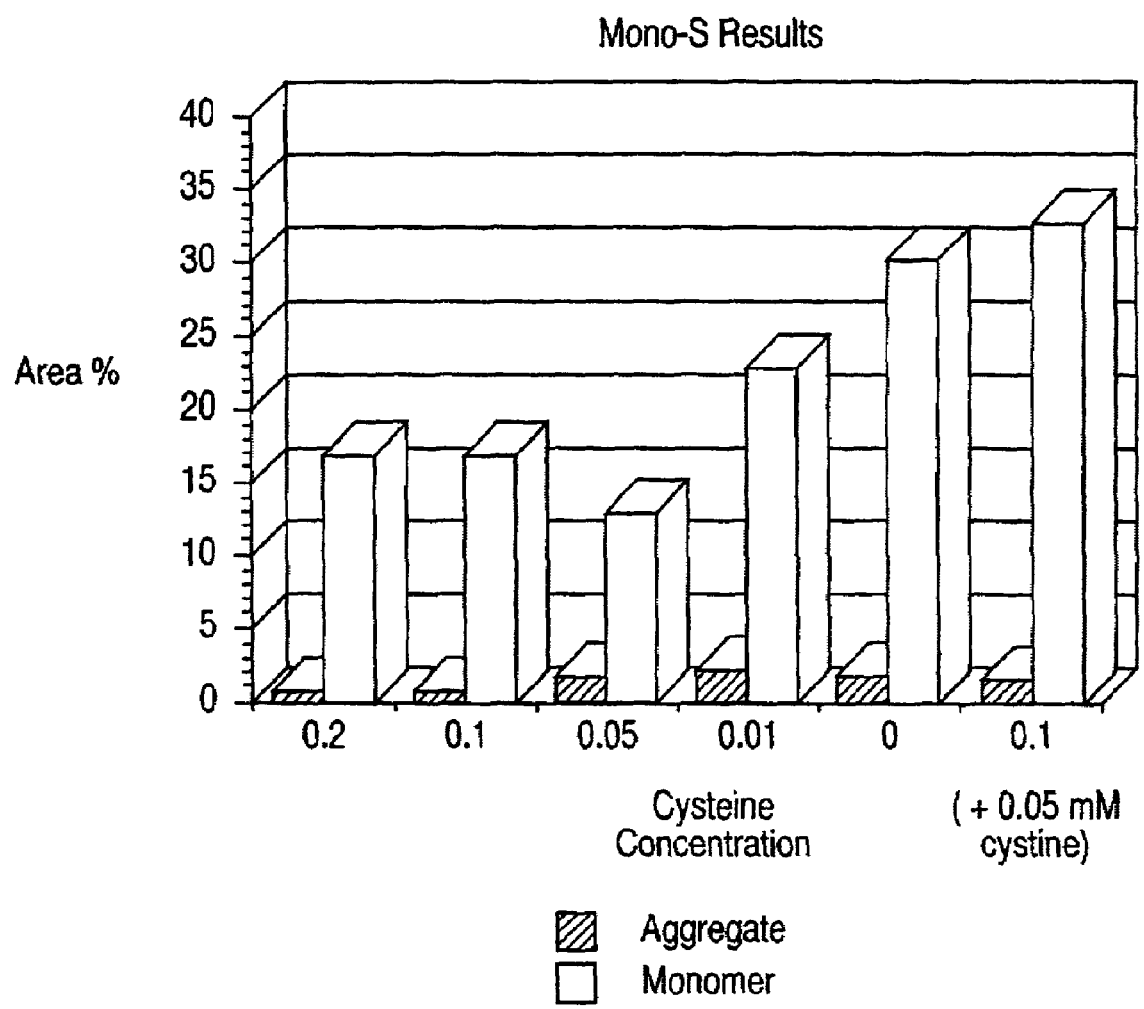

FIG. 25 shows results of cation exchange HPLC analysis of an evaluation of different levels of cysteine on a rhTFPI refold in 0.4% polyphosphate, 50 mM Tris in the absence of urea.

Figure 26A:
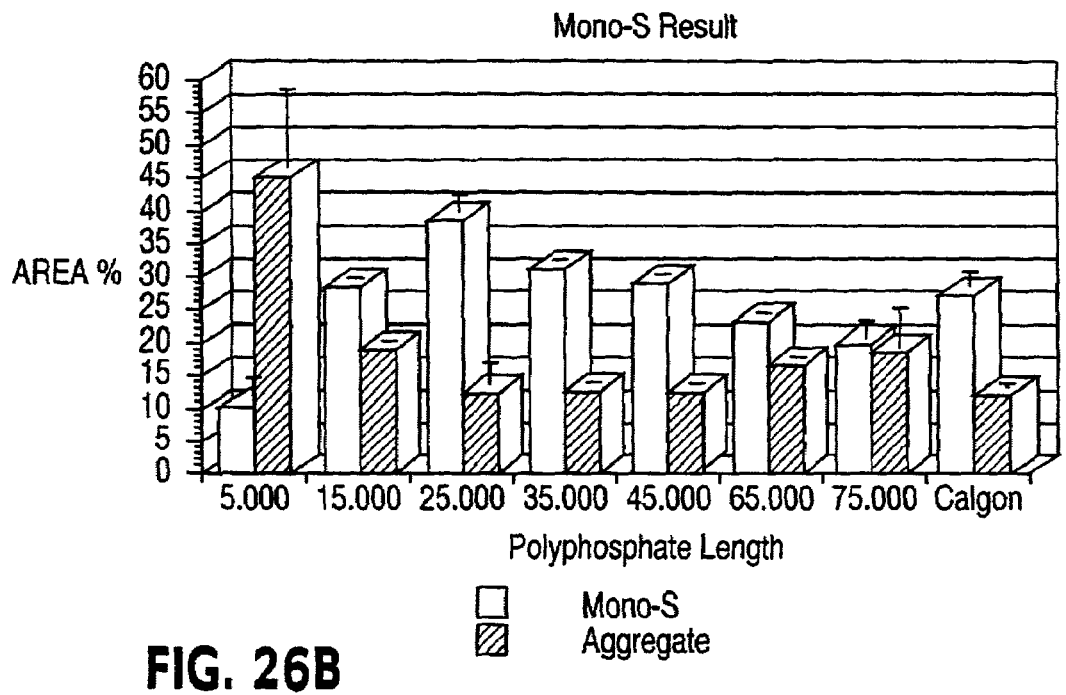
Figure 26B:
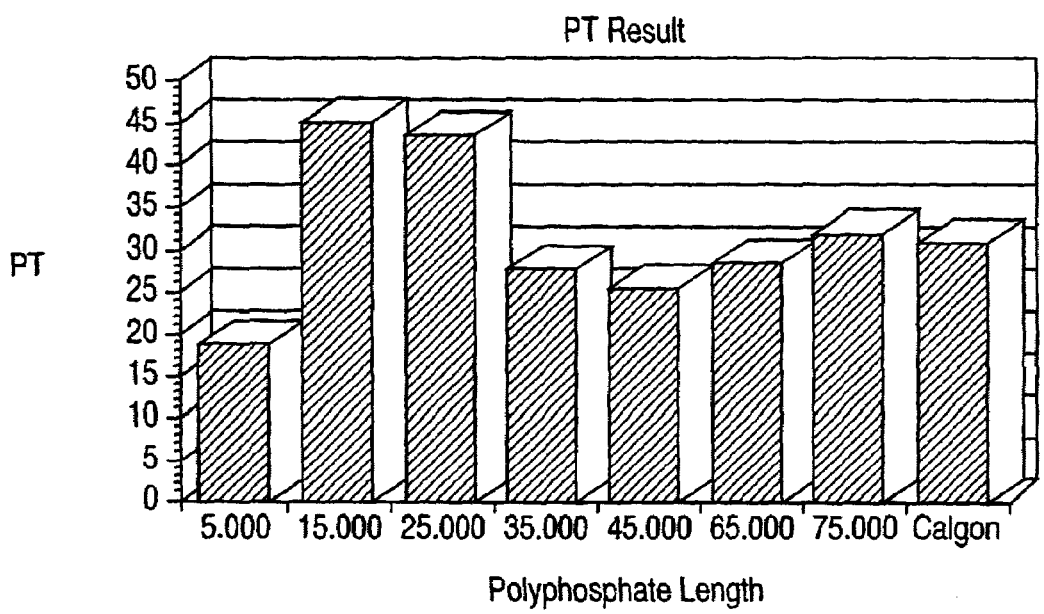

FIG. 26 shows the effect of polyphosphate chain length on the course of a polyphosphate facilitated refold of rhTFPI inclusion bodies as monitored by cation exchange HPLC.

Figure 27A:
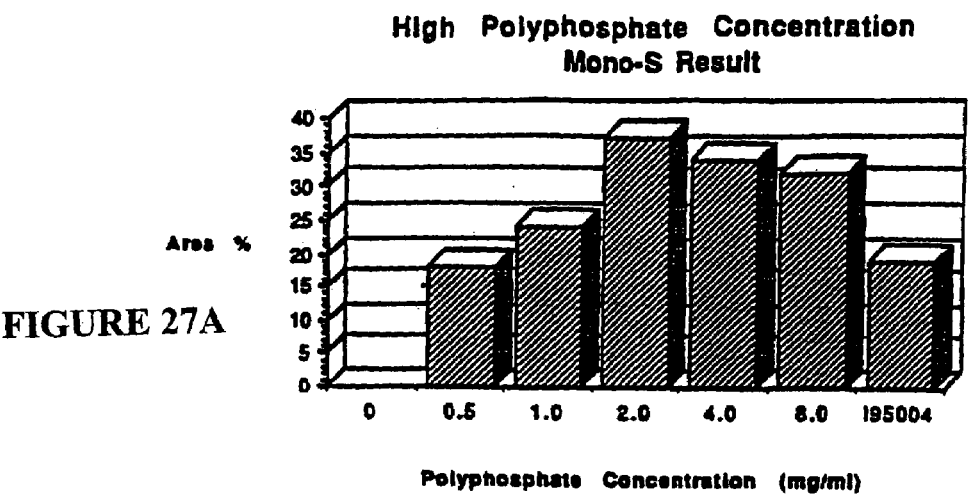
Figure 27B:
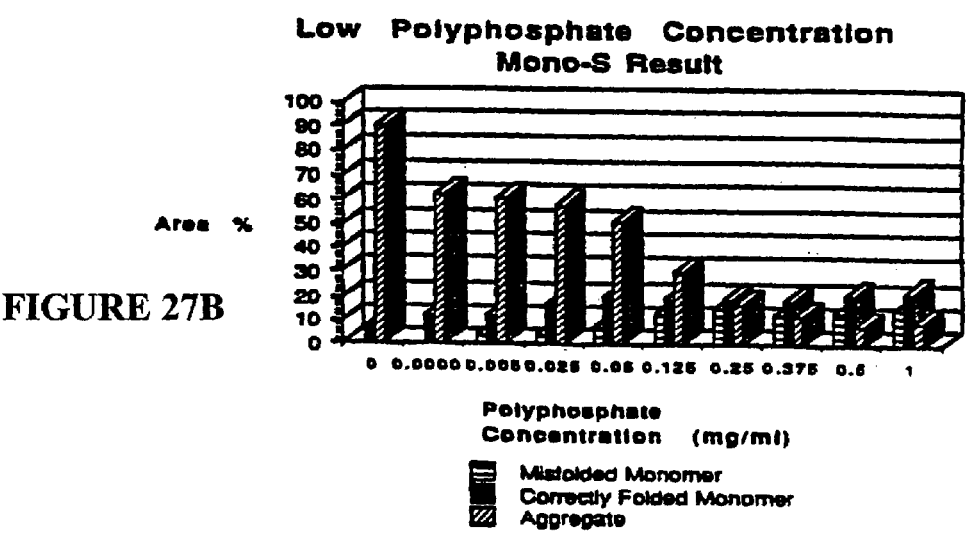

FIG. 27 shows the effect of concentration of polyphosphate (Glass H) on the refolding of rhTFPI from inclusion bodies as monitored by cation exchange HPLC.

Figure 28A:
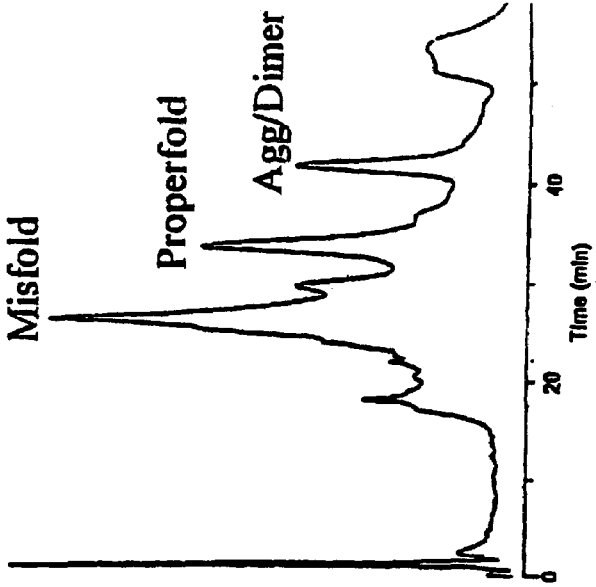
Figure 28B:
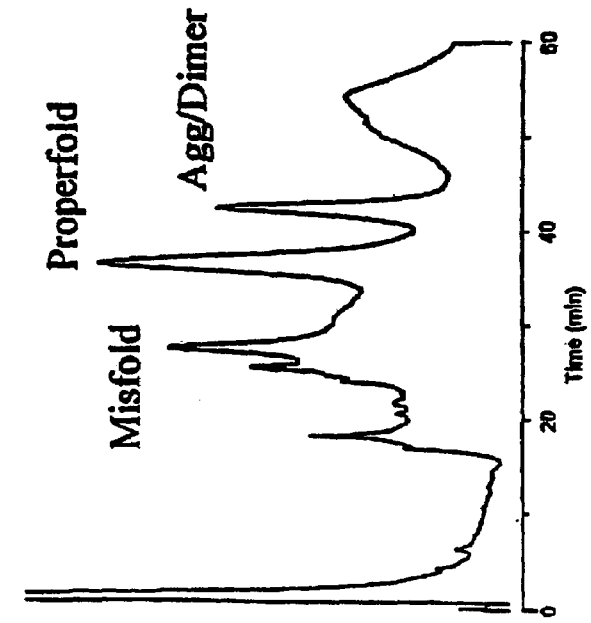

FIG. 28 shows the cation exchange HPLC analysis of polyethyleneimine and polyphosphate-facilitated refolding of purified and reduced rhTFPI.

SUMMARY OF THE INVENTION

It is an object of the present invention to describe a method of refolding protein.

It is another object of the invention to provide aqueous formulations of TFPI.

It is another object of the invention to provide methods for modifying a protein's solubility using charged polymers.

It is still another object of the present invention to describe a method of refolding TFPI including the steps of adding charged polymers to a solution of denatured TFPI prior to allowing the TFPI to refold.

Additionally, it is another object of the invention to describe a method of refolding TFPI including the step of immobilizing charged polymers on a column and passing a solution of denatured TFPI through the column and eluting the refolded TFPI after the refolding has occurred.

It has now been found that solubility of TFPI is strongly dependent on pH and, surprisingly, that polyanions such as citrate, isocitrate, and sulfate have profound solubilizing effects on TFPI. This finding is surprising in light of the hydrophobic nature of TFPI and the hydrophilic character of these counterions. Thus, citrate, isocitrate, sulfate as well as other solubilizers described hereinbelow can be used to produce pharmaceutically acceptable compositions having TFPI concentrations sufficient for administration to patients. It has also been shown that other organic molecules can act as secondary solubilizers. These secondary solubilizers include PEG, sucrose, mannitol, and sorbitol.

The invention relates to pharmaceutically acceptable compositions wherein TFPI is present in a concentration of more than 0.2 mg/mL solubilizing agents. The solubilizing agents may be acetate ion, sodium chloride, citrate ion, isocitrate ion, glycine, glutamate, succinate ion, histidine, imidazole and sodium dodecyl sulfate (SDS) as well as charged polymers. In some compositions, TFPI may be present in concentrations of more than 1 mg/mL and more than 10 mg/mL. The composition may also have one or more secondary solubilizers. The secondary solubilizer or solubilizers may be polyethylene glycol (PEG), sucrose, mannitol, or sorbitol. Finally, the composition may also contain sodium phosphate at a concentration greater than 20 mM.

Although the solubility of TFPI is quite low between pH 5 and 10, it has been found that L-arginine can increase the solubility by a factor of 100. The solubility is very dependent on the concentration of arginine, as 300 mM is about 30 times more effective than 200 mM. Urea also is quite effective in solubilization of TFPI.

Further, it has been found that aggregation of TFPI appears to be the major degradation route at neutral and basic pH conditions and that fragmentation occurs at acidic pH conditions.

It has also been found that active TFPI monomers can be separated away from TFPI oligomers that are produced during the process of folding recombinant TFPI produced *E. coli*. Some misfolded/modified monomeric forms of TFPI are also removed during this process. The separation employs hydrophobic interaction chromatography. The oligomeric species of HOPI bind more tightly to a hydrophobic resin than does the active TFPI monomers. Resins such as Pharmacia™ octyl sepharose and Toyopearl™ butyl 650-M have been successful. The process is carried out in the presence of high salt, such as 1 M ammonium sulfate or 0.5 M sodium citrate.

DETAILED DESCRIPTION OF THE INVENTION

It is a discovery of the present inventors that polyionic polymers such as polyethylene imine and polyphosphate, can modify the ionic interactions within proteins. The masking of certain areas of high charge density within proteins using polyions can have numerous effects. Proteins whose solubility is reduced through the intra- and/or inter-molecular neutralization of oppositely charged areas can have their solubility improved by masking one of the charged regions with polycations or polyanions. Barriers to conformational flexibility and specific attractive or repulsive forces which interfere with the refolding process can be modulated as well. Proteins which require strong denaturants such as urea or guanidine hydrochloride to solubilize and maintain solubility during purification operations can be solubilized and processed effectively using polyions.

Many proteins lacking a clear region of charge localization in the primary sequence can still demonstrate areas of charge localization due to their secondary structure. Thus many proteins can have their solubility, refolding, and purification characteristics modified through interaction with charged polymeric templates. The nature of the modification will depend on the specific protein structure, the chain length, charge, and charge density of the ionic polymer.

We have characterized refolding of pure TFPI in a guanidine or a urea based refolding buffer and the results indicate that refolding efficiencies and kinetics can be significantly improved by the addition of charged polymers including heparin, dextran sulfate, polyethyleneimine (PEI) and polyphosphates. These polymers increase TFPI solubility and enhance refolding through ionic interactions with either the N-terminus or the C-terminus. In addition to the polymer additives, refolding pure TFPI requires a cysteine cystine redox buffer where the refolding reaction can be completed within 48 hours. Refolding yields are a strong function of pH, redox concentration, and polymer additives; however refolding efficiencies as high as 60% can be achieved for pure TFPI under optimum refolding conditions.

It has been found by the inventors of this invention that addition of glycosaminoglycans or sulfated polysaccharides such as, for example, heparin and dextran sulfate, to a solution containing a denatured protein prior to refolding increases the amount of correctly folded, active protein where the protein is capable of binding to the glycosaminoglycan or sulfated polysaccharide and is subjected to renaturing conditions.

Dissolution

Recombinant DNA technology has allowed the high level expression of many proteins that could not normally be isolated from natural sources in any appreciable quantities. In *E. coli* and several other expression systems, the protein is frequently expressed in an inactive, denatured state where the primary amino acid sequence is correct, but the secondary and tertiary structure and any cysteine disulfide bonds are not present. The denatured protein present in an inclusion body may be in such a conformation that charged residues of different parts of the amino acid backbone that are not normally in contact are able to interact and form strong ionic bonds between positively charged and negatively charged amino acid residues. The formation of these ionic bonds may limit the hydration that must occur to effect dissolution of the inclusion body. The protein in an inclusion body may also be complexed with other cellular components such as membrane components and nucleic acid which may also limit the access of solvent (water) to charged and normally hydrated residues. Also found in the unfolded state is that hydrophobic residues which are normally found buried in the interior of a protein are more exposed to the polar aqueous environment. Such occurrences may work to prevent the dissolution of inclusion bodies in solvents other than strong chaotropic agents such as urea or guanidine or detergents such as SDS.

Charged polymers preferably in aqueous solution can interfere with and disrupt the undesirable ionic interactions that occur within a polypeptide chain as found in an inclusion body or other environment. The charged polymers may help disrupt the undesirable ionic interactions and facilitate solvation of ionic and polar residues, promoting dissolution without the need for strong chaotropes or detergents. The charge, charge density, and molecular weight (chain length) of the charged polymer may vary depending on the specific protein. Suitable polymers include: sulfated polysaccharides, heparins, dextran sulfates, agaropectins, carboxylic acid polysaccharides,alginic acids, carboxymethyl celluloses, polyinorganics, polyphosphates, polyaminoacids, polyaspartates, polyglutamates, polyhistidines, polyorganics, polysaccharides,DEAE Dextans, polyorganic amines, polyethyleneinimes, polyethyleneinime celluloses, polyamines, polyamino acids, polylysines, and polyarginines.

Proteins with pI greater than 7 may benefit more from interactions with negatively charged polymers, as these proteins will have a positive charge at pH 7. Proteins with pIs below 7 may interact more strongly with positively charged polymers at neutral pH. Changing the solution pH will modify the total charge and charge distribution of any protein, and is another variable to be evaluated.

Refolding

Recombinant DNA technology has allowed the high level expression of many proteins that could not normally be isolated from natural sources in any appreciable quantities. In *E. coli* and several other expression systems, the protein is frequently expressed in an inactive, denatured state where the primary amino acid sequence is correct, but the secondary and tertiary structure and any cysteine disulfide bonds are not present. The denatured protein must be refolded to the proper active conformation, which often requires overcoming significant energy barriers imposed by ionic attraction and repulsion, restrictions on bond rotation, and other types of conformationally induced stresses. Specific ionic attraction between opposite charges and/or repulsion between like charges can severely limit the refolding pathways available to the denatured protein and reduce the efficiency of the refolding process.

Some proteins have specific areas of charge whose interactions may limit conformational flexibility or promote aggregation. Many proteins lacking a clear region of charge localization in the primary sequence can still demonstrate areas of charge localization due to their secondary structure found in refolding intermediates, misfolds and improperly folded protein. Proteins which are particularly suitable according to the present invention include but are not limited to TFPI, TFPI muteins, TFPI-2, tissue plasminogen activator, BST, PST. While it is believed that these methods will be suitable for use with proteins generically, those which are most suitable are those which are improperly folded, aggregated, oligomerized, or inactive. These will likely be proteins which have at least one highly charged domain, and possibly more, which can interact. In the case of TFPI, as well as other proteins, two oppositely charged domains interact with each other to prohibit proper folding and to cause oligomerization and aggregation. Proteins having many disulfide bonds will also be most likely to benefit from the present methods. Preferably the protein will have at least 2 and more preferably the protein will have at least 4 or 6 disulfide bonds.

Charged polymers can be used to modify the charge, charge density, and reduce or eliminate ionically mediated limitations to conformation that may arise in the unfolded state. The juxtaposition of charged groups that are not normally in proximity may have result in dead-end refolding pathways from which the refolding process may never recover.

The introduction of extra positive or negative charges through the complexation with charged polymers may allow refolding to proceed more facilely for several reasons: first different types of charge distributions may better accommodate the refolding process; second, the addition of the charged polymer may enhance the solubility of the unfolded protein, reducing or eliminating the need for chaotropes which have a negative effect on protein conformation.

Because of the frequently unique structure associated with most proteins the charged polymer that demonstrates preferred characteristics may vary. Evaluation of the isoelectric pH (pI) of the protein can serve as a starting point. At neutral pH a protein with a pI less than 7 will possess a net negative charge, and will thus be more likely to bind a positively charged polymer. The protein with a pI greater than 7 will possess a net positive charge at neutral pH, and will have a stronger tendency to bind a negatively charged polymer. However, it is well established that charges are unevenly distributed around a protein, and significant charge localization can occur. The possibility of localized concentrations of charges reduce the ability to predict which type of charged polymer may be most effective for any application. Theoretically, for any protein with a specific distribution of interacting charges and conformational requirements, there exists a charged polymer of appropriate compositions in terms of molecular weight, charge, and charge distribution which would maximize refolding efficiency. Other variables, such as pH and solvent ionic strength, would also be evaluated. Initial screening would involve polyethyleneimine, DEAE dextran, dextran sulfate, and polyphosphate at several different concentrations and molecular weights. Work with rhTFPI has demonstrated the significant impact hat polyphosphate chain length and concentration can have on the course of the TFPI refolding reaction. Relatively short chain length (n=5) produces high levels of aggregate. The optimal polyphosphate chain length for refolding rhTFPI was approximately 25 repeating units. Longer chain length polyphosphates (n=75) also produced more aggregate and less properly folded monomer.

Formulation

Proteins consist of chains of amino acids, the exact composition and sequence of which constitutes one of the primary structure determinants of the protein. The secondary determinant of protein structure is the result of the conformational guidance that the individual amino acid bonds have on protein conformation. Thirdly, the specific amino acid sequence directs the formation of tertiary structures such as β-sheets and α-helices. The three dimensional nature of protein conformation often brings into proximity amino acid residues that are not normally close to each other based on the direct sequence of the polypeptide chain. The functional form of a protein is generally a modestly stable conformation held together by a combination of cysteine disulfide bonds, ionic bonds, and hydrophobic and Van der Waals interactions.

In general, protein solubility can be related to the number of charged and to a lesser extent polar amino acids that make up the protein. These charged and polar groups become solvated with water molecules in the aqueous solution and this interaction keeps the polypeptide chain in solution. Polypeptides with insufficient numbers of positively or negatively charged amino acids can have limited aqueous solubility. In some cases, the positive and negatively charged groups present in a protein can interact with each other, displacing the water of solvation and leading to reduced aqueous solubility. Many proteins lacking a clear region of charge localization in the primary sequence can still demonstrate areas of charge localization due to their secondary structure. Thus many proteins can have their solubility modified through interaction with charged polymeric templates. The nature of the modification will depend on the specific protein structure, the chain length, charge, and charge density of the ionic polymer.

Complexation with charged polymers with relatively high charge density represents one approach to increasing the charge density of any protein. A protein with a small number of positively charged residues (lysine or arginine) can be complexed with a negatively charged polymer such as polyphosphate. Some of the negatively charged groups of the polymer will interact with the positively charged groups present in the protein. The remaining charged groups on the polymer will be free to interact with the solvent, in most cases water, and effectively increase the charge density and solvation of the protein. Alternatively, a positively charged polymer such as polyethyleneimine can be used to complex with the negatively charged residues of the protein. In some cases both types of charged polymers may work equally effectively, in other cases, one charge type may be more effective than others. The effectiveness of any particular charged polymer, will depend on protein amino acid composition, protein amino acid distribution, protein conformation, charged polymer charge density, charged polymer chain length, solution pH, and other variables. However, it is likely that for any given protein, a complementary charged polymer that will bind to the protein and essentially increase the charge density of protein can be found that will improve the solubility characteristics of that protein in aqueous medium.

Definitions

The term "processing" as used herein refers to the steps involved in the purification and preparation of pharmaceutically-acceptable amounts of proteins. Processing may include one or more steps such solubilization, refolding, chromatographic separation, precipitation, and formulation.

The term "charged polymer" and "charged polymeric template" refer to any compound composed of a backbone of repeating structural units linked in linear or non linear fashion, some of which repeating units contain positively or negatively charged chemical groups. The repeating structural units may be polysaccharide, hydrocarbon, organic, or inorganic in nature. The repeating units may range from n=2 to n=several million The term "positively charged polymer" as used herein refers to polymers containing chemical groups which carry, can carry, or can be modified to carry a positive charge such as ammonium, alkyl ammonium, dialkylammonium, trialkyl ammonium, and quaternary ammonium.

The term "negatively charged polymer" as used herein refers to polymers containing chemical groups which carry, can carry, or can be modified to carry a negative charge such as derivatives of phosphoric and other phosphorous containing acids, sulfuric and other sulfur containing acids, nitrate and other nitrogen containing acids, formic and other carboxylic acids The term "polyethyleneimine" as used herein refers to polymers consisting of repeating units of ethylene imine (H3N+—(CH2—CH2—NH2+)x—CH2—CH2—NH3+). The molecular weight can vary from 5,000 to greater than 50,000.

The term "polyphosphate" as used herein refers to polymers consisting of repeating units of orthophosphate linked in a phospho anhydride linkage. The number of repeating units can range from 2 (pyrophosphate) to several thousand. Polyphosphate is frequently referred to as sodium hexametaphosphate (SHMP) Other common names include Grahams salt, Calgon, phosphate glass, sodium tetrametaphosphate, and Glass H.

The term "refold" as used herein refers to the renaturation of protein. Typically, the goal of refolding is to produce a protein having a higher level of activity than the protein would have if produced without a refolding step. A folded protein molecule is most stable in the conformation that has the least free energy. Most water soluble proteins fold so that most of the hydrophobic amino acids are in the interior part of the molecule, away from the water. The weak bonds that hold a protein together can be disrupted by a number of treatments that cause a polypeptide to unfold, i.e. denature. A folded protein is the product of several types of interactions between the amino acids themselves and their environment, including ionic bonds, Van der Waals interactions, hydrogen bonds, disulfide bonds and covalent bonds.

The term "denature" as used herein refers to the treatment of a protein or polypeptide in which results in the disruption of the ionic and covalent bonds and the Van der Waals interactions which exist in the molecule in its native or renatured state. Denaturation of a protein can be accomplished, for example, by treatment with 8 M urea, reducing agents such as mercaptoethanol, heat, pH, temperature and other chemicals. Reagents such as 8 M urea disrupt both the hydrogen and hydrophobic bonds, and if mercaptoethanol is also added, the disulfide bridges (S—S) which are formed between cysteines are reduced to two —S—H groups. Refolding of proteins which contain disulfide linkages in their native or refolded state may also involve the oxidation of the —S—H groups present on cysteine residues for the protein to reform the disulfide bonds.

The term "glycosaminoglycan" as used herein refers to polysaccharides containing alternating residues of uronic acid and hexosamine and usually contain sulfate. The binding of a protein in a refolding reaction as described herein to a glycosaminoglycan is through ionic interactions.

The term "dextran sulfate" as used herein refers a polyanionic derivative of dextran, ranging in molecular weight from 8,000 to 500,000 daltons. Dextrans are polymers of glucose in which glucose residues are joined by $\alpha 1,6$ linkages.

The term "heparin" as used herein refers to 2 glucoaminoglycans or heparinoids which are based on a repeating disaccharide (-4DGlcA(p)β1, 4GlcNAcα1-)$_n$ but are subject to extensive modification after assembly. Heparin is stored with histamine in mast cell granules and is thus found in most connective tissues. In general heparins have shorter chains than heparin.

The term "HIC" as used herein refers to hydrophobic interaction chromatography which employs a hydrophobic interaction between the column and the molecule of interest to separate the sulfated polysaccharides and other contaminants from the refolded product.

Negatively charged polymers include sulfated polysaccharides, such as heparins, dextran sulfates, and agaropectins, as well as carboxylic acid polysaccharides such asalginic acids and carboxymethyl celluloses. Polyinorganics such as polyphosphates are also included. Polyamino acids such as polyasparatate, polyglutamate, and polyhistidine can also be used.

Positively charged polymers include polysaccharides such as DEAE dextran, polyorgnic amines, such as polyethyleneimines, polyethyleneimine celluloses, and polyamines, as well as the polyamino acids, polylysine and polyarginine. Combinations of polymers may be used, of either charge polarity. In addition, amphoteric co-polymers may also be used.

As used herein, "TFPI" refers to mature Tissue Factor Pathway Inhibitor. As noted above, TFPI is also known in the art as Lipoprotein Associated Coagulation Inhibitor (LACI), Extrinsic Pathway Inhibitor (EPI) and Tissue Factor Inhibitor (TFI). Muteins of TFPI which retain the biological activity of TFPI are encompassed in this definition. Further, TFPI which has been slightly modified for production in bacterial cells is encompassed in the definition as well. For example, a TFPI analog has an alanine residue at the amino-terminal end of the TFPI polypeptide has been produced in *Escherichia coli*. See U.S. Pat. No. 5,212,091.

As used herein, "pharmaceutically acceptable composition" refers to a composition that does not negate or reduce the biological activity of formulated TFPI, and that does not have any adverse biological effects when formulated TFPI is administered to a patient.

As used herein, "patient" encompasses human and veterinary patients.

As used herein, the term "solubilizer" refers to salts, ions, carbohydrates, amino acids and other organic molecules which, when present in solution, increase the solubility of TFPI above 0.2 mg/mL. Solubilizers may also raise the concentrations of TFPI above 1 mg/mL and above 10 mg/mL. It should be noted that solubilizers may act as stabilizing agents. Stabilizing agents preserve the unit activity of TFPI in storage and may act by preventing formation of aggregates, or by preventing degradation of the TFPI molecule (e.g. by acid catalyzed reactions).

As used herein, the term "secondary solubilizers" refers to organic salts, ions, carbohydrates, amino acids and other organic molecules which, when present in solution with a solubilizer, further increase the solubility of TFPI. Secondary solubilizers may have other effects as well. For example, secondary stabilizers may be useful in adjusting tonicity (e.g. to isotonicity).

Figure 4:
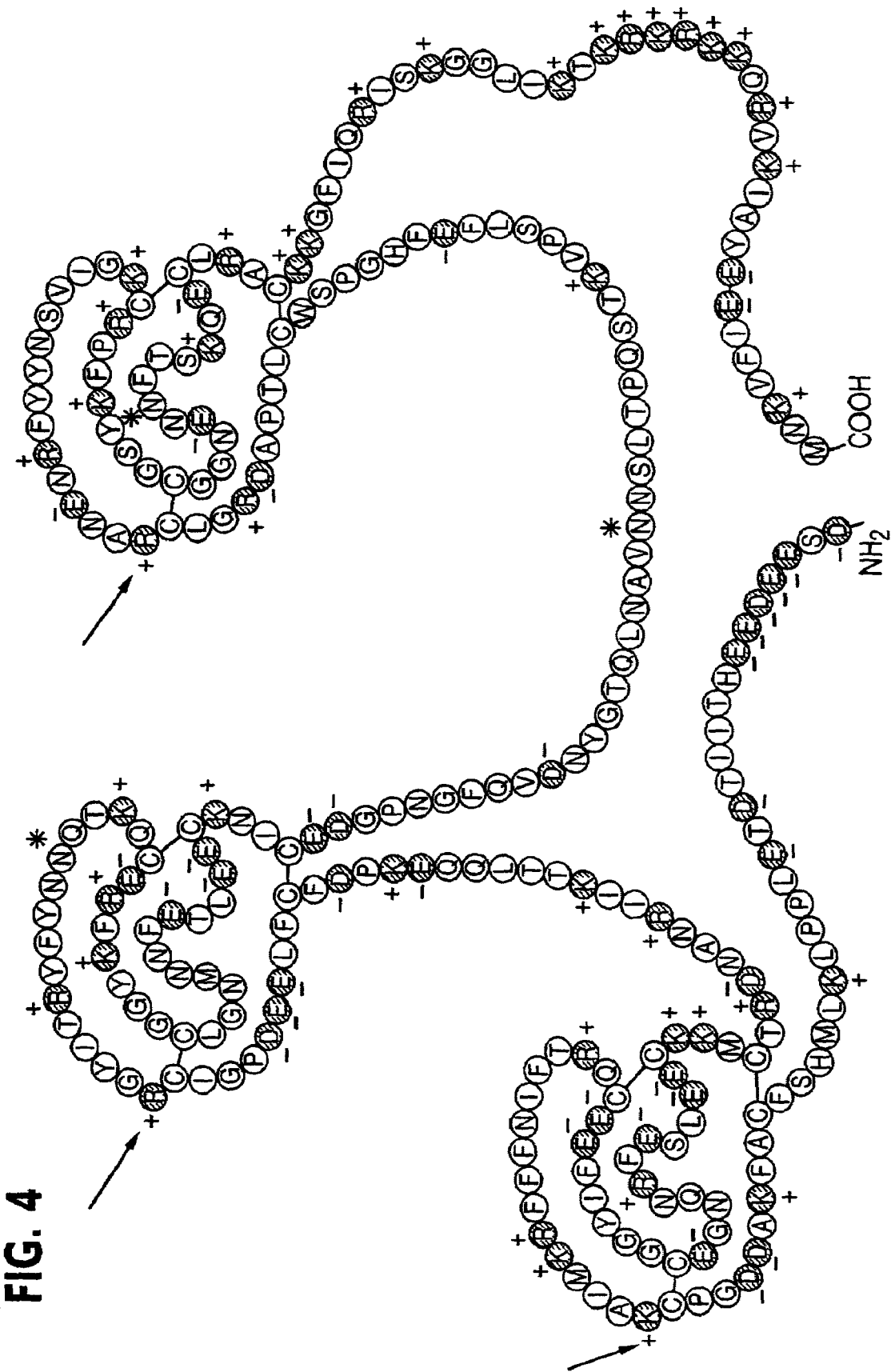
FIG. 4 is the amino acid sequence of TFPI (SEQ ID NO: 1).

The amino acid sequence of TFPI is disclosed in U.S. Pat. No. 5,106,833 which is herein incorporated by reference and FIG. 4. Muteins of TFPI and TFPI-2 are disclosed in U.S. Ser. No. 08/286,530 which is herein incorporated by reference. As described in U.S. Ser. No. 08/286,530, muteins of TFPI and TFPI-2, with single or multiple point mutations, and chimeric molecules of TFPI and TFPI-2 can be prepared. For instance, the lysine residue in the P1 site of the first Kunitz-type domain of TFPI may be replaced with arginine. Muteins, containing one to five amino acid substitutions, may be prepared by appropriate mutagenesis of the sequence of the recombinant cloning vehicle encoding TFPI or TFPI-2. Techniques for mutagenesis include, without limitation, site specific mutagenesis. Site specific mutagenesis can be carried out using any number of procedures known in the art. These techniques are described by Smith (1985) *Annual Review of Genetics*, 19:423, and modifications of some of the techniques are described in METHODS IN ENZYMOLOGY, 154, part E, (eds.) Wu and Grossman (1987), chapters 17, 18, 19, and 20. A preferred procedure when using site specific mutagenesis is a modification of the Gapped Duplex site directed mutagenesis method. The general procedure is described by Kramer, et al., in chapter 17 of the Methods in Enzymology, above. Another technique for generating point mutations in a nucleic acid sequence is overlapping PCR. The procedure for using overlapping PCR to generate point mutations is described by Higuchi in Chapter 22 of PCR PROTOCOLS: A GUIDE TO METHODS AND APPLICATIONS, (eds.) Innis, Gelfand, Sninsky and White (Academic Press, 1990).

Alternatively, hybrid proteins containing the first Kunitz-type domain of TFPI-2 and the second and third Kunitz-type domains of TFPI could be produced. One skilled in the art of DNA cloning in possession of the DNA encoding TFPI and TFPI-2 would be able to prepare suitable DNA molecules for production of such a chimeric protein using known cloning procedures. Alternatively, synthetic DNA molecules encoding part or all of each Kunitz-type domain and peptide sequences lining the Kunitz-type domains can be prepared. As a further alternative, the overlapping PCR technique may also be used to prepare DNA encoding chimeric molecules containing TFPI and TFPI-2 sequences.

TFPI can be prepared in yeast expression systems as described in U.S. Ser. No. 08/286,530 (now abandoned, but continuation issued as U.S. Pat. No. 6,103,500), which is herein incorporated by reference. Methods have also been disclosed for purification of TFPI from yeast cell culture medium, such as in Petersen et al, *J. Biol. Chem.* 18:13344–13351 (1993). In these cases, recombinant TFPI is secreted from the yeast cell. TFPI recovered in such protocols is also frequently heterogeneous due to N-terminal modification, proteolytic degradation, and variable glycosylation. Therefore, a need exists in the art to produce mature TFPI that is authentic (i.e. having the correct N-terminal amino acid sequence), full-length and homogeneous.

TFPI can be produced in *E. coli* as described in U.S. Pat. No. 5,212,091 which discloses a method of producing TFPI by expression of a non-glycosylated form of TFPI in an *E. coli* host.

In one aspect of the invention recombinantly produced proteins which have the ability to bind polymers of sulfated polysaccharides such as, for example, heparin or dextran sulfate are refolded. The invention provides a method that facilitates refolding of a denatured recombinantly produced protein product using polymers of dated polysaccharides which act as a templates for the refolding protein. Without being limited to any particular theory, the inventors believe that the interactions between the refolding protein and the polymeric template may minimize aggregation of the refolding intermediates and provide an environment for the protein to refold to its native conformation. The polymer acting as a template may bind a domain or region of protein to stabilize the intermediate and allow further folding to occur without aggregation. The protein aggregates, if formed, are generally less active than non-aggregated refolded protein, and generally result in a reduced overall yield of active refolded protein. The NaCl concentration of the refolding conditions is considered important and is selected to achieve the max efficiency of refolding by maximizing the interaction between the template polymer and the refolding protein. For example, it has been found by the inventors that approximately 0.2 M concentration of NaCl or lower promotes binding of the C-terminal and/or the third Kunitz domain of TFPI to heparin or other sulfated polysaccharide polymer. The binding of polymer to the intermediate is presumed to facilitate the solubility of the intermediate and provide an environment for the rest of the protein to refold by reducing aggregation of the refolding intermediates.

General Methods

TFPI activity may be tested by the prothrombin time assay (PTT assays). Bioactivity of TFPI was measured by the prothrombin clotting time using a model RA4 Coag-A-Mate from Organon Teknika Corporation (Oklahoma City, Okla.). TFPI samples were first diluted to 9 to 24 ug/mL with a TBSA buffer (50 mM Tris, 100 mM NaCl, 1 mg/mL BSA, pH 7.5). Then 10 uL of Varify 1 (pooled normal plasma from Organon Teknika Corp.) was mixed with 90 uL of diluted TFPI samples in a sample tray and warmed to 37° C. in the instrument. Finally Simplastin Excel (Thromboplastin from Organon Teknika Corp.) was added to start the clotting. The time delay in clotting due to anticoagulant activity of TFPI was measured and converted into TFPI concentration in the measured samples by comparison to a TFPI standard curve.

TFPI may be prepared by recombinant methods as disclosed in U.S. Pat. No. 5,212,091, the disclosure of which is herein incorporated by reference. Briefly, TFPI is expressed in *Escherichia coli* cells and the inclusion bodies containing TFPI are isolated from the rest of the cellular material. The inclusion bodies are subjected to sulfitolysis, purified using ion exchange chromatography, refolded by disulfide interchange reaction and the refolded, active TFPI purified by cation exchange chromatography. TFPI may also be puroduced in yeast as disclosed in U.S. Pat. No. 6,103,500.

The amount of soluble TFPI may also be quantified by measuring the area of the main peak on a cation exchange chromatogram. HPLC analysis of TFPI samples was performed using a Waters 626 LC system (Waters Corporation, Milford, Mass.) equipped with a Water 717 plus heater/cooler autosampler. Data acquisition was processed by a Turbochrom™ system from Perkin-Elmer.

The cation exchange (EX) method used a Pharmacia Mono S HR 5/5 glass column. The column was equilibrated in 80% buffer A (20 mM sodium acetate trihydrate:acetonitrile solution (70:30 v/v) at pH 5.4) and 20% buffer B (20 mM sodium acetate trihydrate—1.0 M ammonium chloride:acetonitrile solution (70:30 v/v) at pH 5.4). After a sample was injected, a gradient was applied to elute the TFPI at a flow rate of 0.7 mL/min from 20% buffer B to 85% buffer B in 21 minutes. Eluting TFPI species were detected by absorbance at 214 nm. The main peak (monomer TFPI) was found to elute at about 18 minutes. Loss of soluble TFPI was quantified by integrating remaining peak area of the main peak.

All reagents are U.S.P. or A.C.S. grade. Suppliers include J. T. Baker and Sigma Co. (St. Louis, Mo.).

The present invention will now be illustrated by reference to the following examples, which set forth certain embodiments. However, it should be noted that these embodiments are illustrative and are not to be construed as restricting the invention in any way.

EXAMPLES

Example 1

Refolding Denatured TFPI

The following example describes the making of stock solutions, the HIC column preparation, the initial recovery and purification of TFPI prior to refolding, the refolding of TFPI, and the recovery of active TFPI.

The TFPI stock was prepared from refractile bodies resulting from the expression of recombinant TFPI in bacteria. The retractile bodies were solubilized at 10 mg/ml in 8 M urea, 50 mM Tris pH 8.5 containing 10 mM DTT, and this solution was clarified by centrifugation at 10,000×g for 10 minutes.

The column preparation for the initial purification of the solubilized TFPI was prepared with S-Sepharose beads mixed in 7.5 M urea, 10 mM Tris and 10 mM sodium phosphate (pH 6.5) containing 5 mM DTT and 1 mM EDTA. The solubilized TFPI at a concentration of 5 mg/ml was then run over the S-Sepharose column and eluted with a sodium chloride gradient of 0 to 1 M. The purified TFPI had an absorbency at wavelength 280 nm of 3.2 (which is equivalent to 4.1 mg/ml using an extinction coefficient of 0.78).

The dextran sulfate stock consisted of dextran sulfate of molecular weight 8000 daltons available from Sigma, item number D-4911, made up at 50 mg/ml (6.25 mM) in 50 mM Tris (pH 8.8) in 0.1 M sodium chloride, and stored at −20 degrees centigrade between uses.

The heparin stock, if heparin was used to conduct the refolding, was of molecular weight 6000 to 30,000 daltons, (with an average molecular weight of 18,000 daltons) prepared as a sodium salt available from Sigma Co. (St. Louis, Mo.), item number H-3393, made up at 60 mg/ml (3.33 mM) in 50 mM Tris (pH8.8) in 0.1 sodium chloride, and stored at −20° centigrade between uses.

To the S-Sepharose purified TFPI either dextran sulfate stock solution or heparin stock solution can be added. Dextran or heparin was added to TFPI under denaturing conditions in 6 to 8 M urea. With 4° C. reagents, the denaturing solution containing TFPI was diluted to 3 M urea, 50 mM Tris (pH 8.8), 0.2 M sodium chloride, and 0.5 mg/ml TFPI, and to a final dextran sulfate concentration of 0.6 mg/ml (75 µM) or a final heparin concentration of 1.5 mg/ml (83 µM), depending on which was used to facilitate the refolding. Cystine was added to the refolding solution to a final concentration equal to the final DTT concentration. The refolding solution was incubated at 4° C. with gentle agitation for from 4 to 6 days, preferably 5 days.

As an illustration of this procedure the following is a detail of a protocol for refolding a 5 ml solution of TFPI in dextran sulfate or heparin.

To 610 µl of TFPI stock either 60 µl of dextran sulfate with 65 µl of 50 mM Tris (pH 8.8) in 0.1 M NaCl, or 125 µl of heparin stock solution with 50 mM Tris (pH 8.8) or 0.1 M NaCl was added. The refolding solution was mixed and allowed to incubate 10 minutes on ice. Next, 4.2 ml of refolding buffer containing 2.5 M urea, 50 mM Tris (pH 8.8) and 165 mM sodium chloride was added to the refolding solution and mixed. Finally, 61 µl of 50 mM Cystine made up in 120 mM sodium hydroxide was added and the total solution was incubated at 4° C. with gentle agitation for 4 days. The free sulfhydryl content was checked with Ellman's reagent (also called DTNB). Idoacetamide was added, to 20 mM, made up at 1 M in 100% ethanol for storage at −20° C.

The hydrophobic interaction column (HIC) was prepared from Butyl-650M Tosohaas Toyopearl resin particle size 40–90, part # 014702. The butyl resin was washed in 3 M urea, 1 M ammonium sulfate, 50 mM Tris, 10 mM sodium phosphate, pH 6.5 and resuspended at a 50% slurry.

The refolding samples, stored at −20° C. remained in the standard refolding buffer containing 3 M urea, 50 mM Tris, pH 8.8, 1–4 mM redox, 0.5 mg/ml TFPI and 0.2–0.6 M NaCl depending on condition. Samples refolded with dextran or heparin had 0.2 M salt, and samples without dextran or heparin had 0.6 M NaCl.

The following steps were performed at room temperature to effect the further purification of the refolded TFPI. To 300 µl of refolded sample, an equal volume of 2 M ammonium sulfate, 3 M urea, 50 mM Tris, and 10 mM sodium phosphate (pH 6.5) was added. Next, 100 µl of washed Butyl-650M beads was added to the diluted refolded sample. The solution with the beads was incubated with gentle rocking or mixing for 30 minutes at room temperature. The mix was then spun in an ependorf centrifuge for 5 seconds, and put in a rack and allowed to sit for one minute for the beads to settle flat in the tube. The supernatant was aspirated carefully, so as not to disturb the beads.

To wash the TFPI-bound beads, 1 ml of wash buffer composed of 1 M ammonium sulfate, 3 M urea, 50 mM Tris, 10 mM sodium phosphate (pH 6.5) was added to the beads to remove the remaining dextran sulfite or heparin. The washed mixture was re-spun in an ependorf centrifuge for 5 seconds, and allowed to sit for one minute for the beads to settle as before. The supernatant was removed, and the beads then washed with the wash buffer a final time, and spun and allowed to sit as before. After the final wash and sealing, the supernatant was removed with a flame-pulled-tip Pasteur pipette very carefully.

To elute the refolded TFPI, 300 µl of elution buffer composed of 3 M urea, 0.1 M ammonium sulfite, 50 mM Tris and 10 mM sodium phosphate (pH 6.5) was added to the slurry of beads and rocked for more than 10 minutes. The beads were pelleted by spinning in an ependorf centrifuge, and the supernatant containing refolded TFPI was recovered. To avoid contamination of the beads with the product, some of the supernatant was left behind.

Example 2

HIC of Dextran Sulfate Refold

Figure 2:
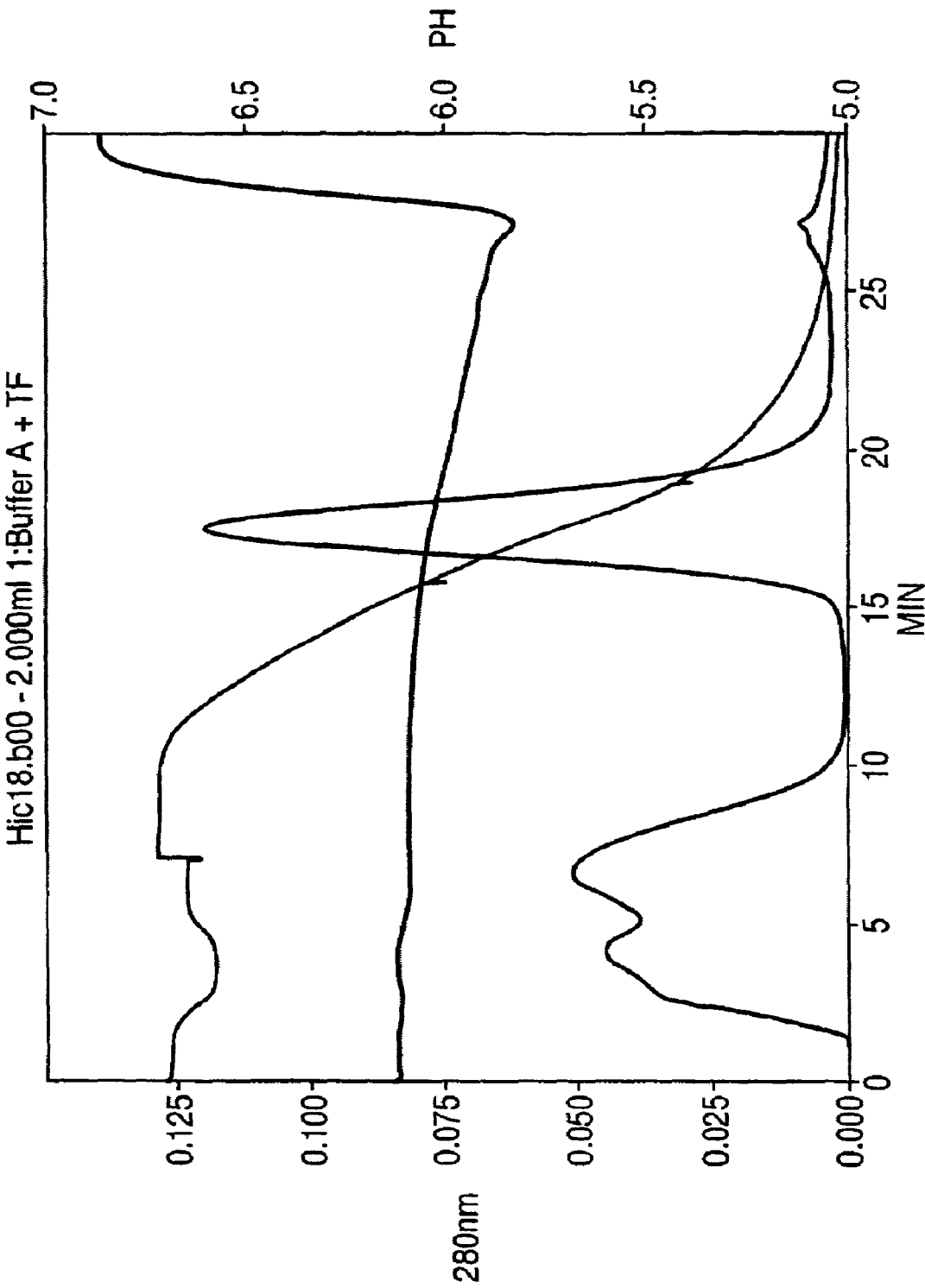
FIG. 2 is a plot of the recovery of native TFPI from the HIC column.

The sample of TFPI was renatured at a concentration of 0.5 mg/ml TFPI, 0.6 mg/ml Dextran sulfate, 3.0 M Urea, 200 mM NaCl and 50 mM Tris (pH 5.5). The HIC column was prepared from TosoHaas Butyl beads for HIC, 4.6 mmD/100 mmL, in a 1.66 ml slurry. The flow rate was set for 1.0 ml/min. Before loading the HIC column, the sample was diluted 2:3 with 3.0 M Urea and 3.0 M $NH_4SO_4$ at a final pH of 5.68; 2 ml of sample was loaded. The gradient start was 33 mM MES/33 nm HEPES/33 mM sodium acetate, 1.0 M NH$_4$SO$_4$, and 3.0 M Urea, pH 6.0; the gradient end was 33 mM MES/33 mM HEPES/33 mM sodium acetate, 3.0 M Urea at pH 6.0. The gradient volume was 5.0 CV. From this column, the recovery of native TFPI was 68%. The results of this run are shown in FIG. 2.

Figure 3:
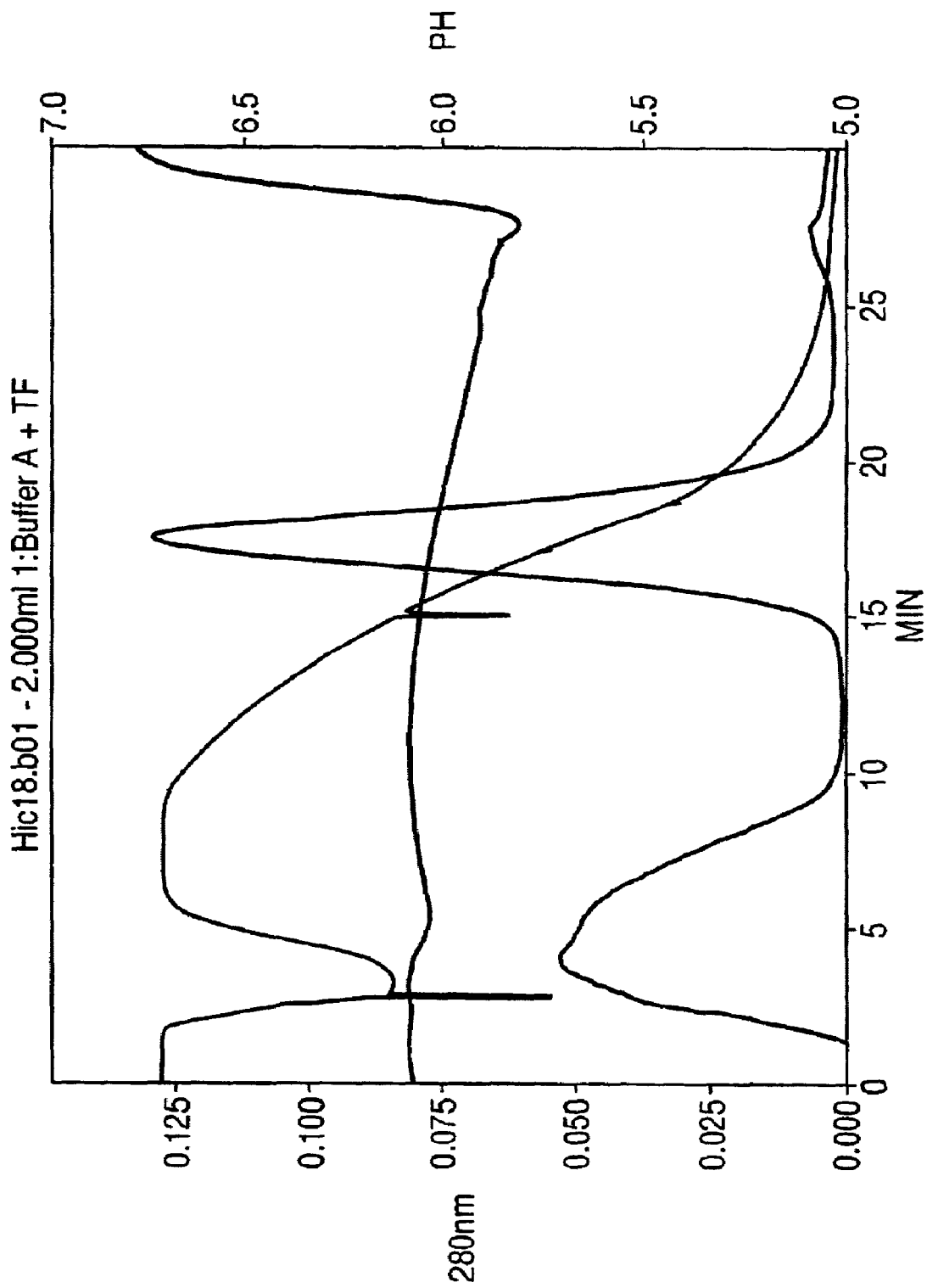
FIG. 3 is a plot of the recovery of native TFPI from a second HIC column.

A second HIC column was also run. The sample of denatured TFPI was diluted 2:3 with 3.0 M Urea, 1.5 M NH$_4$SO$_4$ and two ml were loaded. The gradient start was 33 mM MES/33 HEPES/33 nm sodium acetate, 0.5 M NH$_4$SO$_4$, and 3.0 M Urea, pH 6.0; the gradient end was 33 mM MES/33 mM HEPES/33 mM sodium acetate, 3.0M Urea at pH 6.0. The gradient volume was 5.0 CV. The recovery of native TFPI from this second column was 74%. The results of this run are shown in FIG. 3.

Figure 1:
FIG. 1 is a coomassie stained SDS-PAGE analysis of TFPI peak fractions from the Phenyl Sepharose HIC refolding procedure.

The samples were analyzed by non-reducing SDS-PAGE as illustrated in FIG. 1. Correctly refolded, active TFPI species (major band) are seen on the gel.

Example 3

About 10 mg/mL TFPI in 2M urea was dialyzed against one of the following: 20 mM acetate, 20 mM phosphate, 20 mM citrate, 20 mM glycine, 20 mM L-glutamate or 20 mM succinate in 150 mM NaCl as described above. 6–10 mg/mL TFPI bulk stock was loaded into Spec/Por 7 dialysis tubings (MW cutoff 3,500). Dialysis was carried out either at 4° C. or ambient temperature. Three changes of buffer at a protein solution to buffer ratio: 1 to 50–100, were made during course of dialysis over 12 to 24 hr time period. After dialysis, TFPI solution was filtered by Costar 0.22 micron filter units to separate precipitated TFPI from soluble TFPI. The solubility of TFPI was then measured by UV/V is absorbance assuming an absorptivity 0.68 (mg/mL)$^{-1}$ cm$^{-1}$ at 278 nm. The solutions were prepared at various pH levels by titration with HCl or NaOH.

Figure 5:
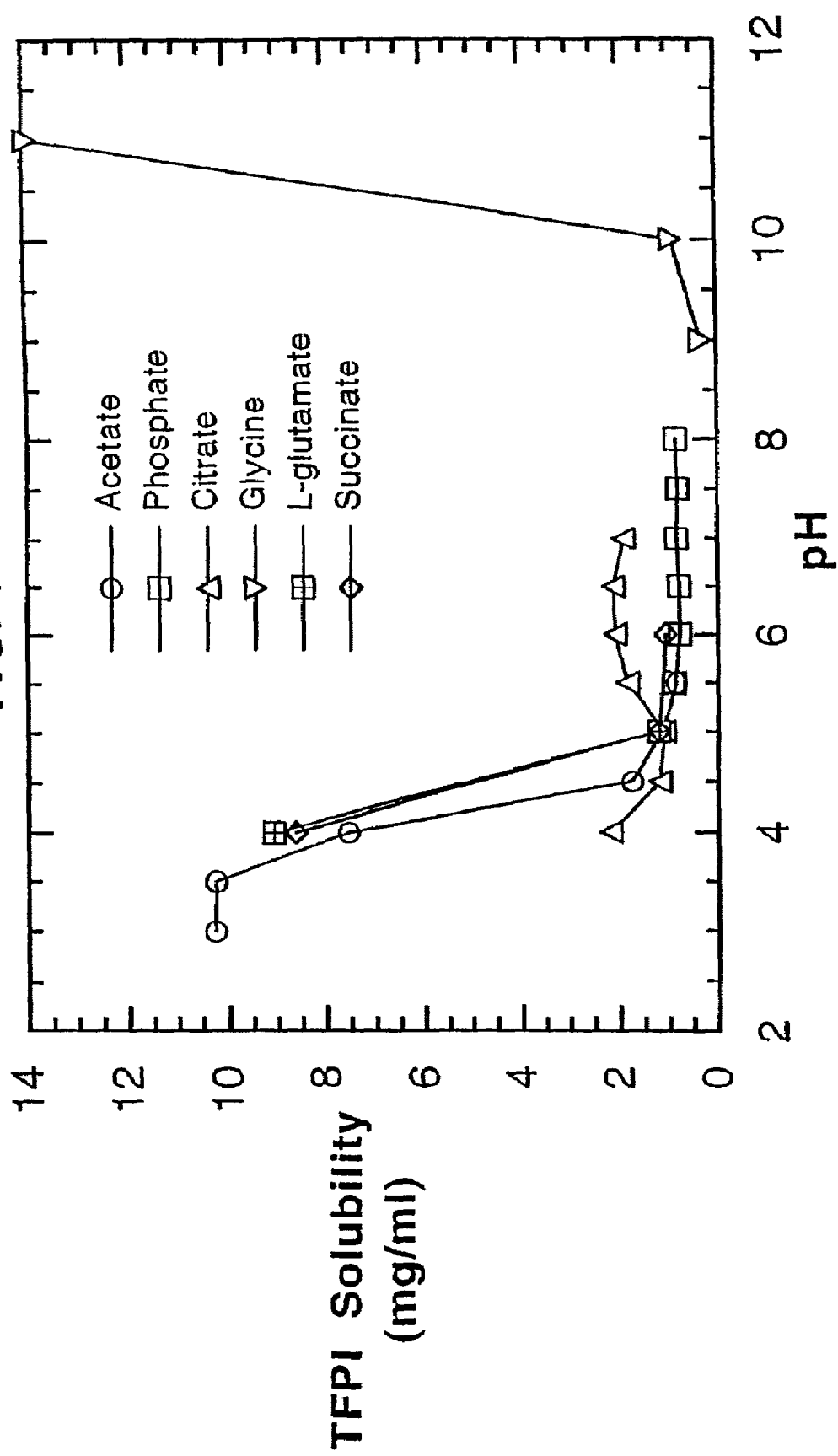
FIG. 5 shows the solubility of TFPI at different pH conditions. About 10 mg/mL TFPI in 2M urea was dialyzed against 20 mM acetate, phosphate, citrate, glycine, L-glutamate or succinate in 150 mM NaCl. The concentration of remaining soluble TFPI after dialysis was measured by UV absorbance after filtering out the precipitates through 0.22 mm filter units.
Figure 6:
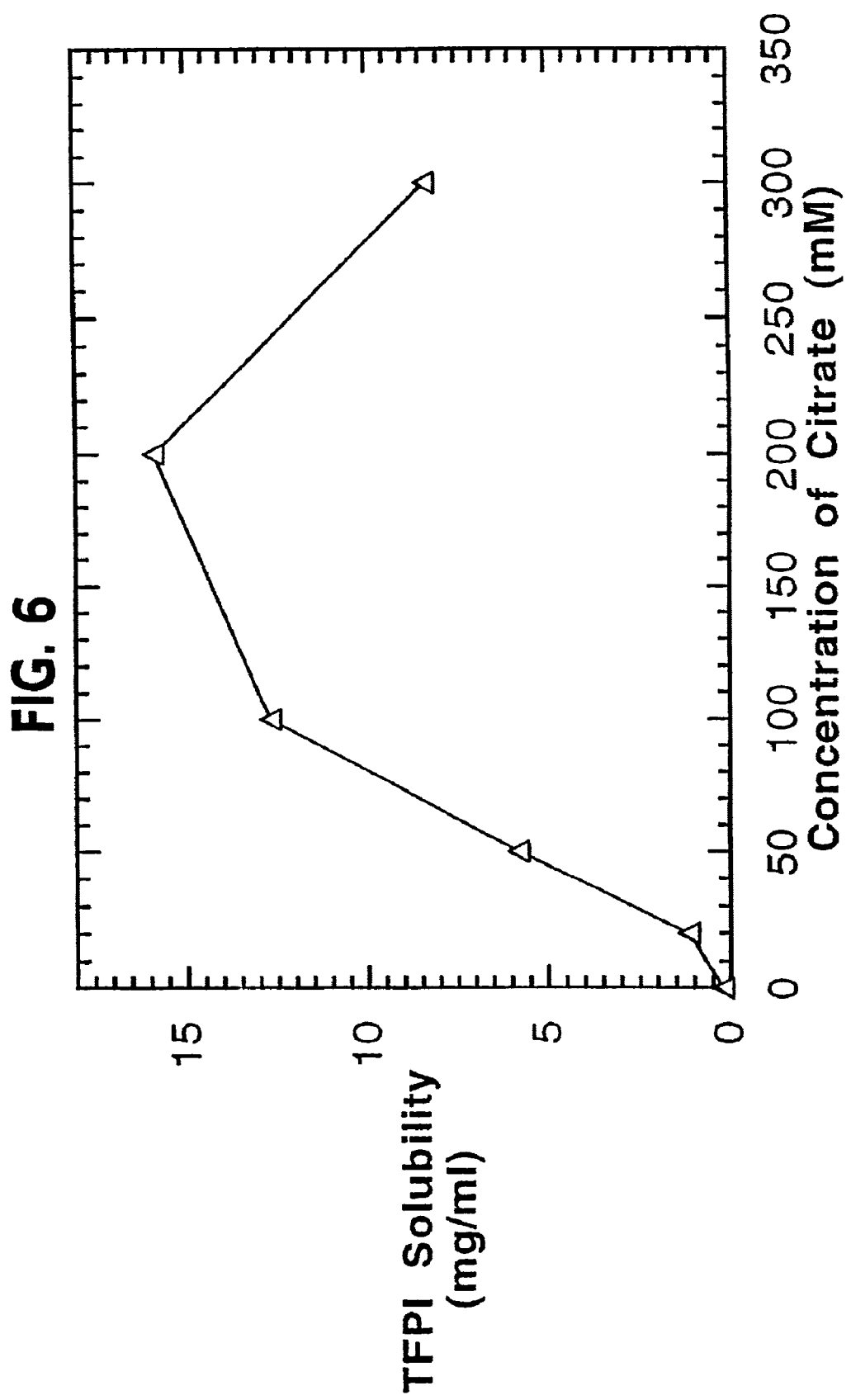
FIG. 6 shows the solubility of TFPI as a function of concentration of citrate in the presence of 10 mM Na phosphate at pH 7. TFPI solubility increases with increasing concentration of citrate.
Figure 7:
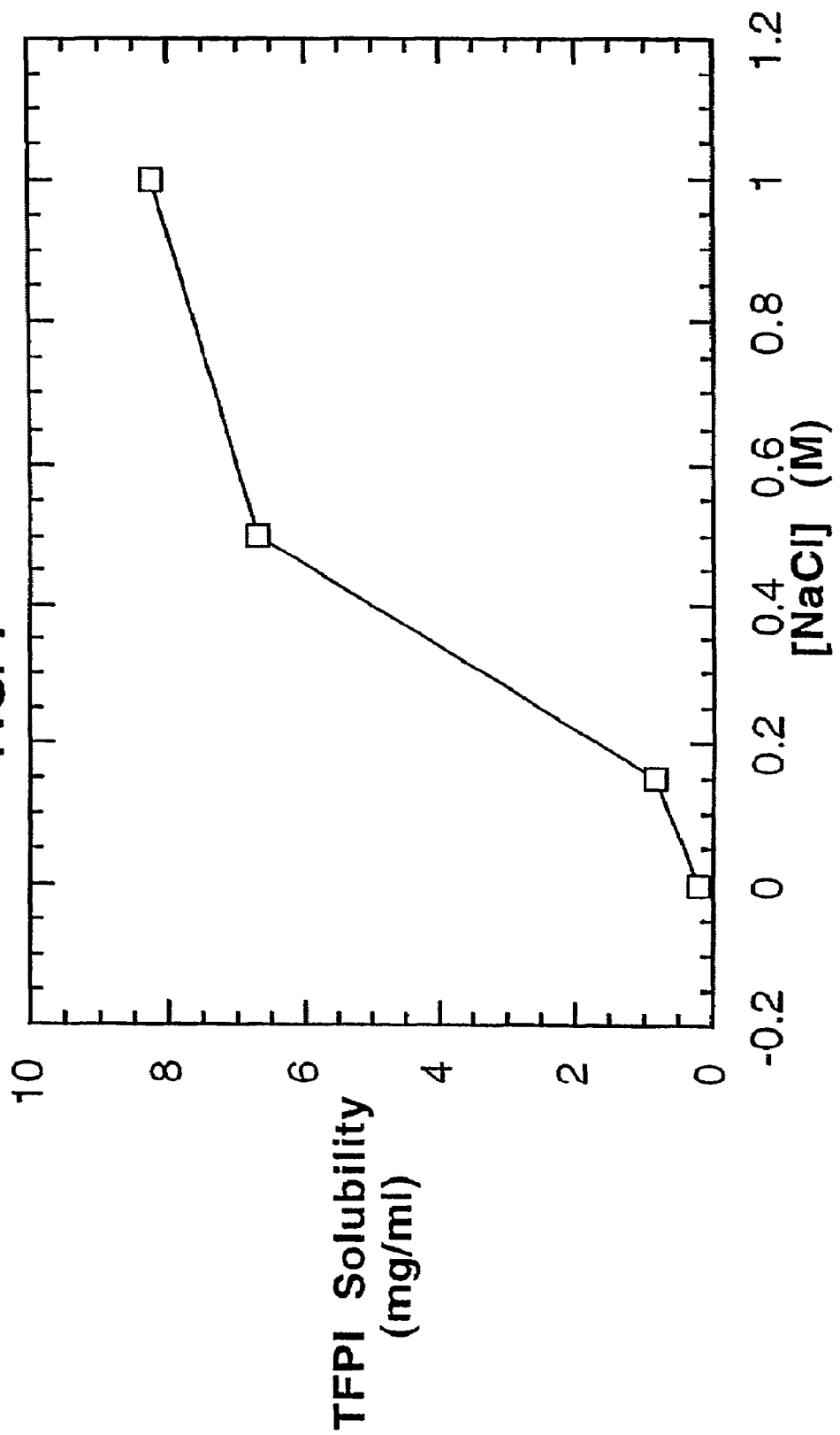
FIG. 7 shows the solubility of TFPI as a function of concentration of NaCl. TFPI solubility increases with increasing salt concentration, indicating salt promotes solubility of TFPI.

After completion of dialysis, the precipitates were filtered through 0.22 μm filter units. The concentration of remaining soluble TFPI after dialysis was measured by UV absorbance. FIG. 5 shows the results of these experiments. Solubility of TFPI increased greatly in solutions containing 20 mM acetate, 20 mM phosphate, 20 mM L-glutamate and 20 mM succinate at pH levels below 7 and particularly at or below pH 4.5. Solubility of TFPI was also substantially increased in solutions containing 20 mM glycine above pH 10. FIG. 6 shows the solubility of TFPI as a function of concentration of citrate ion in the presence of 10 mM Na phosphate at pH 7. TFPI solubility increases with increasing concentration of citrate. FIG. 7 shows the solubility of TFPI as a function of concentration of NaCl at pH 7.0. TFPI solubility increases with increasing salt concentration, indicating salt promotes solubility of TFPI.

The solubility of TFPI was studied using a number of different solubilizers and secondary solubilizers. Table 1 shows solubility of TFPI in varying buffer solutions measured by UV absorbance after dialyzing 6 to 10 mg/mL TFPI into these buffer solutions.

TABLE 1

| Content | pH | Solubility c (mg/ml) uv |
|---|---|---|
| Salt effect | | |
| 10 mM NaPO4, | 7 | 0.21 |
| 10 mM NaPO4, 150 mM NaCl | 7 | 0.72 |
| 20 mM NaPO4, 150 mM NaCl | 7 | 0.85 |
| 20 mM NaPO4, 0.5 M NaCl | 7 | 6.71 |
| 20 mM NaPO4, 1 M NaCl | 7 | 8.24 |

TABLE 1-continued

| Content | pH | Solubility c (mg/ml) uv |
|---|---|---|
| pH effect | | |
| 20 mM NaOAc, 150 mM NaCl | 3 | 10.27 |
| 20 mM NaOAc, 150 mM NaCl | 3.5 | 10.25 |
| 20 mM NaOAc, 150 mM NaCl | 4 | 7.54 |
| 20 mM NaOAc, 150 mM NaCl | 4.5 | 1.75 |
| 20 mM NaOAc, 150 mM NaCl | 5 | 1.15 |
| 20 mM NaOAc, 150 mM NaCl | 5.5 | 0.85 |
| 20 mM NaPO4, 150 mM NaCl | 5.5 | 0.89 |
| 20 mM NaPO4, 150 mM NaCl | 6 | 0.78 |
| 20 mM NaPO4, 150 mM NaCl | 6.5 | 0.79 |
| 20 mM NaPO4, 150 mM NaCl | 7 | 0.85 |
| 20 mM NaPO4, 150 mM NaCl | 7.5 | 0.82 |
| 20 mM NaPO4, 150 mM NaCl | 8 | 0.86 |
| 20 mM NaCitrate, 150 mM NaCl | 4 | 2.17 |
| 20 mM NaCitrate, 150 mM NaCl | 4.5 | 1.19 |
| 20 mM NaCitrate, 150 mM NaCl | 5 | |
| 20 mM NaCitrate, 150 mM NaCl | 5.5 | 1.84 |
| 20 mM NaCitrate, 150 mM NaCl | 6 | 2.09 |
| 20 mM NaCitrate, 150 mM NaCl | 6.5 | 2.12 |
| 20 mM NaCitrate, 150 mM NaCl | 7 | 1.92 |
| 20 mM Glycine, 150 mM NaCl | 9 | 0.32 |
| 20 mM Glycine, 150 mM NaCl | 10 | 0.9 |
| 20 mM Glycine, 150 mM NaCl | 11 | 13.94 |
| 20 mM L-Glutamate, 150 mM NaCl | 4 | 9.07 |
| 20 mM L-Glutamate, 150 mM NaCl | 5 | 1.21 |
| 20 mM Succinate, 150 mM NaCl | 4 | 8.62 |
| 20 mM Succinate, 150 mM NaCl | 5 | 1.21 |
| 20 mM Succinate, 150 mM NaCl | 6 | 1.07 |
| Citrate | | |
| 10 mM NaPO4, 20 mM NaCitrate | 7 | 1.16 |
| 10 mM NaPO4, 50 mM NaCitrate | 7 | 5.81 |
| 10 mM NaPO4, 100 mM NaCitrate | 7 | 12.7 |
| 10 mM NaPO4, 200 mM NaCitrate | 7 | 15.9 |
| 10 mM NaPO4, 300 mM NaCitrate | 7 | 8.36 |
| Mg2+, Ca2+ and polyphosphate | | |
| 10 mM NaPO4, 150 mM NaCl, 1 mM MgCl2 | 7 | 0.66 |
| 10 mM NaPO4, 150 mM NaCl, 10 mM MgCl2 | 7 | 1.02 |
| 10 mM NaPO4, 150 mM NaCl, 0.1 mM CaCl2 | 7 | 0.67 |
| 10 mM NaPO4, 150 mM NaCl, 1 mM CaCl2 | 7 | 0.71 |
| 10 mM NaPO4, 150 mM NaCl, 10 mM triphosphate | 7 | 3.64 |
| 10 mM NaPO4, 5% PEG-400 | 7 | 0.07 |
| 10 mM NaPO4, 10 mM EDTA | 7 | 0.36 |
| 10 mM NaPO4, 100 mM Na2SO4 | 7 | 5.08 |
| 10 mM NaPO4, 100 mM L-aspartic acid | 7 | 0.4 |
| 10 mM NaPO4, 100 mM Succinic acid | 7 | 2.33 |
| 10 mM NaPO4, 100 mM Tartaric acid | 7 | 2.56 |
| 20 mM NaPO4, 100 mM Maleic acid | 7 | 0.11 |
| 20 mM NaPO4, 100 mM Malic acid | 7 | 1.87 |
| 10 mM NaPO4, 100 mM L-glutamic acid | 7 | 0 |
| 10 mM NaPO4, 150 mM NaCl | 7 | 0.25 |
| 10 mM NaPO4, 100 mM isocitrate | 7 | 10.83 |
| NaOAc, NaPO4 and NaCl | | |
| 10 mM NaOAc, 150 mM NaCl | 4.5 | 1.76 |
| 10 mM NaOAc | 4.5 | 4.89 |
| 10 mM NaOAc | 5.5 | 4.95 |
| 10 mM NaOAc | 6.5 | 5.1 |
| 10 mM NaOAc | 7 | 5.87 |
| 10 mM NaPO4, 150 mM NaCl | 4.5 | 0.14 |
| 10 mM NaPO4 | 4.5 | 4.97 |
| 10 mM NaPO4 | 5.5 | 0.79 |
| 10 mM NaPO4 | 6.5 | 0.091 |
| 10 mM NaPO4 | 7 | 0.94 |
| 50 mM NaOAc | 5 | 5.24 |
| 5 mM NaOAc | 5.5 | 4.59 |
| 10 mM NaOAc | 5.5 | 5.05 |
| 20 mM NaOAc | 5.5 | 5.04 |
| 50 mM NaOAc | 5.5 | 5.71 |
| 100 mM NaOAc | 5.5 | 1.4 |
| 200 mM NaOAc | 5.5 | 1.32 |
| 5 mM NaOAc, 5 mM NaCl | 5.5 | 4.85 |
| 5 mM NaOAc, 10 mM NaCl | 5.5 | 5.04 |
| 5 mM NaOAc, 50 mM NaCl | 5.5 | 0.56 |

TABLE 1-continued

| Content | pH | Solubility c (mg/ml) uv |
|---|---|---|
| 5 mM NaOAc, 100 mM NaCl | 5.5 | 0.43 |
| 5 mM NaOAc, 200 mM NaCl | 5.5 | 0.8 |
| 5 mM NaOAc | 4.5 | 7.27 |
| 10 mM NaOAc | 4.5 | 6.5 |
| 20 mM NaOAc | 4.5 | 8.32 |
| 50 mM NaOAc | 4.5 | 9.17 |
| 5 mM NaOAc | 5.5 | 8.98 |
| 10 mM NaOAc | 5.5 | 8.08 |
| 20 mM NaOAc | 5.5 | 8.99 |
| 50 mM NaOAc | 5.5 | 2.92 |
| 5 mM NaOAc, 150 mM NaCl | 4.5 | 2.6 |
| 10 mM NaOAc, 150 mM NaCl | 4.5 | 2.59 |
| 20 mM NaOAc, 150 mM NaCl | 4.5 | 2.55 |
| 50 mM NaOAc, 150 mM NaCl | 4.5 | 2.1 |
| 5 mM NaOAc, 150 mM NaCl | 5.5 | 0.65 |
| 10 mM NaOAc, 150 mM NaCl | 5.5 | 0.69 |
| 20 mM NaOAc, 150 mM NaCl | 5.5 | 0.74 |
| 50 mM NaCAc, 150 mM NaCl | 5.5 | 0.91 |
| Hydrophobic chain length | | |
| 10 mM NaPO4, 50 mM Formic acid | 7 | 0.12 |
| 10 mM NaPO4, 50 mM Acetic acid | 7 | 0.16 |
| 10 mM NaPO4, 50 mM Propanoic acid | 7 | 0.16 |
| 10 mM NaPO4, 50 mM Butanoic acid | 7 | 0.13 |
| 10 mM NaPO4, 50 mM Pentanoic acid | 7 | 0.14 |
| 10 mM NapO4, 50 mM Hexanoic acid | 7 | 0.11 |
| Others | | |
| 20 mM NaOAc, 3% Mannitol, 2% Sucrose, 5% PEG-400 | 4 | 19.9 |
| 20 mM Na Citrate, 3% Mannitol, 2% Sucrose, 5% PEG-400 | 6.5 | 0.72 |
| 20 mM Na Citrate, 150 mM NaCl, 5% PEG-400 | 6.5 | 2.18 |
| 20 mM NaOAc, 150 mM NaCl, 5% PEG-400 | 4 | 19.8 |
| 20 mM Na Citrate, 130 mM NaCl, 1% Glycine, 0.25% Tween-80, 5% PEG-400 | 6.5 | 1.48 |
| 20 mM Na Citrate, 130 mM NaCl, 1% Glycine, 0.25% Tween-80 | 6.5 | 1.32 |
| 5 mM NaAcetate | 5.5 | 8.9 |
| 5 mM NaAcetate, 8% Sucrose | 5.5 | 11 |
| 5 mM NaAcetate, 0.01% Polysorbate-80 | 5.5 | 7 |
| 5 mM NaAcetate, 8% Sucrose, 0.01% Polysorbate-80 | 5.5 | 12 |
| 10 mM NaAcetate | 5.5 | 7.6 |
| 10 mM NaAcetate, 8% Sucrose | 5.5 | 10 |
| 10 mM NaAcetate, 8% Sucrose, 0.01% Polysorbate-80 | 5.5 | 12.1 |
| 5 mM NaAcetate, 5% Sorbitol | 5.5 | 7.8 |
| 5 mM NaAcetate, 4.5% Mannitol | 5.5 | 9.2 |
| 5 mM Histidine | 6 | 5.5 |
| 5 mM Histidine | 6.5 | 1 |
| 5 mM NaCitrate | 5.5 | 0.1 |
| 5 mM NaCitrate | 6 | 0.1 |
| 5 mM NaCitrate | 6.5 | 0.1 |
| 5 mM NaSuccinate | 5.5 | 0.6 |
| 5 mM NaSuccinate | 6 | 0.3 |
| 5 mM NaSuccinate | 6.5 | 0.2 |
| 10 mM Imidazole | 6.5 | 2.5,10.8 |
| 10 mM Imidazole | 7 | 0.8 |
| 10 mM Imidazole, 8% Sucrose | 6.5 | 12.2 |
| 5 mM NaAcetate | 6 | 8.2 |
| 10 mM Imidazole, 5 mM NaAcetate | 6.5 | 12.8 |
| 10 mM NaCitrate | 6 | 0.2 |
| 100 mM NaCitrate | 6 | 8.1 |
| 100 mM NaCitrate | 7 | 9.3 |
| 10 mM Naphosphate, 260 mM Na2SO4 | 6 | 9.1 |
| 10 mM NaPhosphate, 100 mM NaCitrate | 8 | 8.8 |
| 10 mM NaCitrate, 1% L-glutamic acid | 6 | 4.6 |
| 10 mM NaCitrate, 2% L-lysine | 6 | 1.1 |
| 10 mM NaCitrate, 0.5% L-aspartic acid | 6 | 0.4 |
| 10 mM NaCitrate, 0.1% Phosphate glass | 7 | 5.9 |
| 10 mM Tris, 100 mM NaCitrate | 8 | 8.5 |
| 10 mM NaCitrate, 1 M Glycine | 6 | 0.3 |
| 10 mM NaCitrate, 300 mM Glycine | 6 | 0.3 |
| 10 mM NaCitrate, 280 mM Glycerol | 6 | 0.3 |
| 10 mM NaCitrate, 0.5 M (NH4)2SO4 | 6 | 8.3 |
| 10 mM NaCitrate, 120 mM (NH4)2SO4 | 6 | 8.8 |
| 10 mM NaCitrate, 260 mM Na2SO4 | 6 | 9.4 |
| 10 mM NaPO4, 0.1% Phosphate glass | 7 | 15.8 |
| 10 mM NaCitrate, 0.1% SDS | 6 | 11.2 |
| 10 mM NaCitrate, 0.02% SDS | 6 | 7.8 |
| 10 mM NaAcetate, 8% PEG-400 | 5.5 | 13.7 |
| 10 mM NaAcetate, 150 mM NaCl, 8% PEG-400 | 5.5 | 0.6 |
| 10 mM NaAcetate, 8% PEG-400 | 6 | 16.2 |
| 10 mM NaCitrate, 8% PEG-400 | 6 | 0.2 |

Example 4

Figure 8:
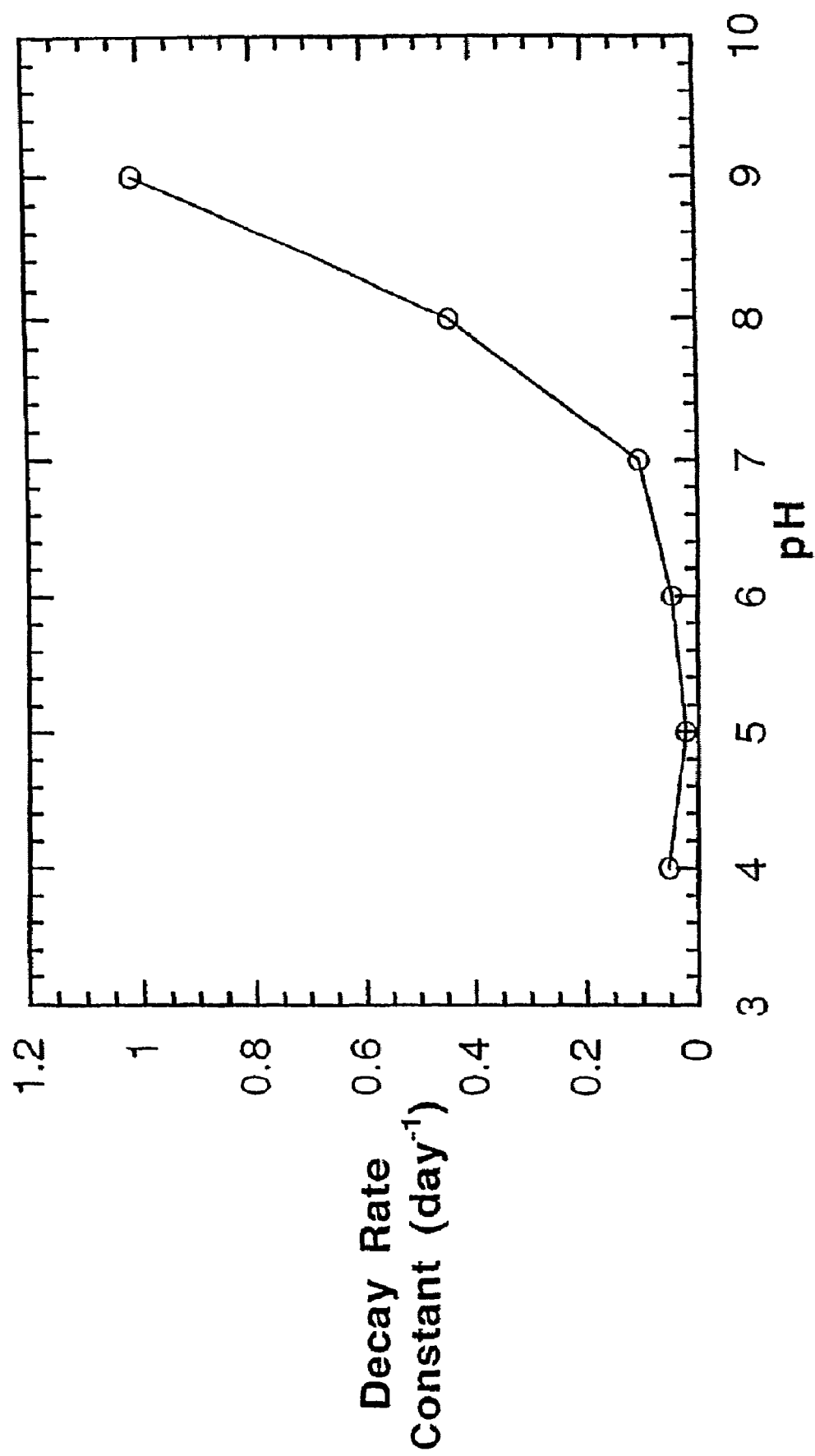
FIG. 8 shows effect of pH on the stability of TFPI prepared in 10 mM Na phosphate, 150 mM NaCl and 0.005% (w/v) polysorbate-80. Stability samples containing 150 µg/mL TFPI were incubated at 40° C. for 20 days.

The stability of TFPI stored at various pH conditions was tested. TFPI was prepared by dialysis as above in 10 mM Na phosphate, 150 mM NaCl and 0.005% (w/v) polysorbate-80. Stability samples containing 150 mg/mL TFPI were incubated at 40° C. for 20 days. Kinetic rate constant for the remaining soluble TFPI was analyzed by following decrease of the main peak on cation exchange chromatograms. As can be seen in FIG. 8, the decay rate constant increases at pH above 6.0, indicates more aggregation at higher pH conditions.

Figure 9A:
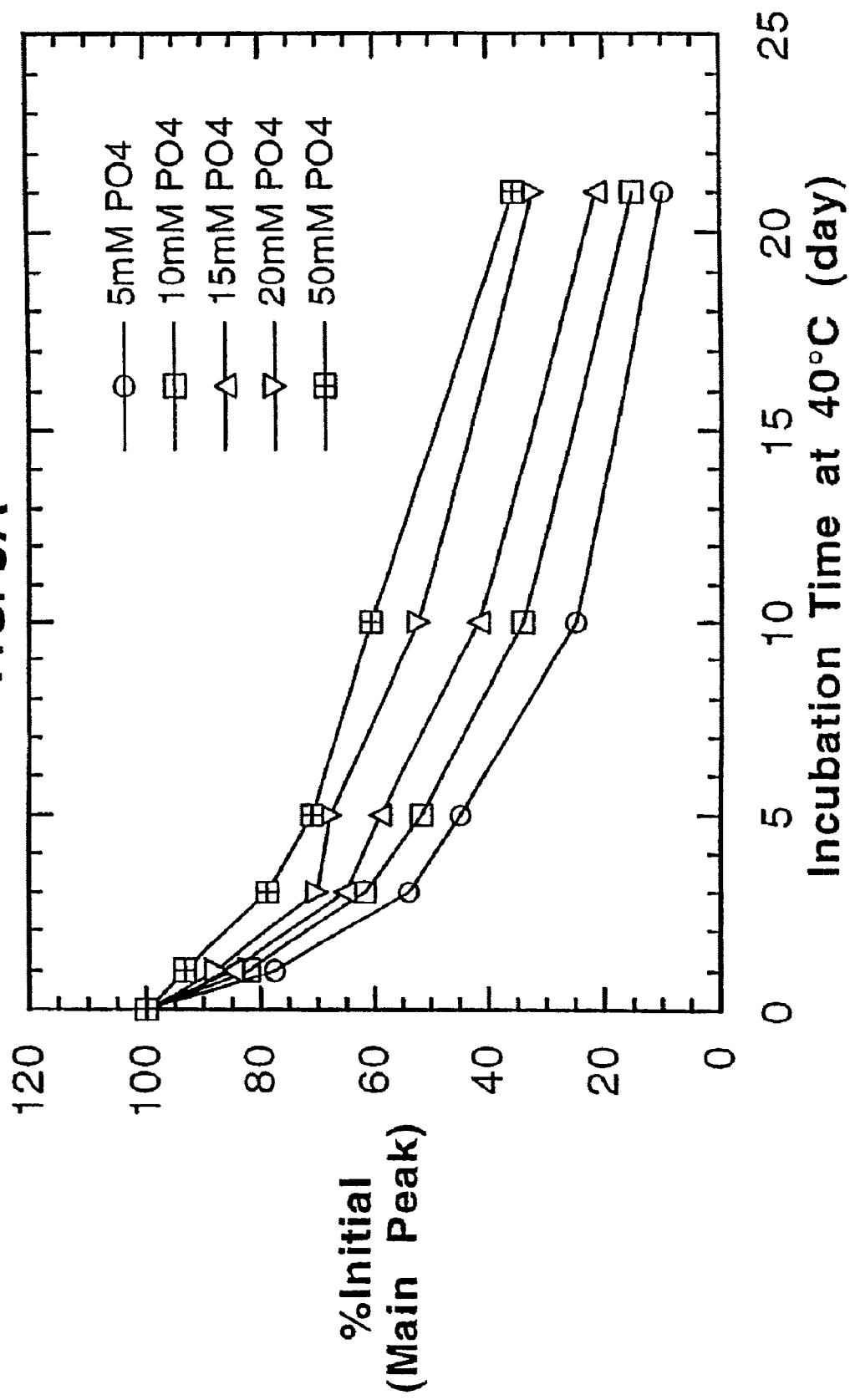

TFPI was also formulated at a concentration of 150 mg/mL in 150 mM NaCl and 0.005% (w/v) polysorbate-80 at pH 7 with varying concentrations of phosphate. FIG. 9A shows the percentage of remaining soluble TFPI measured by the cation exchange HPLC. Increasing concentrations of phosphate ion in solution resulted in higher levels of soluble TFPI remaining after incubation at 40° C. Higher levels of phosphate ion also resulted in higher levels of active TFPI as assayed by the prothrombin time assay. These results are shown in FIG. 9B.

Stability of TFPI at a concentration of 0.5 mg/mL and formulated in 10 mM Na citrate, pH 6 and 150 mM NaCl was also tested at 40° C. over a 40 day period. As seen in FIG. 10, cation-exchange HPLC (triangle) shows the presence of soluble TFPI at levels greater than 60% initial, even after the 20 day incubation. In like manner, the prothrombin time assay (circle) shows the presence of active TFPI at levels greater than 60% initial, even after the 20 day incubation.

FIG. 11 shows loss of soluble TFPI at 40° C. measured by both cation-exchange HPLC (open symbol) and prothrombin time assay (closed symbol) for 0.5 mg/mL TFPI formulated in 10 mM Na phosphate, pH 6 and either 150 mM NaCl (triangle) or 500 mM NaCl (circle).

FIG. 12 shows loss of soluble TFPI at 40° C. measured by both cation-exchange HPLC (open symbol) and prothrombin time assay (closed symbol) for 0.5 mg/mL TFPI formulated in 10 mM Na acetate and pH 5.5 containing 150 mM NaCl (triangle) or 8% (w/v) sucrose (square) or 4.5% (w/v) mannitol (circle).

FIG. 13 shows two non-reducing SDS gels for TFPI formulation samples in 10 mM Na$_3$PO$_4$, 150 mM NaCl, and 0.005% polysorbate-80 at pH 4 to pH 9 stored at 40° C. for 0 days (lower) and 20 days (upper). No loss on TFPI is seen at 0 days. However, at 20 days cleavage fragments of TFPI may be seen at the lower pH range (i.e. pH 4 and pH 5). Without being bound to a particular theory, it is believed that these fragments may result from an acid catalyzed reaction.

Finally, Table 2 shows the half-life of remaining soluble TFPI at 40° C. for various formulations. 0.5 mg/mL TFPI was formulated in these formulation conditions and incubated at 40° C. Samples were withdrawn at predetermined time intervals and loss of soluble and active TFPI were examined by the IEX-HPLC and the PT assay. Half-life for remaining soluble TFPI was then calculated by performing a single exponential fitting to the IEX-HPLC and PT assay results.

Example 5

Elution of TFPI in displacement mode from chromatography resins using polyionic compounds.

TFPI is first bound to a resin in a low salt buffer. Next a buffer containing the polyionic compound used to elute TFPI in displacement mode, is pumped through the column. This compound binds stronger to the resin tan TFPI and displaces TFPI. For a positively charged resin (anion exchanger) a negatively charged compound is used and for a negatively charged resin (cation exchanger) a positively charged compound is used.

Partially purified TFPI was used as starting material. TFPI, in 6 M urea, 20 mM Tris, pH 8.0 was loaded onto a column packed with an anion exchange resin, Q Sepharose HP, to 20 mg/mL resin. After loading, the column was washed with 6 M urea, 20 mM Tris, pH 9.0. TFPI was eluted and 10 mg/ml of Glass H (polyphosphate) in 6 M urea, 10 mM Tris, pH 9.0.

Example 6

Elution of TFPI from chromatography resin in aqueous buffer using polyionic compounds.

TABLE 2

| 0.5 mg/ml TFPI formulated in: | t ½ (day) at 40° C. | |
| --- | --- | --- |
| | IEX-HPLC | PT assay |
| 10 mM Na Acetate, 150 mM NaCl, pH 5.5 | 10.8 | 17.2 |
| 10 mM Na Citrate. 150 mM NaCl, pH 5.5 | 12.2 | 24.4 |
| 10 mM Na Acetate, 8% (w/v) Sucrose, pH 5.5 | 43.2 | 42.2 |
| 10 mM Na Acetate, 4.5% Mannitol, pH 5.5 | 47.7 | 46.6 |
| 10 mM Na Succinate, 150 mM NaCl, pH 6.0 | 7.8 | 11.0 |
| 10 mM Na Citrate, 150 mM NaCl, pH 6.0 | 13.0 | 18.8 |
| 10 mM Na Phosphate, 150 mM NaCl, pH 6.0 | 7.8 | 11.2 |
| 10 mM Na Phosphate, 500 mM NaCi, pH 6.0 | 52.2 | 68.9 |
| 10 mM Na Citrate, 150 mM NaCl, pH 6.5 | 10.0 | 14.8 |

For a positively charged resin, a positively charged compound is used and for a negatively charged resin, a negatively charged compound is used.

TFPI, in 3.5. M urea, 1 mg/ml polyphosphate, 50 mM Tris, pH 5.9 was loaded onto a cation exchange resin, SP Sepharose HP. After loading the column was washed with a non-urea containing buffer, 10 mg/ml polyphosphate, 10 mM sodium phosphate, pH 5.0. TFPI was eluted in the same buffer at pH 7.5, without urea.

Example 7

Selective elution of TFPI from ion exchange resins using polyionic compounds.

Because of the charged ends of TFPI, oppositely charged polyionic compounds can bind to these ends. When the polyionic compound has a higher strength of binding to TFPI than does the resin, the TFPI may be selectively eluted from the chromatography resin.

TFPI, in 3.5. M urea, 1 mg/ml polyphosphate, 50 mM Tris, pH 5.9 was loaded onto a cation exchange resin, SP Sepharose HP. After loading, the column is washed with 6 M urea, 1 mg/ml polyphosphate, 10 mM sodium phosphate, pH 5.9. TFPI was eluted in a 25 column volume gradient up to 20 mg/ml of polyphosphate. TFPI starts to elute at about 2–3 mg/ml of polyphosphate.

Example 8

Neutralization of polyionic compounds prior to chromatographic separation of TFPI. TFPI can interact with charged polymers. This interaction may prevent binding and purification to chromatographic resins. By neutralizing the charged polymer with an oppositely charged polymer, TFPI may bind to the resin.

In a buffer containing polyphosphate (Glass H), TFPI does not bind to Express Ion S (Whatman)and no purification is achieved. By mixing PEI into the column load, TFPI now binds to the resin and TFPI can be purified.

Example 9

Refolding and purification of recombinant human TFPI (rhTFPI) using Polyphosphate (Glass H) Facilitated Refolding Process.

Inclusion bodies containing about 40 g of rhTFPI were thawed by removing the containers from the −20° C. freezer and incubating them in a cold room at 4–10° C. for approximately 196 hours. The thawed inclusion bodies were then dispersed with a high shear mixer to reduce the clumping that occurs during freeing. The thawed inclusion bodies were added to 80 L of 3 M urea, 50 mM Tris-Cl, pH 10.5 buffer containing 2 g/L Glass H contained in a 100 L polyethylene tank equipped with an overhead stirrer. The contents were mixed for approximately 15 minutes, and then the absorbance of the solution is measured at 280 nm. If the absorbance is greater than the mixture was diluted with sufficient dissolution buffer to obtain an absorbance at 280 nm of 1.0–1.1. The solution was incubated with gentle agitation for 15–30 minutes, and then sufficient cysteine was added to give a cysteine concentration of 0.1 mM. The solid L-cysteine was dissolved in approximately 50 ml of purified water and added to the refold mixture. The pH was checked and adjusted to pH 10.2 if necessary. The refold mixture was incubated with gentle agitation for 96–120 hours.

After approximately 96 h, the refolding process was terminated by adjusting the pH of the refold mixture to pH 5.9 using glacial acetic acid. Stirring was continued for 90 minutes and the pH checked. More acid was added, if necessary to adjust the pH to 5.9+/−0.1. A two-step filtration process was used to remove the particulates tat formed during previous steps and prepare the acidified refold mixture for SP-Sepharose HP chromatography. First the acidified refold mixture is passed through A Cuno 60LP depth filter (filter housing model 8ZP1P) using a peristaltic pump (¼–⅜ inch inner diameter silicon tubing).

The filter system was washed with 8–10 L of deionized 6 M urea before use. The filtrate was collected in a 100 L polyethylene tank. Back pressure was maintained at a constant 20 PSI. Initial flow rate for a new filter was approximately 5–6 L per minute. Filters were replaced when the flow rate dropped below 1 L per minute in order to maintain the back pressure at 20 PSI. The second stage of the filtration used a 0.45 micron filter cartridge (Sartorius Sartobran pH or equivalent) with a peristaltic pumping system. After filtration, the pH was checked, and adjusted to pH 5.9 if necessary.

The acidified, filtered refold was loaded onto the equilibrated SP Sepharose HP column at a flow rate of approximately 80.0 ml/min. Flow rate was adjusted to accommodate overnight loading of the acidified filtered refold mixture. The column was equilibrated in 6 M urea, 20 mM sodium phosphate buffer pH 5.9 prior to loading. After loading, the column is washed with 2 CV of 6 M urea, 0.3 M NaCl, 20 mM sodium phosphate buffer, pH 5.9 prior to the gradient elution step. The column flow rate was increased to 190–200 ml/min for the wash step and all subsequent steps (linear velocity=~47 cm/hr). The product was eluted from the column using a linear salt gradient from 0.3 to 0.5 M NaCl in 6 M urea, 20 mM sodium phosphate buffer, pH 5.9. The gradient was formed by delivering 6 M urea, 0.5 M NaCl, 20 mM sodium phosphate buffer into 6 M urea, 0.3 M NaCl, 20 mM sodium phosphate buffer. Limit buffer was pumped with a Masterflex pump (model 7553-20) with a Math head (model 7015.21) at a flow rate of approximately 100 ml/min. with vigorous mixing using a Paratrol A mixer from Parametrics (model 250210). The total volume of the gradient was 71.0 liters or 13.0 CV. The pH of the gradient buffers was 5.92 (+/−0.02). Fractions are evaluated qualitatively using SDS PAGE and pooled based on the content of the correctly folded SC-59735 relative to other misfolds and impurities. After pooling the process stream is referred to as the S pool.

The pH of the S pool was next adjusted to pH 8.0 with 2.5 N NaOH. The S pool was concentrated 2–3 fold to approximately 2 L using an Amicon DC-10L ultrafiltration unit containing an Amicon YM10 spiral cartridge (10,000 M.W. cut-off membrane). After concentration, the concentrated S pool was diafiltered against 7 volumes of 6 M urea, 20 mM Tris-HCl buffer, pH 8.0. The diafiltration was considered complete when the conductivity of the retentate was below 2 mS. The diafiltered concentrate was drained from the ultrafiltration unit and the unit was washed with approximately 1 L of diafiltration buffer. The was is combined with the concentrate to form the Q-load.

An Amicon column (7.0 cm diameter) was packed with approximately 700 ml of Q-Sepharose high performance medium (Pharmacia Q-Sepharose HP). The column was packed with 20% ethanol at 20 psi. The bed height after packing was approximately 18 cm. The column was equilibrated with 5 CF of 6 M urea, 0.02 M Tris/HCl buffer, pH 8. The target for protein loading is 8–10 mg protein/ml Q Sepharose resin. The Q load was applied to the column at a flow rate 30–35 ml/mm (50 cm/hr). After loading, the column was washed with approximately 5 CV of 6 M urea, 2 mM Tris/Hcl buffer, pH 8.0, or until the absorbance at 280 nm returned to baseline. The product was eluted using a sodium chloride gradient from 0–0.15 M NaCl in 6 M urea, 20 mM Tris/HCl buffer, pH 8.0 over 25 column volumes. The first seven column volumes were collected as a single fraction, followed by 30 fractions of 0.25 column volume each.

Fractions are routinely analyzed by reducing and non-reducing SDS-PAGE and size exclusion chromatography. Fractions are pooled based on aggregate content (<5% by SEC HPLC Method MSL 13929) and qualitative evaluation by SDS PAGE to assess purity. The fractions are stored frozen at −20° C. until pooled.

Acceptable Q Sepharose fractions were pooled, and the pH of the pool was adjusted to 7.2 using 2 M HCl. The pool was then concentrated approximately 5 fold in an Amicon DC-1 ultrafiltration system containing a S1Y1 Amicon YM-10 cartridge (10,000 MWCO spiral cartridge membrane). The concentrated Q Pool was then diafiltered against seven column volumes of 2 M urea, 0.15 M NaCl, 20 mM sodium phosphate buffer, pH 7.2. Following ultrafiltration, the solution was drained from the ultrafiltration system. Approximately 100 ml of 2 M urea, 0.15 M NaCl, 20 mM sodium phosphate buffer, pH 7.2 was circulated through the ultrafiltration system for approximately 5 min. The rinse solution was combined with the original concentrate and the solution was filtered through a 0.45 micron vacuum filter unit (Nalgene).

Example 10

Refolding and Purification of rhTFPI using Polyethyleneimine (PEI) Facilitated Refolding Process.

Inclusion bodies containing about 40 g of rhTFPI were thawed by removing the containers from the −20° C. freezer and incubating them in a cold room at 4–10° C. for approximately 96 hours. The thawed inclusion bodies were then dispersed with a high shear mixer to reduce the clumping that occurs during freezing. The inclusion body slurry was vigorously blended for approximately 1 minute using a polytron homogenizer (Brinkman model PT45/80) or until the inclusion bodies were then added to 40 L of 6 M urea 100 mM Tris/HCl buffer pH 9.8 containing 300 mM NaCl and 0.4 g/L PEI contained in a 100 L polyethylene tank equipped with an overhead stirrer. The mixture was vigorously stirred for 20–30 min. The pH was monitored and adjusted to pH 9.8 as necessary. The absorbance of the dissolved inclusion body mixture was measured at 280 nm, and if the absorbance was greater than 2.1, the sample was diluted with 10 liters of the dissolution buffer described above to obtain an A280 value of 2.0–2.1. Gentle agitation was continued for another 15–30 minutes. Next, the dissolved inclusion body solution was diluted with an equal volume of 1.0 M urea, 300 mM NaCl solution. Finally, L-cysteine was added to give a final concentration of 0.25 mM. The solid L-cysteine was dissolved in 50 ml of WFI and added as a solution to the diluted refold. The pH was checked and adjusted, if necessary. The refold continued with gentle mixing for 96–120 hours with periodic checks of the pH, and adjustment to pH 9.8, if necessary. The progress of the refold was monitored by Mon-S cation exchange and prothrombin time assays.

After approximately 96 h, the refolding process was terminated by adjusting the pH of the refold to pH 5.9 using glacial acetic acid. Stirring was continued for 90 minutes and the pH checked. More acid was added, if necessary to adjust the pH to 5.9 +/−0.1.

A two-step filtration process was used to remove the particulates that formed during previous steps and prepare the acidified refold for SP-Sepharose HP chromatograph. First, the acidified refold is passed through a Cuno 60LP depth filter (filter housing model 8ZP1P) using a peristaltic pump (¼–⅜ inch inner diameter silicon tubing).

The filter system was washed with 8–10 L of deionized 6 M urea before use. The filtrate was collected in a 100 L polyethylene tank. Back pressure was maintained at a constant 20 PSI. Initial flow rate for a new filter was approximately 5–6 L per minute. Filters were replaced when the flow rate dropped below 1 L per minute in order to maintain the back pressure at 20 PSI. The second stage of the filtration used a 0.45 micron filter cartridge (Sartorius Sartobran pH or equivalent) with a peristaltic pumping system. After filtration, the pH was checked, and adjusted to pH 5.9, if necessary.

The acidified, filtered refold was loaded onto the equilibrated SP Sepharose HP column at a flow rate of approximately 80.0 ml/min. Flow rate was adjusted to accommodate overnight loading of the acidified filtered refold. The column was then washed with 5.5 column volumes of 6 M urea, 0.3 M NaCl, 20 mM sodium phosphate buffer, pH 5.9. The column flow rate was increased to 190–200 ml/min for the wash step and all subsequent steps (linear velocity=~47 cm/hr). The product was eluted from the column using a linear salt gradient from 0.3 to 0.5 M NaCl in 6 M urea, 20 mM sodium phosphate buffer, pH 5.9. The gradient was formed by delivering 6 M urea, 0.5 M NaCl, 20 mM sodium phosphate buffer into 6 M urea, 0.3 M NaCl, 20 mM sodium phosphate buffer into 6 M urea, 0.3 M NaCl, 20 mM sodium phosphate buffer. Limit buffer was pumped with a Masterflex pump (model 7553-20) with a Masterflex head (model 7015.21) at a flow rate of approximately 100 ml/min with vigorous mixing using a Paratrol A mixer from Parametrics (model 250210). The total volume of the gradient was 71.0 liters or 13.0 CV. The pH of the gradient buffers was 5.92 (+/−0.02).

Fraction collection was started when the column inlet conductivity reached 28.0–28.5 mS/cm as measured by the in-line Radiometer conductivity meter. Forty 500 ml fractions (0.1 CV) were collected. A Pharmacia Frac-300 fraction collector was used with numbered, 500 ml polypropylene bottles. When the fraction collection was stopped, the remainder of the gradient was collected as a pool.

Column fractions were assayed by A280, size exclusion HPLC, and in addition, for informational purposes, SDS PAGE, reverse phase HPLC, and PT assays. Fractions were pooled if they met the pooling criteria of containing 20% of less aggregate as determined by the in process SEC HPLC. Pooled SP Sepharose fractions are referred to as the S Pool.

The pH of the S-pool was next adjusted to pH 8.0 with 2.5 N NaOH. The S Pool was concentrated 2–3 fold to approximately 2 L using an Amicon DC-10L ultrafiltration unit containing an Amicon YM10 spiral cartridge (10,000 N.W. cut-off membrane). After concentration, the concentrated S Pool was diafiltered against 7 volumes of 6 M urea, 20 mM Tris-HCl buffer, pH 8.0. The diafiltration was considered complete when the conductivity of the retentate was below 2 mS. The diafiltered concentrate was drained from the ultrafiltration unit and the unit was washed with approximately 1 L of diafiltration buffer. The wash is combined with the concentrate to form the Q-load.

An Amicon column (7.0 cm diameter) was packed with approximately 700 ml of Q-Sepharose high performance medium (Pharmacia Q-Sepharose HP). The column was packed in 20% ethanol at 20 psi. The bed height after packing was approximately 18 cm The column was equilibrated with 5 CV of 6 M urea, 0.02 M Tris/HCl buffer, pH 8. The target for protein loading is 8–10 mg protein/ml Q Sepharose resin. The Q load was applied to the column at a flow rate 30–35 ml/min (50 cm/hr). After loading, the column was washed with approximately 5 CV of 6 M urea, 20 mM Tris/HCl buffer, pH 8.0, or until the absorbance at 280 nm returned to baseline. The product was eluted using a sodium chloride gradient from 0–0.15 M NaCl in 6 M urea, 20 mM Tris/HCl buffer, pH 8.0 over 25 column volumes. The first seven column volumes were collected as a single fraction, followed by 30 fractions of 0.25 column volume each.

Fractions are routinely analyzed by reducing and nonreducing SDS-PAGE and size exclusion chromatography. Fractions are pooled based on aggregate content (5% by SEC HPLC) and qualitative evaluation by SDS PAGE to assess purity. The fractions are stored frozen at −20° C. until pooled.

The Q-Sepharose fractions to be pooled were thawed by incubation at 2–8° C., pooled, and the pH of the pool was adjusted to 7.2 using 2 M HCl. The pool was then concentrated approximately 5 fold in an Amicon DC-1 ultrafiltration system containing a S1Y1 Amicon YM-10 cartridge (10,000 MWCO spiral cartridge membrane). The concentrated Q Pool was then diafiltered against seven column volumes of 2 M urea, 0.15 M NaCl, 20 mM sodium phosphate buffer, pH 7.2. Following ultrafiltration, the solution was drained from the ultrafiltration system. Approximately 100 ml of 2 M urea, 0.15 M NaCl, 20 mM sodium phosphate buffer, pH 7.2 was circulated through the ultrafiltration system for approximately 5 min. The rinse solution was combined with the original concentrate and filtered through a 0.45 micron vacuum filter unit (Nalgene).

Example 11

About 2 g of rhTFPI (43 ml inclusion body slurry containing 46 mg/ml rhTFPI) was dissolved with mixing in 4 L of 50 mM Tris buffer, pH 10.5 containing 4 g/l polyphosphate (Glass H, FMC Corporation) 2–8° C. Sufficient cysteine and cystine was added to make the solutions 0.1 mM and 0.05 mM respectively. The pH was maintained at pH 10.5 with 1 N NaOH. The refold solution was incubated at 2–8° C. with gentle mixing for 72–96 h.

The refold was next adjusted to pH 6 using glacial acetic acid and then filtered through a 0.2 micron filter. An aliquot of the filtered refold was applied to a 200 ml column of SP-Sepharose BP (Pharmacia) previously equilibrated in 0.4% Glass H, 20 mM sodium phosphate pH 6 buffer after loading, the column was washed with 4 column volumes of 0.4% Glass H, 20 mM sodium phosphate pH6 buffer. The column was eluted using a linear pH gradient from 0.4% Glass H, 20 mM sodium phosphate buffer pH 6 to 0.4% Glass H, 50 mM Tris pH 8 buffer. Fractions were collected and analyzed by SDS PAGE. Relatively pure rhTFPI could be refolded and purified in this manner.

Example 12

Improved solubility of rhTFPI in water by formation of a complex between TFPI and polyphosphate (GDS 5327046-47)

About 10 g of purified rhTFPI in about 1 liter of 2 M urea, 125 mM sodium chloride, 20 mM sodium phosphate pH 7.4 buffer was thawed by incubation at 2–8° C. for 18–36 h. Sufficient dry urea was added to make the solution 6 M in urea. The solution was then filtered through a 0.2 micron filter. Five g of polyphosphate glass (Glass H, FMC) was dissolved in 50 ml of 6 M urea, adjusted to pH 7 with 1 N NaOH, and added to the protein solution. The solution was then concentrated by ultrafiltration using 1 square foot of membrane (Amicon S1Y3) to about 400 ml (~25 mg/ml) and diafiltered against 10 volumes (about 4 liters) of purified water to remove residual urea. After diafiltration, the solution was concentrated to about 250 ml and removed from the ultrafiltration unit. The ultrafiltration unit was washed with about 150 ml of purified water and the was added to the protein concentrate. The final protein concentrate contained almost 10 g of protein in 400 ml of water (about 24 mg/ml protein). The normal solubility of rhTFPI in water is less than 0.5 mg/ml.

Example 13

Use of cationic polymers for removal of *E. coli* contaminants from TFPI cell lysates and refractile bodies.

The use of cationic polymers to precipitate and remove E coli contaminants from crude TFPI intermediates (lysates; refractile bodies) can significantly improve subsequence process operations (refolding, chromatography etc.) A random screening of cationic polymers identified candidates which selectively precipitate bacterial contaminants while TFPI remains in solution. Specifically, Betz polymer 624 precipitated substantial amounts of bacterial contaminants, while leaving TFPI in solution in an aqueous environment.

Solubilized TFPI refractile bodies (in 3.5 M guanidine hydrochloride, 2 M sodium chloride, 50 mM TRIS, 50 mM dithiothreitol, pH7.1) was the starting material used for a polymer screening experiment. This material was diluted 10 fold into a 0.5% solution of various polymers. The precipitates from this experiment were analyzed by SDS-PAGE for the presence of TFPI. Betz polymer 624 precipitated substantial amounts of contaminants, no TFPI, and resulted in a clear aqueous solution.

Example 14

The use of aqueous two phase extraction with a polyethylene glycol (PEG), polyphosphate, urea system offers processing advantages for TFPI purification. Typical aqueous two phase systems consist of two polymer systems (e.g., PEG and dextran) or a polymer and salt (e.g., PEG and sulfate). The system described here has advantages in that the polyphosphate chain length can be optimized for the separation, is inexpensive and is specific in removing problematic contaminants from TFPI refractile bodies known to interfere with refolding and chromatography (native polyphosphate and associated divalent metals).

TFPI refractile bodies were solubilized in 7 M urea, 10 mM CAPS, 1% monothioglycerol pH10. Polyphosphate and PEG of different chain lengths were added to form two phases. Upon phases separation, the TFPI partitioned into the PEG rich upper phase, leaving the polyphosphates and associated contaminants in the lower phase. Separation is effected by both PEG and polyphosphate chain length and can be optimized by varying both.

Example 15

Charged polymer facilitated refolding of recombinant tissue plasminogen activator (t-PA) from *E. coli* inclusion bodies Five grams (wet weight) of inclusion bodies containing about 2 grams of recombinant tissue plasminogen activator are added to about 1 liter of 0.5% Glass H, 50 mM Tris buffer pH 10.8 containing 1 mM reduced glutathione (GSH) and 0.2 mM glutthione disulfide (GSSG). The mixture is thoroughly blended using a polytron (Bring) homogenizer for 2–3 minutes to thoroughly disperse the inclusion bodies. The mixture is incubated with mixing using an overhead stirrer for 15 minutes while the pH is maintained at 10.5–10.9 using 1 N NaOH. The mixture is then gently mixed for 48–72 hours at 2–8° C.

Example 16

Charged polymer facilitated refolding of bovine somatotropin from *E. coli* inclusion bodies Ten grams (wet weight) of inclusion bodies containing 5 grams of bovine somatotropin are added to about 1 liter of 1% Glass H, 50 mM Tris buffer pH 10.5. The mixture is thoroughly blended using a polytron (Brinkman) homogenizer for 2–3 minutes to thoroughly disperse the inclusion bodies. The mixture is incubated with mixing using an overhead stirrer for 15 minutes while the pH is maintained at 10.4–10.6 using 1 N NaOH. Solid cysteine (121 mg) is added to make the reaction 1 mM cysteine, and the refolding reaction is mixed for 48–72 hours The patents, patent applications and publications cited herein are incorporated by reference.

The present invention has been described with reference to specific embodiments. However, this application is intended to cover those changes and substitutions which may be made by those skilled in the art without departing from the spirit and the scope of the appended claims.

---

We claim:

1. A solution having a pH of from 5 to 10, comprising from 200 mM arginine to 300 mM arginine, and further comprising more than 0.2 mg/ml of a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions.

2. The solution of claim 1 wherein said arginine is L-arginine.

3. The solution of claim 1 comprising from more than 0.2 to 20 mg/ml of said polypeptide.

4. The solution of claim 2 wherein the polypeptide is human Tissue Factor Pathway Inhibitor (TFPI) having the amino acid sequence shown in FIG. 4 and having one further amino acid which is an amino-terminal alanine.

5. The solution of claim 1 comprising 300 mM arginine.

6. The solution of claim 4 having a citrate/citric acid buffer at a total buffer concentration from 5 mM to 300 mM.

7. The solution of claim 1 having a pH of 5.5 and comprising human Tissue Factor Pathway Inhibitor (TFPI) having the amino acid sequence shown in FIG. 4 and having one further amino acid which is an amino-terminal alanine, 300 mM L-arginine, and a citrate/citric acid buffer at a total buffer concentration of 20 mM.

8. A solution having a pH of from 5 to 10, comprising more than 0.2 mg/ml of a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and further comprising a solubilizer selected from the group consisting of sucrose, mannitol, sorbitol, citrate, isocitrate, succinate, malate, polyphosphate, acetate, polysorbate-80, polyethylene glycol, histidine, imidazole, glutamate, glycine, ammonium sulfate, and sodium dodecyl sulfate.

9. The solution of claim 8 wherein the polypeptide is present at a concentration from 1 to 20 mg/ml.

10. The solution of claim 9 wherein the polypeptide is present at a concentration from 1 to 10 mg/ml.

11. The solution of claim 8 wherein the solution comprises 0.5M sodium citrate.

12. The solution of claim 8 wherein the solution comprises 0.5M sodium isocitrate.

13. The solution of claim 8 wherein the pH of the solution is below pH 7.0, and wherein the solubilizer is not glycine.

14. The solution of claim 8 wherein the solubilizer is acetate ion and the acetate ion is present in the solution at a concentration from 5 mM to 200 mM.

15. The solution of claim 8 wherein the solubilizer is citrate ion and the citrate ion is present in the solution as sodium citrate or potassium citrate at a concentration from 50 mM to 500 mM.

16. The solution of claim 8 wherein the solubilizer is isocitrate ion and the isocitrate ion is present in the solution as sodium isocitrate or potassium isocitrate at a concentration from 100 mM to 500 mM.

17. The solution of claim 8 wherein the solubilizer is glycine and the glycine is present in the solution at a concentration from 5 mM to 20 mM.

18. The solution of claim 8 wherein the solubilizer is glutamate and the glutamate is present in the solution at a concentration from 5 mM to 20 mM.

19. The solution of claim 8 wherein the solubilizer is succinate ion and the succinate ion is present in the solution as sodium succinate at a concentration from 5 mM to 20 mM.

20. The solution of claim 8 wherein the solubilizer is histidine and the histidine is present in the solution at a concentration from 5 mM to 20 mM.

21. The solution of claim 8 wherein the solubilizer is imidazole and the imidazole is present in the solution at a concentration from 5 mM to 20 mM.

22. The solution of claim 8 wherein the solubilizer is sodium dodecyl sulfate and the sodium dodecyl sulfate is present in the solution at a concentration from 0.001% to 0.1% (weight/volume).

23. The solution of claim 8 wherein the solubilizer is polyethylene glycol and the polyethylene glycol is present in the solution at a concentration from 0.2% to 10% (weight/volume).

24. The solution of claim 8 wherein the solubilizer is sucrose and the sucrose is present in the solution at a concentration from 0.2% to 10% (weight/volume).

25. The solution of claim 8 wherein the solubilizer is mannitol and the mannitol is present in the solution at a concentration from 1.0% to 5.0% (weight/volume).

26. The solution of claim 8 wherein the solubilizer is sorbitol and the sorbitol is present in the solution at a concentration from 0.2% to 10% (weight/volume).

27. The solution of claim 8 comprising at least 20 mM citrate.

28. The solution of claim 8 comprising at least 5 mM sodium acetate.

29. The solution of claim 8 comprising at least 0.005% (w/v) polysorbate-80.

30. The solution of claim 8 comprising at least 5 mM histidine.

31. The solution of claim 8 comprising at least 10 mM imidazole.

32. The solution of claim 8 comprising at least 1% (w/v) glutamate.

33. The solution of claim 8 comprising at least 0.1% (w/v) polyphosphate.

34. The solution of claim 8 comprising at least 120 mM ammonium sulfate.

35. The solution of claim 8 comprising at least 0.02% (w/v) sodium dodecyl sulfate.

36. A solution according to any one of claims 8–35 wherein the polypeptide is human Tissue Factor Pathway Inhibitor (TFPI) having the amino acid sequence shown in FIG. 4 and having one further amino acid which is an amino-terminal alanine.

37. A solution according to claim 36 which is pharmaceutically acceptable.

38. A solution according to any one of claims 8–35 which is pharmaceutically acceptable.

39. An aqueous composition comprising (1) a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and (2) a stabilizer of the polypeptide selected from the group consisting of polysorbate-80, mannitol, sucrose, chloride, acetate, citrate, phosphate, and mixtures thereof, wherein the half-life at 40° C. of the polypeptide in said composition, as determined using prothrombin time, is greater than that of a composition comprising TFPI, 150 mM sodium chloride, and 10 mM sodium phosphate and having a pH of 6.

40. The composition of claim 39 wherein the half life is from 20 to about 70 days.

41. The composition of claim 40 wherein the pH of the composition is from 5 to 10.

42. The composition of claim 41 wherein the stabilizer is selected from the group consisting of sodium chloride at a concentration of at least 150 mM, sucrose at a concentration of at least 8% (weight/volume), and mannitol at a concentration of at least 4.5% (weight/volume).

43. The composition of claim 42 wherein the stabilizer is sodium chloride at a concentration of at least 150 mM.

44. The composition of claim 43 further comprising 10 mM sodium citrate.

45. The composition of claim 44 having a pH of about 5.5.

46. The composition of claim 43 having a sodium chloride concentration of at least 500 mM sodium chloride.

47. The composition of claim 46 further comprising a sodium phosphate buffer at a total buffer concentration of about 10 mM.

48. The composition of claim 47 having a pH of about 6.0.

49. The composition of claim 42 wherein the stabilizer is sucrose at a concentration of at least 8% (weight/volume).

50. The composition of claim 49 further comprising 10 mM sodium acetate.

51. The composition of claim 50 having a pH of about 5.5.

52. The composition of claim 42 wherein the stabilizer is mannitol at a concentration of at least 4.5% (weight/volume).

53. The composition of claim 52 further comprising 10 mM sodium acetate.

54. The composition of claim 53 having a pH of about 5.5.

55. The composition of claim 39 comprising 150 mM sodium chloride, 0.005% (weight/volume) polysorbate-80, and sodium phosphate buffer at a concentration of at least 50 mM and having a pH of 7.

56. A composition of any of claims 39–55 wherein the polypeptide is human Tissue Factor Pathway Inhibitor (TFPI) having the amino acid sequence shown in FIG. 4 and having one further amino acid which is an amino-terminal alanine.

57. The solution of claim 1 comprising more than 1 mg/ml of said polypeptide.

58. The solution of claim 57 comprising more than 5 mg/ml of said polypeptide.

59. The solution of claim 58 comprising more than 10 mg/ml of said polypeptide.

60. The solution of claim 59 comprising more than 20 mg/ml of said polypeptide.

61. The solution of claim 3 comprising from more than 0.2 to 20 mg/ml of said polypeptide.

62. The solution of claim 61 comprising from 1 to 10 mg/ml of said polypeptide.

63. The solution of claim 61 comprising from 5 to 20 mg/ml of said polypeptide.

64. A solution having a pH of from 5 to 10, comprising more than 0.2 mg/ml of a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and further comprising a solubilizer selected from the group consisting of phosphate at a concentration of less than 20 mM or at least 500 mM; acetate at a concentration of at most 20 mM or at least 100 mM; and sulfate at a concentration of at least 120 mM.

65. The solution of claim 64 wherein the phosphate is sodium phosphate and the sodium phosphate is at a concentration selected from the group consisting of 10 mM and 500 mM.

66. The solution of claim 64 wherein the acetate is sodium acetate and the sodium acetate is at a concentration selected from the group consisting of 5 mM, 10 mM, 20 mM, 100 mM, and 200 mM.

67. The solution of claim 64 wherein the sulfate is sodium sulfate at a concentration of 260 mM.

68. The solution of claim 64 wherein the sulfate is ammonium sulfate and the ammonium sulfate is at a concentration selected from the group consisting of 120 mM, 500 mM, and 1 M.

69. A solution having a pH of from 5 to 10, comprising more than 0.2 mg/ml of a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and further comprising a solubilizer selected from the group consisting of acetate and more than 20 mM phosphate, wherein the solution does not comprise urea.

70. A solution having a pH of from 5 to 10, comprising more than 0.2 mg/ml of a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and further comprising a first solubilizer selected from the group consisting of phosphate, sulfate, and acetate, and a second solubilizer selected from the group consisting of sodium chloride at a concentration of at least 1.0 M, magnesium chloride, triphosphate, succinic acid, tartaric acid, malic acid, isocitrate, sodium citrate, phosphate glass, mannitol, sucrose, PEG-400, polysorbate-80, and sorbitol.

71. An aqueous composition comprising (1) a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and (2) a stabilizer of the polypeptide selected from the group consisting of polysorbate-80, mannitol, sucrose, chloride, acetate, citrate, phosphate, and mixtures thereof, wherein the half-life at 40° C. of the polypeptide in said composition, as determined using prothrombin time, is from about 15 days to about 70 days.

72. An aqueous composition according to claim 71, wherein the half-life is from about 20 days to about 70 days.

73. An aqueous composition according to claim 71, comprising at least 0.15 mg/ml of said polypeptide.

74. An aqueous composition according to claim 73, comprising more than 0.2 mg/ml of said polypeptide.

75. An aqueous composition according to claim 71, further comprising from 200 mM arginine to 300 mM arginine.

76. An aqueous composition according to claim 71, having a pH of 5.5 and comprising human Tissue Factor Pathway Inhibitor (TFPI) having the amino acid sequence shown in FIG. 4 and having one further amino acid which is an amino-terminal alanine, 300 mM L-arginine, and a citrate/citric acid buffer at a total buffer concentration of 20 mM.

77. An aqueous composition according to claim 71, having a pH of below 7.0.

78. An aqueous composition according to claim 77, having a pH of about 5.5.

79. An aqueous composition according to claim 71, comprising at least 20 mM citrate.

80. An aqueous composition comprising (1) a polypeptide selected from the group consisting of (i) human Tissue Factor Pathway Inhibitor (TFPI) having the amino acid sequence shown in FIG. 4, (ii) human TFPI having the amino acid sequence shown in FIG. 4 and having one further amino acid which is an amino-terminal alanine, and (iii) muteins of (i) or (ii) having from 1 to 5 amino acid substitutions, and further comprising from 200 mM arginine to 300 mM arginine.

81. An aqueous composition according to claim 80, comprising at least 0.15 mg/ml of said polypeptide.

82. An aqueous composition according to claim 81, comprising more than 0.2 mg/ml of said polypeptide.

83. An aqueous composition according to claim 80, having a pH of below 7.0.

84. An aqueous composition according to claim 83, having a pH of about 5.5.

85. An aqueous composition according to claim 80, further comprising at least 20 mM citrate.

* * * * *

SEQUENCE LISTING

```
<160> NUMBER OF SEQ ID NOS: 1

<210> SEQ ID NO 1
<211> LENGTH: 276
<212> TYPE: PRT
<213> ORGANISM: Homo sapiens

<400> SEQUENCE: 1

Asp Ser Glu Glu Asp Glu Glu His Thr Ile Ile Thr Asp Thr Glu Leu
 1               5                  10                  15

Pro Pro Leu Lys Leu Met His Ser Phe Cys Ala Phe Lys Ala Asp Asp
            20                  25                  30

Gly Pro Cys Lys Ala Ile Met Lys Arg Phe Phe Phe Asn Ile Phe Thr
        35                  40                  45

Arg Gln Cys Glu Glu Phe Ile Tyr Gly Gly Cys Glu Gly Asn Gln Asn
    50                  55                  60

Arg Phe Glu Ser Leu Glu Glu Cys Lys Lys Met Cys Thr Arg Asp Asn
65                  70                  75                  80
```

```
Ala Asn Arg Ile Ile Lys Thr Thr Leu Gln Gln Glu Lys Pro Asp Phe
            85              90              95

Cys Phe Leu Glu Glu Asp Pro Gly Ile Cys Arg Gly Tyr Ile Thr Arg
            100             105             110

Tyr Phe Tyr Asn Asn Gln Thr Lys Gln Cys Glu Arg Phe Lys Tyr Gly
        115             120             125

Gly Cys Leu Gly Asn Met Asn Asn Phe Glu Thr Leu Glu Glu Cys Lys
        130             135             140

Asn Ile Cys Glu Asp Gly Pro Asn Gly Phe Gln Val Asp Asn Tyr Gly
145             150             155             160

Thr Gln Leu Asn Ala Val Asn Asn Ser Leu Thr Pro Gln Ser Thr Lys
            165             170             175

Val Pro Ser Leu Phe Glu Phe His Gly Pro Ser Trp Cys Leu Thr Pro
            180             185             190

Ala Asp Arg Gly Leu Cys Arg Ala Asn Glu Asn Arg Phe Tyr Tyr Asn
        195             200             205

Ser Val Ile Gly Lys Cys Arg Pro Phe Lys Tyr Ser Gly Cys Gly Gly
        210             215             220

Asn Glu Asn Asn Phe Thr Ser Lys Gln Glu Cys Leu Arg Ala Cys Lys
225             230             235             240

Lys Gly Phe Ile Gln Arg Ile Ser Lys Gly Gly Leu Ile Lys Thr Lys
            245             250             255

Arg Lys Arg Lys Lys Gln Arg Val Lys Ile Ala Tyr Glu Glu Ile Phe
            260             265             270

Val Lys Asn Met
        275
```